US010245301B2

(12) United States Patent
Cool et al.

(10) Patent No.: US 10,245,301 B2
(45) Date of Patent: *Apr. 2, 2019

(54) GLYCOSAMINOGLYCANS

(71) Applicant: Agency for Science, Technology and Research, Singapore (SG)

(72) Inventors: Simon McKenzie Cool, Singapore (SG); Victor Nurcombe, Singapore (SG); Christian Dombrowski, Singapore (SG)

(73) Assignee: Agency for Science, Technology and Research, Singapore (SG)

( * ) Notice: Subject to any disclaimer, the term of this patent is extended or adjusted under 35 U.S.C. 154(b) by 33 days.

This patent is subject to a terminal disclaimer.

(21) Appl. No.: 15/262,895

(22) Filed: Sep. 12, 2016

(65) Prior Publication Data

US 2016/0375099 A1    Dec. 29, 2016

Related U.S. Application Data

(63) Continuation of application No. 13/062,364, filed as application No. PCT/SG2009/000328 on Sep. 11, 2009, now Pat. No. 10,086,044.

(60) Provisional application No. 61/096,274, filed on Sep. 11, 2008.

(30) Foreign Application Priority Data

Oct. 6, 2008   (GB) .................................. 0818255.2

(51) Int. Cl.

| A61K 31/727 | (2006.01) |
|---|---|
| A61L 27/54 | (2006.01) |
| A61L 27/26 | (2006.01) |
| C08B 37/00 | (2006.01) |
| A61K 38/18 | (2006.01) |
| A61L 27/36 | (2006.01) |
| B01D 15/38 | (2006.01) |
| C07K 14/51 | (2006.01) |
| C12N 5/0775 | (2010.01) |
| A61K 31/737 | (2006.01) |
| A61K 35/28 | (2015.01) |
| A61L 27/38 | (2006.01) |
| A61K 35/12 | (2015.01) |

(52) U.S. Cl.
CPC ........ *A61K 38/1875* (2013.01); *A61K 31/727* (2013.01); *A61K 31/737* (2013.01); *A61K 35/28* (2013.01); *A61L 27/26* (2013.01); *A61L 27/365* (2013.01); *A61L 27/3834* (2013.01); *A61L 27/3847* (2013.01); *A61L 27/54* (2013.01); *B01D 15/3823* (2013.01); *C07K 14/51* (2013.01); *C08B 37/0003* (2013.01); *C08B 37/0075* (2013.01); *C12N 5/0663* (2013.01); *A61K 2035/124* (2013.01); *A61L 2300/236* (2013.01); *A61L 2300/252* (2013.01); *A61L 2300/414* (2013.01); *A61L 2430/02* (2013.01); *C12N 2501/155* (2013.01); *C12N 2501/90* (2013.01)

(58) Field of Classification Search
CPC .. A61K 31/727; A61K 31/726; A61K 9/0024; A61K 38/1875; A61L 27/20; A61L 27/227; A61L 27/54; C08B 37/0003; C08B 37/0075; C08B 37/0078

See application file for complete search history.

(56) References Cited

U.S. PATENT DOCUMENTS

| 2005/0288252 A1 | 12/2005 | Nurcombe et al. |
|---|---|---|
| 2008/0274156 A1 | 11/2008 | Nurcombe et al. |
| 2011/0159071 A1 | 6/2011 | Cool et al. |
| 2011/0165132 A1 | 7/2011 | Cool et al. |
| 2013/0045249 A1 | 2/2013 | Cool et al. |
| 2013/0071443 A1 | 3/2013 | Cool et al. |

FOREIGN PATENT DOCUMENTS

| EP | 0511830 A2 | 11/1992 |
|---|---|---|
| JP | 2008-074732 | 4/2008 |
| WO | WO2002/42336 | 5/2002 |
| WO | WO2005/014619 | 2/2005 |
| WO | WO2005/014656 | 2/2005 |
| WO | WO2005/100374 | 10/2005 |
| WO | WO2005/107772 | 11/2005 |
| WO | WO 2014/185858 A1 | 11/2014 |
| WO | WO 2014/193308 A1 | 12/2014 |

OTHER PUBLICATIONS

Hoke et al., "A heparin binding synthetic peptide from human HIP/RPL29 fails to specifically differentiate between anticoagulantly active and inactive species of heparin", Journal of Negative Results in BioMedicine (2003) 2:1 pp. 1-10.

Feyzi et al. (1998) The Journal of Biological Chemistry 273(22):13395-13398 "Age-dependent Modulation of Heparan Sulfate Structure and Function".

Bhakta et al. "Hyaluronic acid-based hydrogels functionalized with heparin that support controlled release of bioactive BMP-2", Biomaterials, 2012, vol. 33:6113-6122.

Brickman et al. (1998) "Structural Modification of Fibroblast Growth Factor-binding Heparan Sulfate at a Determinative Stage of Neural Development" The Journal of Biological Chemistry, 273(8):4350-4359.

Brickman et al. (Oct. 20, 1985) "Heparan Sulfates Mediate the Binding of Basic Fibroblast Growth Factor to a Specific Receptor on Neural Precursor Cells", The Journal of Biological Chemistry, vol. 270, No. 42, pp. 24941-24948.

Bruder et al. (1998) "Bone Regeneration by Implantation of Purified, Culture-Expanded Human Mesenchymas Stem Cells" Journal of Orthopaedic Research, 16:155-162.

Cardin and Weintraub (1989) "Molecular modeling of protein-glycosaminoglycan interactions", Arteriosclerosis, Thrombosis and Vascular Biology, vol. 9, pp. 21-32.

(Continued)

*Primary Examiner* — Leigh C Maier
(74) *Attorney, Agent, or Firm* — Adsero IP

(57) ABSTRACT

Heparan sulphate HS/BMP2 is disclosed, together with the use of HS/BMP2 in the repair and regeneration of bone tissue.

14 Claims, 41 Drawing Sheets

Specification includes a Sequence Listing.

(56) References Cited

OTHER PUBLICATIONS

Clarke et al. "Healing of an ulnar defect using a proprietary TCP bone graft substitute, JAXTM, in association with autologous osteogenic cells and growth factors", Bone, 2007, vol. 40:939-947.
Clarke et al. "In vitro testing of Advanced JAXTM Bone Void Filler System: species differences in the response of bone marrow stromal cells to β tri-calcium phosphate and carboxymethyl cellulose gel", J Mater Sci: Mater Med, 2007, vol. 18:2283-2290.
Cool and Nurcombe (2005) "The osteoblast-heparan sulfate axis: Control of the bone cell lineage", The International Journal of Biochemistry & Cell Biology, vol. 37, pp. 1739-1745.
European Office Action dated Jun. 10, 2014 in EP 12155580.9.
European Search Report dated Nov. 8, 2011 in EP 09 81 3323.
Fromm et al. (Jul. 2007) "Pattern and spacing of basic amino acids in heparin binding sites" Arch Biochem Biophys. 1:343(1):92-100.
Gallagher et al. "Molecular distinctions between heparan sulphate and heparin, Analysis of sulphation patterns indicates that heparan sulphate and heparin are separate families of N-suphated polysaccharides", Biochem. J. (1985) vol. 230:665-674.
Griffin et al. (1995) "Isolation and characterization of heparan sulfate from crude porcine intestinal mucosal peptidoglycan heparin", Carbohydrate Research, vol. 276, pp. 183-197.
Grünert et al. (2007) "Isolation of a native osteoblast matrix with a specific affinity for BMP2", J. Mol. Hist., vol. 38 pp. 393-404.
Grünert, Martin Herbert Peter (PhD thesis) "The novel isolation of heparan sulfate with a specific affinity for bone morphogenetic protein 2", The University of Queensland, (2008), TOC and abstract only.
Higashiyama et al. (Aug. 1993) The Journal of Cell Biology 122(4):933-940 "Heparin-binding EGF-like Growth Factor Stimulation of Smooth Muscle Cell Migration: Dependence on Interactions with Cell Surface Heparan Sulfate".
Hughes et al. "Adsorption of chondroitin-4-sulphate and heparin onto hydroxyapatite-effect of bovine serum albumin", Biomaterials, 1997, vol. 18:1001-1007.
International Preliminary Examination Report on Patentability issued in PCT/GB2009/000469 dated Mar. 15, 2011.
International Preliminary Examination Report on Patentability issued in PCT/SG2009/000328 dated Aug. 3, 2010.
International Search Report and Written Opinion issued in PCT/GB2009/000469 dated Mar. 22, 2010.
International Search Report and Written Opinion issued in PCT/SG2009/000328 dated Dec. 17, 2009.
Jackson et al. (Apr. 2006) "The Use of Heparan Sulfate to Augment Fracture Repair in a Rat Fracture Model" Journal of Orthopaedic Research 24:636-644.
Jha et al. "Perlecan domain I-conjugated, hyaluronic acid-based hydrogel particles for enhanced chondrogenic differentiation via BMP-2 release", Biomaterials, 2009, vol. 30:6964-6975.
Jiao et al. (Jan. 2007) "Heparan Sulfate Proteoglycans (HSPGs) Modulate BMP2 Osteogenic Bioactivity in C2C12 Cells", The Journal of Biological Chemistry, vol. 282, No. 2, pp. 1080-1086.
Kanzaki et al. (2008) "Heparin Inhibits BMP-2 Osteogenic Bioactivity by Binding to Both BMP-2 and BMP Receptor", J. Cell. Physiol., vol. 216, pp. 844-850.
Kisiel et al. "Complexation and Sequestration of BMP-2 from an ECM Mimetic Hyaluronan Gel for Improved Bone Formation" PLOS ONE, Oct. 2013, vol. 8(10):1-13.
Krampera et al. (2005) Blood 106(1):59-66 "HB-EGF/HER-1 signaling in bone marrow mesenchymal stem cells: inducing cell expansion and reversibly preventing multilineage differentiation".
Laterra et al. Cell surface heparan sulfate mediates some adhesive responses to glycosaminoglycan-binding matrices, including fibronectin. J Cell Bioi. Jan. 1983;96 (1 ):112-23.
Lee et al. "Controlled release of BMP-2 using a heparin-conjugated carrier system reduces in vivo adipose tissue formation", J Biomed Mater Res Part A, 2015, vol. 103A:545-554.
Lethias et al. (May 2001) "Identification and Characterization of a Conformational Heparin-binding Site Involving Two Fibronectin Type III Modules of Bovine Tenascin-X", The Journal of Biological Chemistry, vol. 276, No. 19, pp. 16432-16438.
Liao "Hyaluronan: Pharmaceutical Characterization and Drug Delivery", Drug Delivery, 2005, vol. 12:327-342.
Lin et al. "The effect of crosslinking heparin to demineralized bone matrix on mechanical strength and specific binding to human bone morphogenetic protein-2", Biomaterials, 2008, vol. 29: 1189-1197.
Linhardt et al. (1990) "Examination of the substrate specificity of heparin and heparan sulfate lyases" Biochemistry, 29(10):2611-2617.
Liu et al. (Mar. 1997) "A heparin-binding synthetic peptide of heparin/heparan sulfate-interacting protein modulates blood coagulation activities", Proc. Natl. Acad. Sci. USA, vol. 94, pp. 1739-1744.
Luong-Van et al. (2007) "In vitro biocompatibility and bioactivity of microencapsulated heparan sulfate", Biomaterials, vol. 28, pp. 2127-2136.
Manton et al. (2006) "Bone Specific Heparan Sulfates Induce Osteoblast Growth Arrest and Downregulation of Retinoblastoma Protein" Journal of Cellular Physiology 209:219-229.
Murali et al. "Affinity-selected heparan sulfate for bone repair", Biomaterials, 2013, vol. 34:5594-5605.
Murali et al. (2009) "Purification and Characterization of Heparan Sulfate From Human Primary Osteoblasts", Journal of Cellular, Biochemistry, vol. 108, No. 5, pp. 1132-1142.
Nurcombe et al. (Apr. 2, 1993) "Developmental Regulation of Neural Response to FGF-1 and FGF-2 by Heparan Sulfate Proteoglycan" Science 260:103-106.
Rabenstein et al. (2002) Nat. Prod. Rep 19:312-331, "Heparin and heparan sulfate: structure and function".
Rapraeger (Oct. 1995) "In the clutches of proteoglycans: how does heparan sulfate regulate FGF binding?", Chemistry & Biology, vol. 2, No. 10, pp. 645-649.
Rue and Ryan (2002) "Characterization of pseudorabies virus glycoprotein C attachment to heparan sulfate proteoglycans", Journal of General Virology, vol. 83, pp. 301-309.
Ruppert et al. (1996) "Human bone morphogenetic protein 2 contains a heparin-binding site which modifies its biological activity" Eur. J. Biochem. 237:295-302.
Saksela et al. (Aug. 1988) J. Cell Bio. 107(2):743-751, "Endothelial Cell-derived Heparan Sulfate Binds Basic Fibroblast Growth Factor and Protects It from Proteolytic Degradation".
Williamson et al. (1995) "Affinity Purification of Proteoglycans that Bind to the Amyloid Protein Precursor of Alzheimer's Disease", Journal of Neurochemistry, vol. 65, pp. 2201-2208.
Yang et al. "Surface modification of titanium with hydroxyapatite-heparin-BMP-2 enhances the efficacy of bone formation and osseointegration in vitro and in vivo", J Tissue Eng Regen Med, 2014, 11 pages.
Yayon et al. (Feb. 1991) "Cell Surface, Heparin-like Molecules Are Required for Binding of Basic Fibroblast Growth Factor to Its High Affinity Receptor", Cell, vol. 64, pp. 841-848.
Zhao et al. "Preparation and characterization of modified hydroxyapatite particles by heparin", Biomed. Mater., 2008, vol. 3:025016(6pp).

Figure 3
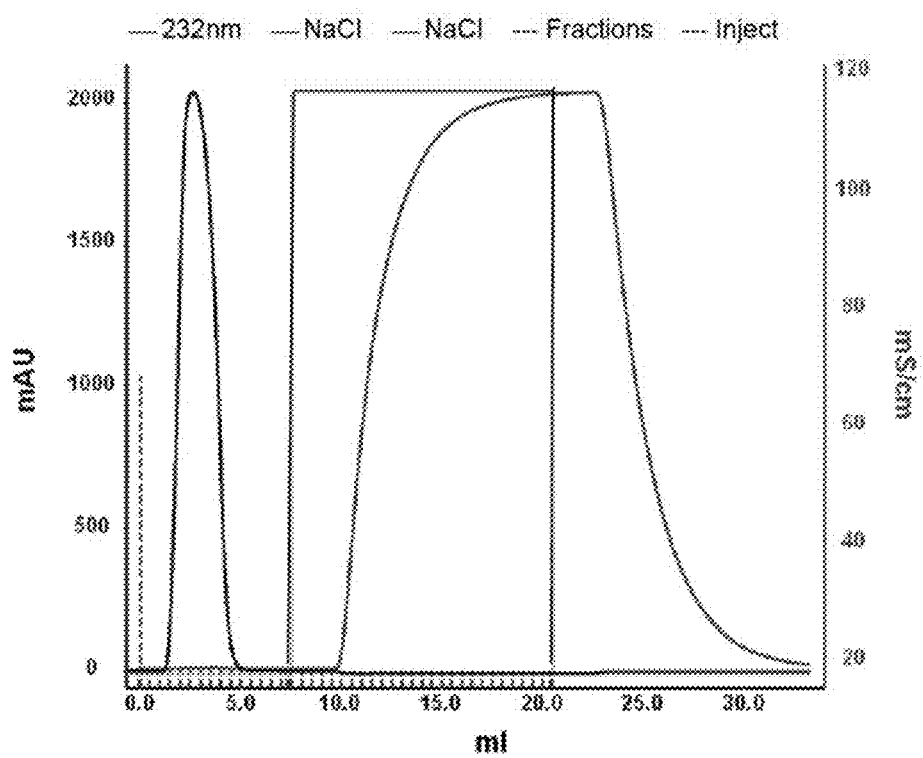
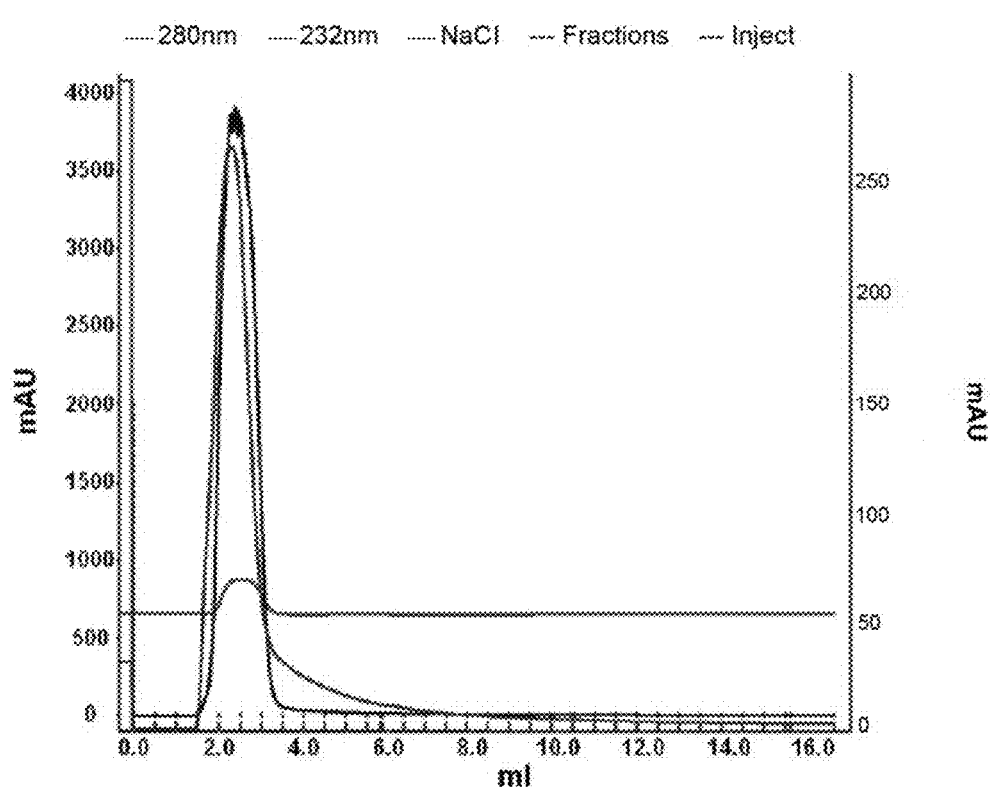
Figure 4

| | |
|---|---|
| 1 | MVAGTRCLLA LLLPQVLLGG AAGLVPELGR RKFAAASSGR PSSQPSDEVL SEFELRLLSM |
| 61 | FGLKQRPTPS RDAVVPPYML DLYRRHSGQP GSPAPDHRLE RAASRANTVR SFHHEESLEE |
| 121 | LPETSGKTTR RFFFNLSSIP TEEFITSAEL QVFREQMQDA LGNNSSFHHR INIYEIIKPA |
| 181 | TANSKFPVTR LLDTRLVNQN ASRWESFDVT PAVMRWTAQG HANHGFVVEV AHLEEKQGVS |
| 241 | KRHVRISRSL HQDEHSWSQI RPLLVTFGHD GKGHPLHKRE KRQAKHKQRK RLKSSCKRHP |
| 411 | LYVDFSDVGW NDWIVAPPGY HAFYCHGECP FPLADHLNST NHAIVQTLVN SVNSKIPKAC |
| 361 | CVPTELSAIS MLYLDENEKV VLKNYQDMVV EGCGCR |

Figure 35

| S.NO. | HS - Standards | BMP2 – Specific HS (%composition) | BMP2 – Non-Specific HS (%composition) | Celsus - HS (%composition) |
|---|---|---|---|---|
| 1 | UA - GlcN | 8.2 | 6.5 | 9.2 |
| 2 | UA - GlcNAc | 17.5 | 6.1 | 27.5 |
| 3 | UA - GlcN,6S | 3.7 | 1.8 | 1.0 |
| 4 | UA,2S - GlcN | 4.5 | 11.8 | 1.5 |
| 5 | UA - GlcNS | 16.2 | 21.5 | 7.1 |
| 6 | UA - GlcNAc,6S | --- | 3.3 | 5.4 |
| 7 | UA,2S - GlcNAc | --- | 3.3 | 0.5 |
| 8 | UA,2S - GlcN,6S | --- | --- | --- |
| 9 | UA - GlcNS,6S | --- | 0.4 | 7.1 |
| 10 | UA,2S - GlcNS | --- | --- | 6.1 |
| 11 | UA,2S - GlcNAc,6S | --- | --- | --- |
| 12 | UA,2S - GlcNS,6S | 0.5 | --- | 4.6 |
| | Unknown | 49.4 | 45.3 | 30.0 |

Figure 43

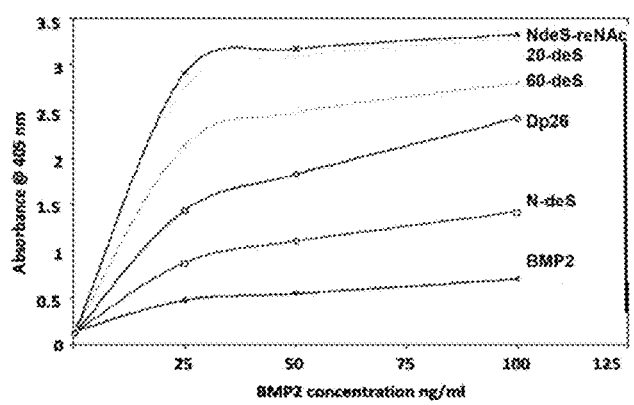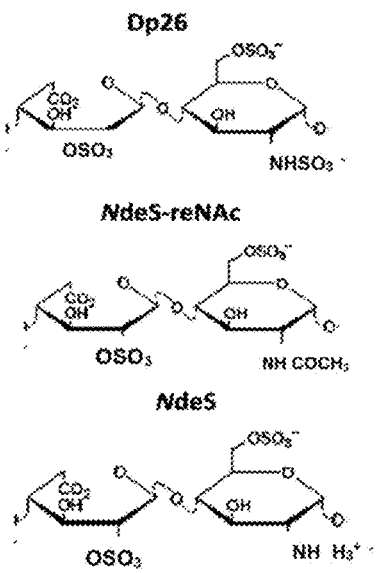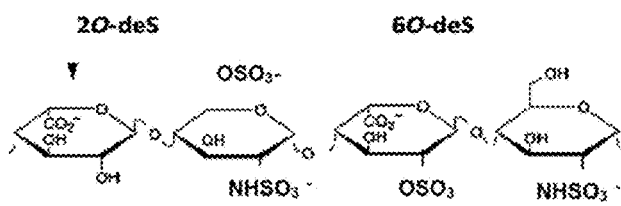
Figure 48
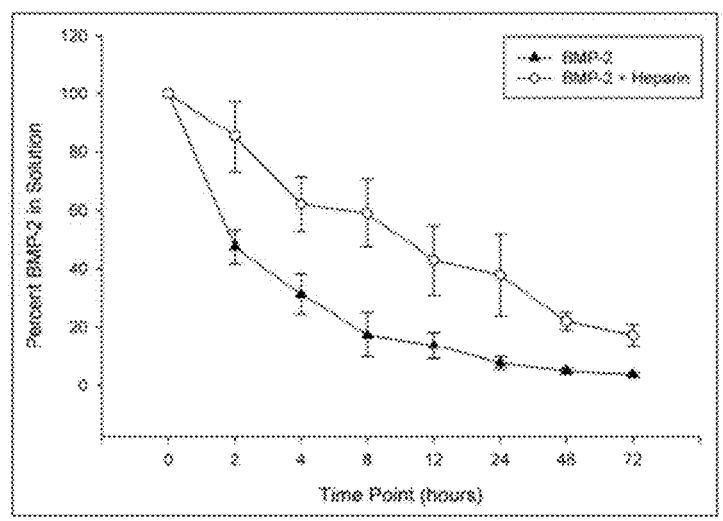
Figure 49

GLYCOSAMINOGLYCANS

CROSS-REFERENCE TO RELATED APPLICATION

This application is a continuation of pending U.S. application Ser. No. 13/062,364, having an effective filing date of Mar. 4, 2011, entitled "Heparan Sulphate Which Binds BMP2", which is a 35 U.S.C. § 371 national phase application of PCT/SG2009/000328, filed Sep. 11, 2009 (WO 2010/030244), entitled "A Heparan Sulphate Which Binds BMP2;" PCT/SG2009/000328 claims priority to U.S. Provisional Application Ser. No. 61/096,274, filed Sep. 11, 2008 and United Kingdom Application Serial No. 0818255.2, filed Oct. 6, 2008, each of which is incorporated herein by reference in its entirety.

FIELD OF THE INVENTION

The present invention relates to glycosaminoglycans capable of binding to BMP2, including their isolation and identification, and the use of the isolated glycosaminoglycans in the growth and/or development of tissue.

Incorporated by reference herein in its entirety is the Sequence Listing entitled "Sequence_Listing.txt", created Mar. 3, 2011, size of 6 kilobytes.

BACKGROUND TO THE INVENTION

Glycosaminoglycans (GAGs) are complex carbohydrate macromolecules responsible for performing and regulating a vast number of essential cellular functions.

GAGs have been implicated in the modulation or mediation of many signalling systems in concert with the many hundreds of known heparin-binding growth and adhesive factors. It is contemplated that the association of growth factors with GAGs modulates their various activities with a diverse range of actions, such as lengthening their half-lives by protecting them from proteolytic degradation, modulating localisation of these cytokines at the cell surface, mediating molecular interactions and stabilising ligand-receptor complexes.

There are an ever increasing number of identified heparin-binding growth factors, adding to the hundreds already known, most of which were purified by heparin affinity chromatography. They include the large fibroblast growth factor (FGF) family, the PDGFs, the pleiotropins through to the TGF-β superfamily of cytokines. This latter family of factors encompasses the osteo-inductive bone morphogenetic protein (BMP) subfamily, so named for their ability to induce ectopic bone formation.

The nature and effect of the interaction of GAGs and growth factors remains unclear. Although the interaction between FGF2 and particular saccharide sequences found within heparin has been shown to be of high affinity, it remains generally unclear whether the association between other growth factors and heparans involves a high affinity or specific binding interaction between an amino acid sequence or conformational epitope on the protein growth factor and a saccharide sequence embedded in the GAG, or whether the association is mediated by lower affinity, non-specific interactions between the GAG and protein growth factor.

If interactions between GAGs and proteins resident in, or secreted into, the extracellular matrix are specific, the binding partners need to be identified in order to unravel the interactions and understand how these interactions may be used or modulated to provide new treatments.

A major question that arises is, therefore, whether there are saccharide sequences embedded in the chains of GAG molecules that match primary amino acid sequence/3-dimensional tertiary conformation within the polypeptide backbone of growth factors so controlling their association, and thus bioactivity, with absolute, or at least relative, specificity.

Bone morphogenetic protein 2 (also called bone morphogenic protein 2, BMP2 or BMP-2) is a member of the TGF-β superfamily strongly implicated in the development of bone and cartilage. It is an osteogenic protein, i.e. is a potent inducer of osteoblast differentiation (Marie et al. (2002) Regulation of human cranial osteoblast phenotype by FGF-2, FGFR-2 and BMP-2 signaling". Histol. Histopathol. 17 (3): 877-85). Implantation of collagen sponges impregnated with BMP2 has been shown to induce new bone formation (Geiger M, Li R H, Friess W (November 2003). Collagen sponges for bone regeneration with rhBMP-2. *Adv. Drug Deliv. Rev.* 55 (12): 1613-29.). Recombinant human BMP2 is available for orthopaedic use in USA (e.g. INFUSE® Bone Graft, Medtronic Inc, USA).

SUMMARY OF THE INVENTION

The present invention concerns a heparan sulphate preparation, heparan sulphate HS/BMP2. HS/BMP2 has been found to enhance the generation, repair and regeneration of connective tissue.

In one aspect of the present invention heparan sulphate HS/BMP2 is provided. HS/BMP2 may be provided in isolated form or in substantially purified form. This may comprise providing a composition in which the heparan sulphate component is at least 80% HS/BMP2, more preferably one of at least 85%, 90%, 95%, 96%, 97%, 98%, 99% or 100%.

In preferred embodiments, HS/BMP2 is capable of binding a peptide or polypeptide having, or consisting of, the amino acid sequence of SEQ ID NO:1 or 6. In some embodiments this peptide is SEQ ID NO:1 or 6, in other embodiments it is a BMP2 protein. In some embodiments HS/BMP2 binds to a peptide having or consisting of the amino acid sequence of SEQ ID NO:1 or 6 with a $K_D$ of less than 100 µM, more preferably less than one of 50 µM, 40 µM, 30 µM, 20 µM, or 10 µM.

In some preferred embodiments HS/BMP2 is N-sulfated. This may comprise N-sulfation of N-acetyl-D-glucosamine (GlcNAc) residues in the heparan sulphate oligosaccharide chain. Preferably at least 80% of N-acetyl-D-glucosamine (GlcNAc) residues in the HS/BMP2 are N-sulfated. In some embodiments this may be one of at least 85%, 90%, 95%, 96%, 97%, 98%, 99% or 100%.

In some preferred embodiments HS/BMP2 is 6-O-sulfated (O-sulphation at C6 of N-sulphoglucosamine (GlcNS) residues). Preferably at least 80% of N-sulphoglucosamine (GlcNS) residues in the HS/BMP2 are 6-O-sulfated. In some embodiments this may be one of at least 85%, 90%, 95%, 96%, 97%, 98%, 99% or 100%.

HS/BMP2 may be obtained, identified, isolated or enriched according to the inventors' methodology described herein, which may comprise the following steps:

(i) providing a solid support having polypeptide molecules adhered to the support, wherein the polypeptide comprises a heparin-binding domain having the amino acid sequence of SEQ ID NO:1 or 6;

(ii) contacting the polypeptide molecules with a mixture comprising glycosaminoglycans such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes;

(v) collecting the dissociated glycosaminoglycans.

In the inventors' methodology the mixture may comprise glycosaminoglycans obtained from commercially available sources. One suitable source is an heparan sulphate fraction, e.g. a commercially available heparan sulphate. One suitable heparan sulphate fraction can be obtained during isolation of heparin from pig intestinal mucosa (e.g. Celsus Laboratories Inc.—sometimes called "Celsus HS"). Other suitable sources of heparan sulphate include heparan sulphate from any mammal (human or non-human), particularly from the kidney, lung or intestinal mucosa. In some embodiments the heparan sulphate is from pig (porcine) or cow (bovine) intestinal mucosa, kidney or lung. Another suitable source is osteoblast extracellular matrix material, or a heparan sulphate fraction obtained from osteoblast extracellular matrix material.

In another aspect of the present invention a composition comprising HS/BMP2 according to any one of the aspects above and BMP2 protein is provided.

In one aspect of the present invention a pharmaceutical composition or medicament is provided comprising HS/BMP2 in accordance with the aspects described above. The pharmaceutical composition or medicament may further comprise a pharmaceutically acceptable carrier, adjuvant or diluent.

In some embodiments the pharmaceutical composition is for use in a method of treatment, the method comprising the repair and/or regeneration of a broken bone. In some embodiments the pharmaceutical composition or medicament may further comprise BMP2 protein. In some embodiments the pharmaceutical composition or medicament may further comprise mesenchymal stem cells.

In another aspect of the present invention HS/BMP2 is provided for use in a method of medical treatment. The method of medical treatment may comprise a method of wound healing in vivo, the repair and/or regeneration of connective tissue, the repair and/or regeneration of bone and/or the repair and/or regeneration of bone in a mammal or a human.

In a related aspect of the present invention the use of HS/BMP2 in the manufacture of a medicament for use in a method of medical treatment is provided. In some embodiments the method of medical treatment comprises the repair and/or regeneration of a broken bone in a mammal or a human.

In a further aspect of the present invention a biocompatible implant or prosthesis comprising a biomaterial and HS/BMP2 is provided. In some embodiments the implant or prosthesis is coated with HS/BMP2. In some embodiments the implant or prosthesis is impregnated with HS/BMP2. The implant or prosthesis may be further coated or impregnated with BMP2 protein and/or with mesenchymal stem cells.

In another aspect of the present invention a method of forming a biocompatible implant or prosthesis is provided, the method comprising the step of coating or impregnating a biomaterial with HS/BMP2. In some embodiments the method further comprises coating or impregnating the biomaterial with one or both of BMP2 protein and mesenchymal stem cells.

In another aspect of the present invention a method of treating a bone fracture in a patient is provided, the method comprising administration of a therapeutically effective amount of HS/BMP2 to the patient. In some embodiments the method comprises administering HS/BMP2 to the tissue surrounding the fracture. In some embodiments the method comprises injection of HS/BMP2 to the tissue surrounding the fracture. In such methods the HS/BMP2 may be formulated as a pharmaceutical composition or medicament comprising HS/BMP2 and a pharmaceutically acceptable carrier, adjuvant or diluent.

In some embodiments the method may further comprise administering BMP2 protein to the patient. In such methods the HS/BMP2 and BMP2 protein may be formulated as a pharmaceutical composition comprising HS/BMP2 and BMP2 protein and a pharmaceutically acceptable carrier, adjuvant or diluent.

In some embodiments the method may further comprise administering mesenchymal stem cells to the patient. In such methods at least two of HS/BMP2, BMP2 protein and mesenchymal stem cells may be formulated in a pharmaceutical composition comprising at least two of the HS/BMP2, BMP2 protein and mesenchymal stem cells and a pharmaceutically acceptable carrier, adjuvant or diluent.

Preferably, the HS/BMP2, BMP2 protein and mesenchymal stem cells are respectively provided in therapeutically effective amounts. In some embodiments the method of treating bone fracture further comprises the step of formulating therapeutically effective amounts of HS/BMP2, and/or BMP2 protein and/or mesenchymal stem cells as a pharmaceutical composition comprising the HS/BMP2, and/or BMP2 protein and/or mesenchymal stem cells and a pharmaceutically acceptable carrier, adjuvant or diluent, wherein the pharmaceutical composition is administered to the patient.

In another aspect of the present invention a method of treating a bone fracture in a patient is provided, the method comprising surgically implanting a biocompatible implant or prosthesis, which implant or prosthesis comprises a biomaterial and HS/BMP2, into tissue of the patient at or surrounding the site of fracture.

In some embodiments the implant or prosthesis is coated with HS/BMP2. In some embodiments the implant or prosthesis is impregnated with HS/BMP2. In some embodiments the implant or prosthesis is further impregnated with one or both of BMP2 protein and mesenchymal stem cells.

In a further aspect of the present invention culture media is provided, the culture media comprising HS/BMP2.

In another aspect of the present invention the use of HS/BMP2 in cell culture in vitro is provided. In a related aspect of the present invention the use of HS/BMP2 in the growth of connective tissue in vitro is provided. In another related aspect of the present invention a method for growing connective tissue in vitro is provided, the method comprising culturing mesenchymal stem cells in contact with exogenously added HS/BMP2.

In yet a further aspect of the present invention a method of promoting osteogenesis is provided, the method comprising administering HS/BMP2 to bone precursor cells or bone stem cells. The method may involve contacting the bone precursor cells or bone stem cells with HS/BMP2 in vitro or in vivo. In some embodiments the bone precursor cells or bone stem cells are contacted with BMP2 protein simultaneously with HS/BMP2. In preferred embodiments the bone precursor or bone stem cells are mesenchymal stem cells.

In yet a further aspect of the present invention a method for the repair, replacement or regeneration of bone tissue in a human or animal patient in need of such treatment is provided, the method comprising:

(i) culturing mesenchymal stem cells in vitro in contact with HS/BMP2 for a period of time sufficient for said cells to form bone tissue;

(ii) collecting said bone tissue;

(iii) implanting said bone tissue into the body of the patient at a site of injury or disease to repair, replace or regenerate bone tissue in the patient.

In some embodiments the method further comprises contacting the mesenchymal stem cells in culture with exogenous BMP2 protein.

In another aspect of the present invention bone tissue obtained by in vitro culture of mesenchymal stem cells in the presence of HS/BMP2 is provided. In some embodiments the bone tissue is obtained by in vitro culture of mesenchymal stem cells in the presence of HS/BMP2 and BMP2 protein.

In a further aspect of the present invention a method of culturing mesenchymal stem cells is provided, the method comprising culturing mesenchymal stem cells in contact with HS/BMP2.

In yet a further aspect of the present invention a kit of parts is provided, the kit comprising a predetermined amount of HS/BMP2 and a predetermined amount of BMP2. The kit may comprise a first container containing the predetermined amount of HS/BMP2 and a second container containing the predetermined amount of BMP2. The kit may further comprise a predetermined amount of mesenchymal stem cells. The kit may be provided for use in a method of medical treatment. The method of medical treatment may comprise a method of wound healing in vivo, the repair and/or regeneration of connective tissue, the repair and/or regeneration of bone and/or the repair and/or regeneration of bone in a mammal or a human. The kit may be provided together with instructions for the administration of the HS/BMP2, BMP2 protein and/or mesenchymal stem cells separately, sequentially or simultaneously in order to provide the medical treatment.

In a further aspect of the present invention products are provided, the products containing therapeutically effective amounts of:

(i) HS/BMP2; and one or both of (ii) BMP2 protein;

(iii) Mesenchymal stem cells, for simultaneous, separate or sequential use in a method of medical treatment. The method of medical treatment may comprise a method of wound healing in vivo, the repair and/or regeneration of connective tissue, the repair and/or regeneration of bone and/or the repair and/or regeneration of bone in a mammal or a human. The products may optionally be formulated as a combined preparation for coadministration.

Further aspects of the present invention are set out below.

In one aspect of the present invention a GAG is provided having high binding affinity for BMP2. More preferably the GAG is a heparan sulphate (HS). In one embodiments the HS was isolated from a GAG mixture obtained from the extracellular matrix of osteoblasts by following the methodology described herein in which a polypeptide comprising the heparin-binding domain of BMP2 (SEQ ID NO:1) was attached to a solid support and GAG-polypeptide complexes were allowed to form. Dissociation of the GAG component from the GAG-polypeptide complexes led to isolation of a unique HS herein called "HS/BMP2" (sometimes called "HS-3" or "H53").

In another embodiment the same methodology was used to isolate HS/BMP2 from a commercially available heparan sulphate (Celsus HS) obtained during isolation of heparin from pig intestinal mucosa and available from Celsus Laboratories Inc, Cincinnatti, USA (e.g. INW-08-045, Heparan Sulphate I, Celsus Lab Inc, HO-03102, HO-10595, 10×100 mg).

It is the inventors belief that HS/BMP2 can be obtained from HS fractions obtained from a plurality of sources, including mammalian (human and non-human) tissue and/or extracellular matrix.

Accordingly, in one aspect of the present invention HS/BMP2 is provided. HS/BMP2 may be provided in isolated or purified form. In another aspect culture media comprising HS/BMP2 is provided.

In yet another aspect of the present invention a pharmaceutical composition or medicament comprising HS/BMP2 is provided, optionally in combination with a pharmaceutically acceptable carrier, adjuvant or diluent. In some embodiments pharmaceutical compositions or medicaments may further comprise BMP2 protein. Pharmaceutical compositions or medicaments comprising HS/BMP2 are provided for use in the prevention or treatment of injury or disease. The use of HS/BMP2 in the manufacture of a medicament for the prevention or treatment of injury or disease is also provided.

In a further aspect of the present invention, a method of preventing or treating injury or disease in a patient in need of treatment thereof is provided, the method comprising administering an effective amount of HS/BMP2 to the patient. The administered HS/BMP2 may be formulated in a suitable pharmaceutical composition or medicament and may further comprise a pharmaceutically acceptable carrier, adjuvant or diluent. Optionally, the pharmaceutical composition or medicament may also comprise BMP2 protein.

In another aspect of the present invention a method of promoting or inhibiting osteogenesis (the formation of bone cells and/or bone tissue) is provided comprising administering HS/BMP2 to bone precursor cells or bone stem cells.

In another aspect of the present invention a method of promoting or inhibiting the formation of cartilage tissue (chondrogenesis) is provided, comprising administering HS/BMP2 to cartilage precursor cells or cartilage stem cells.

The methods of stimulating or inhibiting osteogenesis or formation of cartilage tissue may be conducted in vitro by contacting bone or cartilage precursor or stem cells with HS/BMP2, optionally in the presence of exogenously added BMP2 protein. The precursor cells or stem cells may be mesenchymal stem cells. Where tissue formation is promoted, the tissue formed may be collected and used for implantation into a human or animal patient.

Accordingly, in one aspect of the present invention, connective tissue is provided wherein the connective tissue is obtained by in vitro culture of mesenchymal stem cells in the presence of HS/BMP2 (i.e. exogenous HS/BMP2), and optionally in the presence of BMP2 (i.e. exogenous BMP2). The connective tissue may be bone, cartilage, muscle, fat, ligament or tendon.

The prevention or treatment of disease using HS/BMP2 may involve the repair, regeneration or replacement of tissue, particularly connective tissue such as bone, cartilage, muscle, fat, ligament or tendon.

In patients having a deterioration of one of these tissues, administration of HS/BMP2 to the site of deterioration may be used to stimulate the growth, proliferation and/or differentiation of tissue at that site. For example, stimulation of mesenchymal stem cells present at, or near to, the site of administration may lead, preferably when BMP2 is also present at the site, to the proliferation and differentiation of the mesenchymal stem cells into the appropriate connective tissue, thereby providing for replacement/regeneration of the damaged tissue and treatment of the injury.

Alternatively, connective tissue obtained from in vitro culture of mesenchymal stem cells in contact with HS/BMP2 may be collected and implanted at the site of injury or disease to replace damaged or deteriorated tissue. The damaged or deteriorated tissue may optionally first be excised from the site of injury or disease.

In another aspect, a pharmaceutical composition may be provided containing stem cells, preferably mesenchymal stem cells, and HS/BMP2. Administration, e.g. injection, of the composition at the site of injury, disease or deterioration provides for the regeneration of tissue at the site.

Accordingly, HS/BMP2 is useful in wound healing in vivo, including tissue repair, regeneration and/or replacement (e.g. healing of scar tissue or a broken bone) effected by direct application of HS/BMP2, optionally in combination with BMP2 and/or stem cells, to the patient requiring treatment. HS/BMP2 is also useful in the in vitro generation of tissue suitable for implantation into a patient in need of tissue repair, regeneration and/or replacement.

The following numbered paragraphs (paras.) contain statements of broad combinations of the inventive technical features herein disclosed:

1. A method of isolating glycosaminoglycans capable of binding to a protein having a heparin-binding domain, the method comprising:
   (i) providing a solid support having polypeptide molecules adhered to the support, wherein the polypeptide comprises a heparin-binding domain;
   (ii) contacting the polypeptide molecules with a mixture comprising glycosaminoglycans such that polypeptide-glycosaminoglycan complexes are allowed to form;
   (iii) partitioning polypeptide-glycosaminoglycan complexes from the remainder of the mixture;
   (iv) dissociating glycosaminoglycans from the polypeptide-glycosaminoglycan complexes;
   (v) collecting the dissociated glycosaminoglycans.

2. A method of identifying glycosaminoglycans capable of stimulating or inhibiting the growth and/or differentiation of cells and/or tissues, the method comprising:
   providing a solid support having polypeptide molecules adhered to the support, wherein the polypeptide comprises a heparin-binding domain;
   contacting the polypeptide molecules with a mixture comprising glycosaminoglycans such that polypeptide-glycosaminoglycan complexes are allowed to form;
   partitioning polypeptide-glycosaminoglycan complexes from the remainder of the mixture;
   dissociating glycosaminoglycans from the polypeptide-glycosaminoglycan complexes;
   collecting the dissociated glycosaminoglycans;
   adding the collected glycosaminoglycans to cells or tissues in which a protein containing the amino acid sequence of the heparin-binding domain is present;
   measuring one or more of: proliferation of the cells, differentiation of the cells, expression of one or more protein/glycoprotein/glycolipid markers markers.

3. The method of paragraph 1 or 2 wherein the mixture comprising glycosaminoglycans contains extracellular matrix material.

4. The method of paragraph 3 wherein the extracellular matrix material is derived from connective tissue or connective tissue cells.

5. The method of any one of paragraphs 1 to 4 wherein the mixture comprising glycosaminoglycans contains one or more of a dextran sulphate, a chondroitin sulphate, a heparan sulphate.

6. The method of any one of paragraphs 1 to 5 wherein the mixture comprising glycosaminoglycans has been enriched for one of dextran sulphate, chondroitin sulphate, heparan sulphate.

7. The method of any one of paragraphs 1 to 6 wherein the method further comprises subjecting the collected glycosaminoglycans to further analysis in order to determine structural characteristics of the GAG.

8. The method of any one of paragraphs 1 to 7 wherein the glycosaminoglycan-polypeptide complexes are contacted with a lyase.

9. The method of any one of paragraphs 1 to 8 wherein the polypeptide is, or comprises, one of SEQ ID NO.s: 1 or 2.

10. Heparan sulphate HS/BMP2.

11. Culture media comprising HS/BMP2.

12. A pharmaceutical composition or medicament comprising HS/BMP2.

13. The pharmaceutical composition or medicament of paragraph 12 further comprising a pharmaceutically acceptable carrier, adjuvant or diluent.

14. The pharmaceutical composition or medicament of paragraph 12 or 13 further comprising BMP2 protein.

15. A pharmaceutical compositions or medicament according to any one of paragraphs 12 to 14 for use in the prevention or treatment of injury or disease.

16. Use of HS/BMP2 in the manufacture of a medicament for the prevention or treatment of injury or disease.

17. The pharmaceutical composition or use of paragraph 15 or 16 wherein the prevention or treatment is chosen from: repair, regeneration or replacement of connective tissue and wound healing.

18. A method of preventing or treating injury or disease in a patient in need of treatment thereof, the method comprising administering an effective amount of HS/BMP2 to the patient.

19. The method of paragraph 18 wherein the administered HS/BMP2 is formulated as a pharmaceutical composition or medicament.

20. The method of paragraph 19 wherein the pharmaceutical composition or medicament further comprises BMP2 protein.

21. A method of promoting or inhibiting osteogenesis comprising administering HS/BMP2 to bone precursor cells or bone stem cells.

22. The method of paragraph 21 wherein the bone precursor cells or bone stem cells are contacted with HS/BMP2 in vitro.

23. The method of paragraph 21 wherein the bone precursor cells or bone stem cells are contacted with HS/BMP2 in vivo.

24. The method of any one of paragraphs 21 to 23 wherein the bone precursor cells or bone stem cells are contacted with BMP2 simultaneously with HS/BMP2.

25. A method of promoting or inhibiting the formation of cartilage tissue comprising administering HS/BMP2 to cartilage precursor cells or cartilage stem cells.

26. The method of paragraph 25 wherein the cartilage precursor cells or cartilage stem cells are contacted with HS/BMP2 in vitro.

27. The method of paragraph 25 wherein the cartilage precursor cells or cartilage stem cells are contacted with HS/BMP2 in vivo.

28. The method of any one of paragraphs 25 to 27 wherein the cartilage precursor cells or cartilage stem cells are contacted with BMP2 simultaneously with HS/BMP2.

29. A method for the repair, replacement or regeneration of connective tissue in a human or animal patient in need of such treatment, the method comprising:
(i) culturing mesenchymal stem cells in vitro in contact with HS/BMP2 for a period of time sufficient for said cells to form connective tissue;
(ii) collecting said connective tissue;
(iii) implanting said connective tissue into the body of the patient at a site of injury or disease to repair, replace or regenerate connective tissue in the patient.

30. The method of paragraph 29 further comprising contacting the mesenchymal cells in culture with exogenous BMP2.

31. Connective tissue obtained by in vitro culture of mesenchymal stem cells in the presence of HS/BMP2.

32. Connective tissue as paragraphed in paragraph 31, wherein the mesenchymal cells are cultured in the presence of exogenous BMP2, and optionally in the presence of BMP2.

33. A pharmaceutical composition comprising stem cells and HS/BMP2.

34. The pharmaceutical composition of paragraph 32 wherein the stem cells are mesenchymal stem cells.

35. The pharmaceutical composition of paragraphs 33 or 34 wherein the composition further comprises BMP2.

36. A pharmaceutical composition according to any of paragraphs 33 to 35 for use in the treatment of injury or disease.

37. A method for the treatment of injury or disease in a patient in need of treatment thereof comprising administering to the patient a pharmaceutical composition comprising stem cells and HS/BMP2.

38. The method of paragraph 37 wherein the stem cells are mesenchymal stem cells.

39. The method of paragraph 37 or 38 wherein the method further comprises administering BMP2 to the patient.

40. Use of HS/BMP2 in the growth of connective tissue in vitro.

41. A method for growing connective tissue in vitro comprising culturing mesenchymal stem cells in contact with exogenously added HS/BMP2.

42. A biological implant comprising a solid or semi-solid matrix material impregnated with HS/BMP2.

43. The biological implant of paragraph 42 further impregnated with BMP2.

44. The biological implant of paragraph 42 or 43 further impregnated with mesenchymal stem cells.

45. A kit comprising a predetermined amount of a glycosaminoglycan having high affinity for a protein having a heparin-binding domain and a predetermined amount of said protein.

46. The kit of paragraph 45 wherein the glycosaminoglycan is HS/BMP2 and the protein is BMP2.

DESCRIPTION OF PREFERRED EMBODIMENTS

HS/BMP2

The present invention relates to HS/BMP2, which is obtainable by methods of enriching mixtures of compounds containing one or more GAGs that bind to a polypeptide corresponding to the heparin-binding domain of BMP2. The enrichment process may be used to isolate HS/BMP2.

The present invention also relates to mixtures of compounds enriched with HS/BMP2, and methods of using such mixtures.

HS/BMP2 is believed to potentiate (e.g. agonize) the activity of BMP-2 and hence its ability to stimulate stem cell proliferation and bone formation.

In addition to being obtainable by the methodology described here, HS/BMP2 can also be defined functionally and structurally.

Functionally, HS/BMP2 is capable of binding a peptide having, or consisting of, the amino acid sequence of SEQ ID NO:1 or 6. Preferably, HS/BMP2 binds the peptide of SEQ ID NO:1 or 6 with a $K_D$ of less than 100 µM, more preferably less than one of 50 µM, 40 µM, 30 µM, 20 µM, or 10 µM.

Preferably, HS/BMP2 also binds BMP2 protein with a $K_D$ of less than 100 µM, more preferably less than one of 50 µM, 40 µM, 30 µM, 20 µM, or 10 µM. Binding between HS/BMP2 and BMP2 protein may be determined by the following assay method.

BMP2 is dissolved in Blocking Solution (0.2% gelatin in SAB) at a concentration of 3 µg/ml and a dilution series from 0-3 µg/ml in Blocking Solution is established. Dispensing of 200 µl of each dilution of BMP2 into triplicate wells of Heparin/GAG Binding Plates pre-coated with heparin; incubated for 2 hrs at 37° C., washed carefully three times with SAB and 200 µl of 250 ng/ml biotinylated anti-BMP2 added in Blocking Solution. Incubation for one hour at 37° C., wash carefully three times with SAB, 200 µl of 220 ng/ml ExtrAvidin-AP added in Blocking Solution, Incubation for 30 mins at 37° C., careful washing three times with SAB and tap to remove residual liquid, 200 µl of Development Reagent (SigmaFAST p-Nitrophenyl phosphate) added. Incubate at room temperature for 40 minutes with absorbance reading at 405 nm within one hour.

In this assay, binding may be determined by measuring absorbance and may be determined relative to controls such as BMP2 protein in the absence of added heparan sulphate, or BMP2 protein to which an heparan sulphate is added that does not bind BMP2 protein.

The binding of HS/BMP2 is preferably specific, in contrast to non-specific binding and in the context that the HS/BMP2 can be selected from other heparan sulphates and/or GAGs by a method involving selection of heparan sulphates exhibiting a high affinity binding interaction with the peptide of SEQ ID NO:1 or 6 or with BMP2 protein.

HS/BMP2 according to the present invention preferably enhances BMP2 induced Alkaline Phoshatase (ALP) activity in cells of the mouse myoblast cell line C2C12 to a greater extent than the enhancement obtained by addition of corresponding amounts of BMP2 protein or Heparin alone. Preferably it also enhances BMP2-induced ALP activity in C2C12 cells to a greater extent than that induced by combined addition of corresponding amounts of BMP2 protein and heparin, or of BMP2 protein and a heparan sulphate that does not bind BMP2 protein with high affinity (for example refer to FIG. 46).

Enhancement of ALP activity can be measured by performing the following ALP Assay. C2C12 cells are plated at 20,000 cells/cm² in a 24-well plate in DMEM (e.g. Sigma-Aldrich Inc., St. Louis, Mo.) containing 10% FCS (e.g. Lonza Group Ltd., Switzerland) and antibiotics (1% Penicillin and 1% Streptomycin) (e.g. Sigma-Aldrich Inc., St. Louis, Mo.) at 37° C./5% $CO_2$. After 24 hours, the culture media is switched to 5% FCS low serum media containing different combinations of 100 ng/mL BMP2 (e.g. R&D Systems, Minneapolis, Minn.), 3 mg/mL Celsus HS and varying concentrations of BMP2-specific (+ve HS) and non-specific (-ve HS) Celsus HS preparations. Cell lysis is carried out after 3 days using RIPA buffer containing 1% Triton X-100, 150 mM NaCl, 10 mM Tris pH 7.4, 2 mM EDTA, 0.5% Igepal (NP40), 0.1% Sodium dodecyl sulphate (SDS) and 1% Protease Inhibitor Cocktail Set III (Calbiochem, Germany). The protein content of the cell lysate is determined by using BCA protein assay kit (Pierce Chemical Co., Rockford, Ill.). ALP activity in the cell lysates was then determined by incubating the cell lysates with p-nitrophenylphosphate substrate (Invitrogen, Carlsbad, Calif.). The reading is normalized to total protein amount and presented as relative amount to the group containing BMP2 treatment alone.

Enhancement of ALP activity in C2C12 cells can also be followed by immunohistochemical techniques, such as the following ALP staining protocol, illustrated by FIG. 47. ALP Staining. C2C12 cells are cultured as described in the assay methodology immediately above. After 3 days of treatment, the cell layer is washed in PBS and stained using Leukocyte Alkaline Phosphatase Kit (e.g. Sigma-Aldrich Inc., St. Louis, Mo.) according to manufacturer's specification. The cell layer is fixed in citrate buffered 60% acetone and stained in alkaline-dye mixture containing Naphthol AS-MX Phosphatase Alkaline and diazonium salt. Nuclear staining is performed using Mayer's Hematoxylin solution.

These techniques can be used to identify HS/BMP2 as a heparan sulphate that enhances a greater degree of BMP2 protein induced ALP activity in C2C12 cells compared with non-specific heparan sulphates, e.g. heparan sulphates that do not bind BMP-2 protein.

HS/BMP2 according to the present invention also prolongs the effects of BMP2 signalling to levels that equal or exceed those of heparin. This can be assessed by the following assay. C2C12 cells are exposed to (i) nothing, (ii) BMP2 alone, (iii) BMP2+ Heparin or (iv) BMP2+HS/BMP2 for 72 hours and the phosphorylation levels of the BMP2-specific intracellular signaling molecule Smad1/5/8 are monitored by immunoblotting.

An important functional property of HS/BMP2 is its ability to enhance the process of bone repair, particularly in mammalian subjects. This may be tested in a bone repair model, such as that described in Examples 8 and 9, in which the speed and quality of bone repair in control animals (e.g. animals not given HS or animals given an HS that does not bind BMP2 protein or the peptide of SEQ ID NO:1 or 6) and HS/BMP2 treated animals is compared. Speed and quality of bone repair may be assessed by analysing generation of bone volume at the wound site over time, e.g. by X-ray and microCT imaging analysis of the wound.

Structurally, N-sulfation of N-acetyl-D-glucosamine (GlcNAc) residues in HS/BMP2 has been found to be important as regards maintaining binding affinity for BMP2 protein. N-desulfation was shown to lead to a significant reduction in BMP2 protein binding affinity (FIG. 48).

6-O-sulfation (O-sulphation at C6) of N-sulphoglucosamine (GlcNS) residues was also found to be of moderate significance as regards maintaining binding affinity for BMP2 protein. 6-O-desulfation led to some reduction in BMP2 protein binding affinity (FIG. 48).

2-O-sulfation (O-sulphation at C2) of IdoA and/or D-glucuronic acid (GlcA) residues was found not to affect BMP2 protein binding. As such, HS/BMP2 may optionally be either 2-O-sulfated or 2-O-desulfated.

The disaccharide composition of HS/BMP2 is shown in FIG. 43. HS/BMP2 according to the present invention includes heparan sulphate that has a disaccharide composition within ±10% (more preferably ±one of 9%, 8%, 7%, 6%, 5%, 4%, 3%, 2%, or 1%) of the values shown for each disaccharide in FIG. 43 in the column titled "BMP2-Specific HS" and which exhibits high affinity binding to BMP2 protein or the peptide of SEQ ID NO:1 or 6, as described in this specification.

The structural differences of HS/BMP2 compared with heparan sulphates that do not bind BMP2 protein are also illustrated by conducting surface plasmon resonance analysis. For example, the angle shift curve illustrated in FIG. 44 can be used to distinguish HS/BMP2 from other heparan sulphates.

The structural differences of HS/BMP2 compared with heparan sulphates that do not bind BMP2 protein are further illustrated by conducting strong anion exchange high pressure liquid chromatography (SAX-HPLC). FIG. 40 illustrates the SAX-HPLC spectrum of HS/BMP2, which may be compared with the SAX-HPLC spectra of heparan sulphates that do not bind BMP2 protein (FIGS. 41 and 42).

To identify HS/BMP2 the inventors devised a method that involves enriching for glycosaminoglycan molecules that exhibit binding to particular polypeptides having a heparin-binding domain. Isolated GAG mixtures and/or molecules can then be identified and tested for their ability to modulate the growth and differentiation of cells and tissue expressing a protein containing the heparin-binding domain. This enables the controlled analysis of the effect of particular GAG saccharide sequences on the growth and differentiation of cells and tissue, both in vitro and in vivo. The inventors applied this methodology to Bone Morphogenetic Protein 2 (BMP2) in order to isolate and characterise GAGs having high binding to BMP2.

Accordingly, to identify HS/BMP2 the inventors provided a method of isolating glycosaminoglycans capable of binding to proteins having heparin/heparan-binding domains, the method comprising:

(i) providing a solid support having polypeptide molecules adhered to the support, wherein the polypeptide comprises a heparin-binding domain;

(ii) contacting the polypeptide molecules with a mixture comprising glycosaminoglycans such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes;

(v) collecting the dissociated glycosaminoglycans.

The inventors also provided isolated glycosaminoglycans identified by their ability to modulate the growth or differentiation of cells or tissues. To do this, they provided a method of identifying glycosaminoglycans capable of stimulating or inhibiting the growth and/or differentiation of cells and/or tissues, the method comprising:

(i) providing a solid support having polypeptide molecules adhered to the support, wherein the polypeptide comprises a heparin-binding domain;

(ii) contacting the polypeptide molecules with a mixture comprising glycosaminoglycans such that polypeptide-glycosaminoglycan complexes are allowed to form;

(iii) partitioning polypeptide-glycosaminoglycan complexes from the remainder of the mixture;

(iv) dissociating glycosaminoglycans from the polypeptide-glycosaminoglycan complexes;

(v) collecting the dissociated glycosaminoglycans;

(vi) adding the collected glycosaminoglycans to cells or tissues in which a protein containing the amino acid sequence of the heparin-binding domain is present;

(vii) measuring one or more of: proliferation of the cells, differentiation of the cells, expression of one or more protein markers.

The inventors used these methods to identify a GAG capable of binding to BMP2 (which they called HS/BMP2 or HS3 or HS-3), wherein the polypeptide used in the inventors' methodology comprised the heparin-binding domain of SEQ ID NO:1 or 6, derived from the amino acid sequence of BMP2.

In the inventors' methodology, the mixture comprising GAGs may contain synthetic glycosaminoglycans. However, GAGs obtained from cells or tissues are preferred. For example, the mixture may contain extracellular matrix wherein the extracellular matrix material is obtained by scraping live tissue in situ (i.e. directly from the tissue in the body of the human or animal from which it is obtained) or by scraping tissue (live or dead) that has been extracted from the body of the human or animal. Alternatively, the extracellular matrix material may be obtained from cells grown in culture. The extracellular matrix material may be obtained from connective tissue or connective tissue cells, e.g. bone, cartilage, muscle, fat, ligament or tendon. For isolation of HS/BMP2 one suitable source of extracellular matrix material are osteoblasts, such as mouse MC3T3 cells.

The GAG component may be extracted from a tissue or cell sample or extract by a series of routine separation steps (e.g. anion exchange chromatography), well known to those of skill in the art.

GAG mixtures may contain a mixture of different types of glycosaminoglycan, which may include dextran sulphates, chondroitin sulphates and heparan sulphates. Preferably, the GAG mixture contacted with the solid support is enriched for heparan sulphate. A heparan sulphate-enriched GAG fraction may be obtained by performing column chromatography on the GAG mixture, e.g. weak, medium or strong anion exchange chromatography, as well as strong high pressure liquid chromatography (SAX-HPLC), with selection of the appropriate fraction.

The collected GAGs may be subjected to further analysis in order to identify the GAG, e.g. determine GAG composition or sequence, or determine structural characteristics of the GAG. GAG structure is typically highly complex, and, taking account of currently available analytical techniques, exact determinations of GAG sequence structure are not possible in most cases.

However, the collected GAG molecules may be subjected to partial or complete saccharide digestion (e.g. chemically by nitrous acid or enzymatically with lyases such as heparinase III) to yield saccharide fragments that are both characteristic and diagnostic of the GAG. In particular, digestion to yield disaccharides (or tetrasaccharides) may be used to measure the percentage of each disaccharide obtained which will provide a characteristic disaccharide "fingerprint" of the GAG.

The pattern of sulphation of the GAG can also be determined and used to determine GAG structure. For example, for heparan sulphate the pattern of sulphation at amino sugars and at the C2, C3 and C6 positions may be used to characterise the heparan sulphate.

Disaccharide analysis, tetrasaccharide analysis and analysis of sulphation can be used in conjunction with other analytical techniques such as HPLC, mass spectrometry and NMR which can each provide unique spectra for the GAG. In combination, these techniques may provide a definitive structural characterisation of the GAG.

A high affinity binding interaction between the GAG and heparin-binding domain indicates that the GAG will contain a specific saccharide sequence that contributes to the high affinity binding interaction. A further step may comprise determination of the complete or partial saccharide sequence of the GAG, or the key portion of the GAG, involved in the binding interaction.

GAG-polypeptide complexes may be subjected to treatment with an agent that lyses glycosaminoglycan chains, e.g. a lyase. Lyase treatment may cleave portions of the bound GAG that are not taking part in the binding interaction with the polypeptide. Portions of the GAG that are taking part in the binding interaction with the polypeptide may be protected from lyase action. After removal of the lyase, e.g. following a washing step, the GAG molecule that remains bound to the polypeptide represents the specific binding partner ("GAG ligand") of the polypeptide. Owing to the lower complexity of shorter GAG molecules, following dissociation and collection of the GAG ligand, a higher degree of structural characterisation of the GAG ligand can be expected. For example, the combination of any of the saccharide sequence (i.e. the primary (linear) sequence of monosaccharides contained in the GAG ligand), sulphation pattern, disaccharide and/or tetrasaccharide digestion analysis, NMR spectra, mass spectrometry spectra and HPLC spectra may provide a high level of structural characterisation of the GAG ligand.

As used herein, the terms 'enriching', 'enrichment', 'enriched', etc. describes a process (or state) whereby the relative composition of a mixture is (or has been) altered in such a way that the fraction of that mixture given by one or more of those entities is increased, while the fraction of that mixture given by one or more different entities is decreased.

GAGs isolated by enrichment may be pure, i.e. contain substantially only one type of GAG, or may continue to be a mixture of different types of GAG, the mixture having a higher proportion of particular GAGs that bind to the heparin-binding domain relative to the starting mixture.

The GAGs identified preferably exhibit a functional effect when contacted with cells or tissue in which a protein containing the heparin-binding domain is expressed or contained. The functional effect may be a modulating or potentiating effect.

The functional effect may be to promote (stimulate) or inhibit the proliferation of the cells of a certain type or the differentiation of one cell type into another, or the expression of one or more protein markers. For example, the GAGs may promote cell proliferation, i.e. an increase in cell number, or promote differentiation of stem cells into specialised cell types (e.g. mesenchymal stem cells in connective tissue), promote or inhibit the expression of protein markers indicative of the multipotency or differentiation state of the cells (e.g. markers such as alkaline phosphatase activity, detection of RUNX2, osterix, collagen I, II, IV, VII, X, osteopontin, Osteocalcin, BSPII, SOX9, Aggrecan, ALBP, CCAAT/enhancer binding protein-α (C/EBPα), adipocyte lipid binding protein (ALBP), alkaline phosphatase (ALP), bone sialoprotein 2, (BSPII), Collagen2a1 (Coll2a) and SOX9).

As used herein, the term 'modulating effect' is understood to mean the effect that a first entity has on a second entity wherein the second entity's normal function in another process or processes is modified by the presence of the first entity. The modulating effect may be either agonistic or antagonistic.

The modulating effect may be a potentiating effect. The term 'potentiating effect' is understood to mean the effect of increasing potency. In a preferred embodiment of the present invention, the term 'potentiating effect' refers to the effect that a first entity has on a second entity, which effect increases the potency of that second entity in another process or processes. In a further preferred embodiment of the present invention, the potentiating effect is understood to mean the effect of isolated GAGs on a heparin-binding factor, wherein the said effect increases the potency of said heparin-binding factor.

The potentiating effect may be an increase in bioavailability of the heparin-binding factor. In a preferred embodiment of the present invention, the potentiating effect is an increase in bioavailability of BMP2. One method of measuring an increase in bioavailability of the heparin-binding factor is through determining an increase in local concentration of the heparin-binding factor.

The potentiating effect may be to protect the heparin-binding factor from degradation. In an especially preferred embodiment of the present invention, the potentiating effect is to protect BMP-2 from degradation. One method of determining a decrease in the degradation of the heparin-binding factor is through measuring an increase in the half-life of the heparin-binding factor.

The potentiating effect may be to sequester heparin-binding factors away from cellular receptors or may be to stabilise the ligand-receptor interaction.

The potentiating effect (e.g. modulation of growth or differentiation) may be determined by use of appropriate assays. For example, the effect that an HS has on the stability of BMP-2 may be determined by ELISA. The effect that an HS has on the activity of BMP-2 may be determined by measuring the activation/expression of one or more of SMAD 1, 5 or 8, or measuring the expression of one or more osteogenic marker genes such as Runx2, alkaline phosphatase, Osterix, Osteocalcin and BSP1, or measuring the levels of mineralization using staining such as Alizarin Red and von Kossa.

As used herein, the process of 'contacting' involves the bringing into close physical proximity of two or more discrete entities. The process of 'contacting' involves the bringing into close proximity of two or more discrete entities for a time, and under conditions, sufficient to allow a portion of those two or more discrete entities to interact on a molecular level. Preferably, as used herein, the process of 'contacting' involves the bringing into close proximity of the mixture of compounds possessing one or more GAGs and the polypeptide corresponding to the heparin-binding domain of a heparin-binding factor. Examples of 'contacting' processes include mixing, dissolving, swelling, washing. In preferred embodiments 'contact' of the GAG mixture and polypeptide is sufficient for complexes, which may be covalent but are preferably non-covalent, to form between GAGs and polypeptides that exhibit high affinity for each other.

The polypeptide may comprise the full length or near full length primary amino acid sequence of a selected protein having a heparin-binding domain. Due to folding that may occur in longer polypeptides leading to possible masking of the heparin-binding domain from the GAG mixture, it is preferred for the polypeptide to be short. Preferably, the polypeptide will have an amino acid sequence that includes the heparin-binding domain and optionally including one or more amino acids at one or each of the N- and C-terminals of the peptides. These additional amino acids may enable the addition of linker or attachment molecules to the polypeptide that are required to attach the polypeptide to the solid support.

In preferred embodiments of the inventors' methodology, in addition to the number of amino acids in the heparin-binding domain the polypeptide contains 1-20, more preferably 1-10, still more preferably 1-5 additional amino acids. In some embodiments the amino acid sequence of the heparin-binding domain accounts for at least 80% of the amino acids of the polypeptide, more preferably at least 90%, still more preferably at least 95%.

In order to adhere polypeptides to the surface of a solid support the polypeptides are preferably modified to include a molecular tag, and the surface of the solid support is modified to incorporate a corresponding molecular probe having high affinity for the molecular tag, i.e. the molecular tag and probe form a binding pair. The tag and/or probe may be chosen from any one of: an antibody, a cell receptor, a ligand, biotin, any fragment or derivative of these structures, any combination of the foregoing, or any other structure with which a probe can be designed or configured to bind or otherwise associate with specificity. A preferred binding pair suitable for use as tag and probe is biotin and avidin.

The polypeptide is derived from the protein of interest, which in the present case is BMP2. By "derived from" is meant that the polypeptide is chosen, selected or prepared because it contains the amino acid sequence of a heparin-binding domain that is present in the protein of interest. The amino acid sequence of the heparin-binding domain may be modified from that appearing in the protein of interest, e.g. to investigate the effect of changes in the heparin-binding domain sequence on GAG binding.

In this specification the protein is BMP2. The amino acid sequence of the preferred heparin-binding domain from BMP2 is QAKHKQRKRLKSSCKRHP (SEQ ID NO:1), which is found at amino acids 283-300 of SEQ ID NO:2 (FIG. 35) or QAKHKQRKRLKSSCKRH (SEQ ID NO:6) which is found at amino acids 283-299 of SEQ ID NO:2.

It is understood by those skilled in the art that small variations in the amino acid sequence of a particular polypeptide may allow the inherent functionality of that portion to be maintained. It is also understood that the substitution of certain amino acid residues within a peptide with other amino acid residues that are isosteric and/or isoelectronic may either maintain or improve certain properties of the unsubstituted peptide. These variations are also encompassed within the scope of the present invention. For example, the amino acid alanine may sometimes be substituted for the amino acid glycine (and vice versa) whilst maintaining one or more of the properties of the peptide. The term 'isosteric' refers to a spatial similarity between two entities.

Two examples of moieties that are isosteric at moderately elevated temperatures are the iso-propyl and tert-butyl groups. The term 'isoelectronic' refers to an electronic similarity between two entities, an example being the case where two entities possess a functionality of the same, or similar, pKa.

The polypeptide corresponding to the heparin-binding domain may be synthetic or recombinant.

The solid support may be any substrate having a surface to which molecules may be attached, directly or indirectly, through either covalent or non-covalent bonds. The solid support may include any substrate material that is capable of providing physical support for the probes that are attached to the surface. It may be a matrix support. The material is generally capable of enduring conditions related to the attachment of the probes to the surface and any subsequent treatment, handling, or processing encountered during the performance of an assay. The materials may be naturally occurring, synthetic, or a modification of a naturally occurring material. The solid support may be a plastics material (including polymers such as, e.g., poly(vinyl chloride), cyclo-olefin copolymers, polyacrylamide, polyacrylate, polyethylene, polypropylene, poly(4-methylbutene), polystyrene, polymethacrylate, poly(ethylene terephthalate), polytetrafluoroethylene (PTFE or Teflon®), nylon, poly(vinyl butyrate)), etc., either used by themselves or in conjunction with other materials. Additional rigid materials may be considered, such as glass, which includes silica and further includes, for example, glass that is available as Bioglass. Other materials that may be employed include porous materials, such as, for example, controlled pore glass beads. Any other materials known in the art that are capable of having one or more functional groups, such as any of an amino, carboxyl, thiol, or hydroxyl functional group, for example, incorporated on its surface, are also contemplated.

Preferred solid supports include columns having a polypeptide immobilized on a surface of the column. The surface may be a wall of the column, and/or may be provided by beads packed into the central space of the column.

The polypeptide may be immobilised on the solid support. Examples of methods of immobilisation include: adsorption, covalent binding, entrapment and membrane confinement. In a preferred embodiment of the present invention the interaction between the polypeptide and the matrix is substantially permanent. In a further preferred embodiment of the present invention, the interaction between the peptide and the matrix is suitably inert to ion-exchange chromatography. In a preferred arrangement, the polypeptide is attached to the surface of the solid support. It is understood that a person skilled in the art would have a large array of options to choose from to chemically and/or physically attach two entities to each other. These options are all encompassed within the scope of the present invention. In a preferred arrangement, the polypeptide is adsorbed to a solid support through the interaction of biotin with streptavidin. In a representative example of this arrangement, a molecule of biotin is bonded covalently to the polypeptide, whereupon the biotin-polypeptide conjugate binds to streptavidin, which in turn has been covalently bonded to a solid support. In another arrangement, a spacer or linker moiety may be used to connect the molecule of biotin with the polypeptide, and/or the streptavidin with the matrix.

By contacting the GAG mixture with the solid support GAG-polypeptide complexes are allowed to form. These are partitioned from the remainder of the mixture by removing the remainder of the mixture from the solid support, e.g. by washing the solid support to elute non-bound materials. Where a column is used as the solid support non-binding components of the GAG mixture can be eluted from the column leaving the GAG-polypeptide complexes bound to the column.

It is understood that certain oligosaccharides may interact in a non-specific manner with the polypeptide. In certain embodiments, oligosaccharide which interacts with the polypeptide in a non-specific manner may be included in, or excluded from the mixture of compounds enriched with one or more GAGs that modulate the effect of a heparin-binding factor. An example of a non-specific interaction is the temporary confinement within a pocket of a suitably sized and/or shaped molecule. Further it is understood that these oligosaccharides may elute more slowly than those oligosaccharides that display no interaction with the peptide at all. Furthermore it is understood that the compounds that bind non-specifically may not require the input of the same external stimulus to make them elute as for those compounds that bind in a specific manner (for example through an ionic interaction). The inventors' methodology is capable of separating a mixture of oligosaccharides into those components of that mixture that: bind in a specific manner to the polypeptide; those that bind in a non-specific manner to the polypeptide; and those that do not bind to the polypeptide. These designations are defined operationally for each GAG-peptide pair.

By varying the conditions (e.g. salt concentration) present at the surface of the solid support where binding of the GAG and polypeptide occurs those GAGs having the highest affinity and/or specificity for the heparin-binding domain can be selected.

GAGs may accordingly be obtained that have a high binding affinity for a protein of interest and/or the heparin-binding domain of the protein of interest. The binding affinity ($K_d$) may be chosen from one of: less than 10 µM, less than 1 µM, less than 100 nM, less than 10 nM, less than 1 nM, less than 100 pM.

GAGs obtained by the methods described may be useful in a range of applications, in vitro and/or in vivo. The GAGs may be provided for use in stimulation or inhibition of cell or tissue growth and/or proliferation and/or differentiation either in cell or tissue culture in vitro, or in cells or tissue in vivo.

The GAGs may be provided as a formulation for such purposes. For example, culture media may be provided comprising a GAG obtained by the method described, i.e. comprising HS/BMP2.

Cells or tissues obtained from in vitro cell or tissue culture in the presence of HS/BMP2 may be collected and implanted into a human or animal patient in need of treatment. A method of implantation of cells and/or tissues may therefore be provided, the method comprising the steps of:

(a) culturing cells and/or tissues in vitro in contact with HS/BMP2;

(b) collecting the cells and/or tissues;

(c) implanting the cells and/or tissues into a human or animal subject in need of treatment.

The cells may be cultured in part (a) in contact with HS/BMP2 for a period of time sufficient to allow growth, proliferation or differentiation of the cells or tissues. For example, the period of time may be chosen from: at least 5 days, at least 10 days, at least 20 days, at least 30 days or at least 40 days.

In another embodiment the HS/BMP2 may be formulated for use in a method of medical treatment, including the prevention or treatment of injury or disease. A pharmaceutical composition or medicament may be provided comprising HS/BMP2 and a pharmaceutically acceptable diluent, carrier or adjuvant. Such pharmaceutical compositions or medicaments may be provided for the prevention or treatment of injury or disease. The use of HS/BMP2 in the manufacture of a medicament for the prevention or treatment of injury or disease is also provided. Optionally, pharmaceutical compositions and medicaments according to the present invention may also contain the protein of interest (i.e. BMP2) having the heparin-binding domain to which the GAG binds. In further embodiments the pharmaceutical compositions and medicaments may further comprise stem cells, e.g. mesenchymal stem cells.

Treatment of injury or disease may comprise the repair, regeneration or replacement of cells or tissue, such as connective tissue (e.g. bone, cartilage, muscle, fat, tendon or ligament). For the repair of tissue, the pharmaceutical composition or medicament comprising HS/BMP2 may be administered directly to the site of injury or disease in order to stimulate the growth, proliferation and/or differentiation of new tissue to effect a repair of the injury or to cure or alleviate (e.g. provide relief to the symptoms of) the disease condition. The repair or regeneration of the tissue may be improved by combining stem cells in the pharmaceutical composition or medicament.

For the replacement of tissue, HS/BMP2 may be contacted with cells and/or tissue during in vitro culture of the cells and/or tissue in order to generate cells and/or tissue for implantation at the site of injury or disease in the patient. Implantation of cells or tissue can be used to effect a repair of the injured or diseased tissue in the patient by replacement of the injured or diseased tissue. This may involve excision of injured/diseased tissue and implantation of new tissue prepared by culture of cells and/or tissue in contact with HS/BMP2.

Pharmaceutical compositions and medicaments according to the present invention may therefore comprise one of:

(a) HS/BMP2;
(b) HS/BMP2 in combination with stem cells;
(c) HS/BMP2 in combination with a protein containing the heparin-binding domain bound by HS/BMP2 (i.e. SEQ ID NO:1 or 6);
(d) HS/BMP2 in combination with stem cells and a protein containing the heparin-binding domain bound by HS/BMP2 (i.e. SEQ ID NO:1 or 6);
(e) Tissues or cells obtained from culture of cells or tissues in contact with HS/BMP2.

HS/BMP2 may be used in the repair or regeneration of bodily tissue, especially bone regeneration, neural regeneration, skeletal tissue construction, the repair of cardio-vascular injuries and the expansion and self-renewal of embryonic and adult stem cells. Accordingly, HS/BMP2 may be used to prevent or treat a wide range of diseases and injuries, including osteoarthritis, cartilage replacement, broken bones of any kind (e.g. spinal disc fusion treatments, long bone breaks, cranial defects), critical or non-union bone defect regeneration.

The use of HS/BMP2 in the repair, regeneration or replacement of tissue may involve use in wound healing, e.g. acceleration of wound healing, healing of scar or bone tissue and tissue grafting.

In another aspect, the present invention provides a biological scaffold comprising HS/BMP2. In some embodiments, the biological scaffolds of the present invention may be used in orthopaedic, vascular, prosthetic, skin and corneal applications. The biological scaffolds provided by the present invention include extended-release drug delivery devices, tissue valves, tissue valve leaflets, drug-eluting stents, vascular grafts, wound healing or skin grafts and orthopaedic prostheses such as bone, ligament, tendon, cartilage and muscle. In a preferred embodiment of the present invention, the biological scaffold is a catheter wherein the inner (and/or outer) surface comprises one or more GAG compounds (including HS/BMP2) attached to the catheter.

In another aspect, the present invention provides one or more GAGs (including HS/BMP2) isolated by the method described for use as an adjuvant. The adjuvant may be an immune adjuvant.

In another aspect, the present invention provides pharmaceutically acceptable formulations comprising a mixture of compounds comprising one or more GAGs, said mixture being enriched with respect to HS/BMP2. In another aspect, the invention provides pharmaceutically acceptable formulations comprising:

(i) a mixture of compounds comprising one or more GAGs, said mixture being enriched with respect to HS/BMP2; and (ii) BMP-2, for separate, simultaneous or sequential administration. In a preferred embodiment the formulation comprises the mixture of compounds comprising one or more GAGs, said mixture being enriched with respect to HS/BMP2 and BMP-2 in intimate admixture, and is administered simultaneously to a patient in need of treatment.

In another aspect of the present invention a kit is provided for use in the repair, or regeneration of tissue, said kit comprising (i) a predetermined amount of HS/BMP2, and (ii) a predetermined amount of BMP2.

The compounds of the enriched mixtures of the present invention can be administered to a subject as a pharmaceutically acceptable salt thereof. For example, base salts of the compounds of the enriched mixtures of the present invention include, but are not limited to, those formed with pharmaceutically acceptable cations, such as sodium, potassium, lithium, calcium, magnesium, ammonium and alkylammonium. The present invention includes within its scope cationic salts, for example the sodium or potassium salts.

It will be appreciated that the compounds of the enriched mixtures of the present invention which bear a carboxylic acid group may be delivered in the form of an administrable prodrug, wherein the acid moiety is esterified (to have the form —$CO_2R'$). The term "pro-drug" specifically relates to the conversion of the —OR' group to a —OH group, or carboxylate anion therefrom, in vivo. Accordingly, the prodrugs of the present invention may act to enhance drug adsorption and/or drug delivery into cells. The in vivo conversion of the prodrug may be facilitated either by cellular enzymes such as lipases and esterases or by chemical cleavage such as in vivo ester hydrolysis.

Medicaments and pharmaceutical compositions according to aspects of the present invention may be formulated for administration by a number of routes, including but not limited to, injection at the site of disease or injury. The medicaments and compositions may be formulated in fluid or solid form. Fluid formulations may be formulated for administration by injection to a selected region of the human or animal body.

Administration is preferably in a "therapeutically effective amount", this being sufficient to show benefit to the individual. The actual amount administered, and rate and time-course of administration, will depend on the nature and severity of the injury or disease being treated. Prescription of treatment, e.g. decisions on dosage etc, is within the responsibility of general practitioners and other medical doctors, and typically takes account of the disorder to be treated, the condition of the individual patient, the site of delivery, the method of administration and other factors known to practitioners. Examples of the techniques and protocols mentioned above can be found in Remington's Pharmaceutical Sciences, 20th Edition, 2000, pub. Lippincott, Williams & Wilkins.

In this specification a patient to be treated may be any animal or human. The patient may be a non-human mammal, but is more preferably a human patient. The patient may be male or female.

Methods according to the present invention may be performed in vitro or in vivo, as indicated. The term "in vitro" is intended to encompass procedures with cells in culture whereas the term "in vivo" is intended to encompass procedures with intact multi-cellular organisms.

Stem Cells

Cells contacted with HS/BMP2 include stem cells.

The stem cells cultured and described herein may be stem cells of any kind. They may be totipotent or multipotent (pluripotent). They may be embryonic or adult stem cells from any tissue and may be hematopoietic stem cells, neural stem cells or mesenchymal stem cells. Preferably they are adult stem cells. More preferably they are adult mesenchymal stem cells, e.g. capable of differentiation into connective tissue and/or bone cells such as chondrocytes, osteoblasts, myocytes and adipocytes. The stem cells may be obtained from any animal or human, e.g. non-human animals, e.g. rabbit, guinea pig, rat, mouse or other rodent (including cells from any animal in the order Rodentia), cat, dog, pig, sheep, goat, cattle, horse, non-human primate or other non-human vertebrate organism; and/or non-human mammalian animals; and/or human. Optionally they are non-human.

In this specification, by stem cell is meant any cell type that has the ability to divide (i.e. self-renew) and remain totipotent or multipotent (pluripotent) and give rise to specialized cells if so desired.

Stem cells cultured in the present invention may be obtained or derived from existing cultures or directly from any adult, embryonic or fetal tissue, including blood, bone marrow, skin, epithelia or umbilical cord (a tissue that is normally discarded).

The multipotency of stem cells may be determined by use of suitable assays. Such assays may comprise detecting one or more markers of pluripotency, e.g. alkaline phosphatase activity, detection of RUNX2, osterix, collagen I, II, IV, VII, X, osteopontin, Osteocalcin, BSPII, SOX9, Aggrecan, ALBP, CCAAT/enhancer binding protein-α (C/EBPα), adipocyte lipid binding protein (ALBP), alkaline phosphatase (ALP), bone sialoprotein 2, (BSPII), Collagen2a1 (Coll2a) and SOX9.

Mesenchymal stem cells or human bone marrow stromal stem cells are defined as pluripotent (multipotent) progenitor cells with the ability to generate cartilage, bone, muscle, tendon, ligament and fat. These primitive progenitors exist postnatally and exhibit stem cell characteristics, namely low incidence and extensive renewal potential. These properties in combination with their developmental plasticity have generated tremendous interest in the potential use of mesenchymal stem cells to replace damaged tissues. In essence mesenchymal stem cells could be cultured to expand their numbers then transplanted to the injured site or after seeding in/on scaffolds to generate appropriate tissue constructs.

Thus, an alternative approach for skeletal, muscular, tendon and ligament repair is the selection, expansion and modulation of the appropriate progenitor cells such as osteoprogenitor cells in the case of bone in combination with a conductive or inductive scaffolds to support and guide regeneration together with judicious selection of specific tissue growth factors.

Human bone marrow mesenchymal stem cells can be isolated and detected using selective markers, such as STRO-I, from a CD34+ fraction indicating their potential for marrow repopulation. These cell surface markers are only found on the cell surface of mesenchymal stem cells and are an indication of the cells pluripotency.

Mesenchymal cells are easily obtainable from bone marrow by minimally invasive techniques and can be expanded in culture and permitted to differentiate into the desired lineage. Differentiation can be induced by the application of specific growth factors. The transforming growth factor beta (TGF-beta) superfamily member proteins such as the bone morphogenetic proteins (BMPs) are important factors of chondrogenic and osteogenic differentiation of mesenchymal stem cells.

Suitable MSCs may be obtained or derived from bone marrow mononuclear cells (BMMNCs) collected from aspirates of bone marrow (e.g. Wexler et al. Adult bone marrow is a rich source of human mesenchymal 'stem' cells but umbilical cord and mobilized adult blood are not. HAEMOPOIESIS AND LEUCOCYTES British Journal of Haematology 121(2):368-374, April 2003.) or Wharton's Jelly of the umbilical cord (e.g. Ta et al. Long-term Expansion and Pluripotent Marker Array Analysis of Wharton's Jelly-Derived Mesenchymal Stem Cells. Stem Cells Dev. 2009 Jul. 20 (Epub)).

Mesenchymal stem cells may be obtained by differentiation of pluripotent stem cells, such as human embryonic stem cells or induced pluripotent stem cells, by application of suitable differentiating factors, as is well known in the art.

In yet a further aspect of the present invention, a pharmaceutical composition comprising stem cells generated by any of the methods of the present invention, or fragments or products thereof, is provided. The pharmaceutical composition useful in a method of medical treatment. Suitable pharmaceutical compositions may further comprise a pharmaceutically acceptable carrier, adjuvant or diluent.

In another aspect of the present invention, stem cells generated by any of the methods of the present invention may be used in a method of medical treatment, preferably, a method of medical treatment is provided comprising administering to an individual in need of treatment a therapeutically effective amount of said medicament or pharmaceutical composition.

Stem cells obtained through culture methods and techniques according to this invention may be used to differentiate into another cell type for use in a method of medical treatment. Thus, the differentiated cell type may be derived from, and may be considered as a product of, a stem cell obtained by the culture methods and techniques described which has subsequently been permitted to differentiate. Pharmaceutical compositions may be provided comprising such differentiated cells, optionally together with a pharmaceutically acceptable carrier, adjuvant or diluent. Such pharmaceutical composition may be useful in a method of medical treatment.

Glycosaminglycans

As used herein, the terms 'glycosaminoglycan' and 'GAG' are used interchangeably and are understood to refer to the large collection of molecules comprising an oligosaccharide, wherein one or more of those conjoined saccharides possess an amino substituent, or a derivative thereof. Examples of GAGs are chondroitin sulfate, keratan sulfate, heparin, dermatan sulfate, hyaluronate and heparan sulfate. Heparan sulfates are preferred embodiments of the present invention.

As used herein, the term 'GAG' also extends to encompass those molecules that are GAG conjugates. An example of a GAG conjugate is a proteoglycosaminoglycan (PGAG, proteoglycan) wherein a peptidic component is covalently bound to an oligosaccharide component.

In the present invention, it is understood that there are a large number of sources of GAG compounds including natural, synthetic or semi-synthetic. A preferred source of GAGs is biological tissue. A preferred source of GAGs is a stem cell. An especially preferred source of GAGs is a stem cell capable of differentiating into a cell that corresponds to a tissue that will be the subject of treatment. For example, GAGs can be sourced from preosteoblasts for use in bone regeneration or skeletal tissue construction. In an especially preferred embodiment of the present invention, GAGs may be sourced from an immortalised cell line. In a further preferred embodiment of the present invention, GAGs may be sourced from an immortalised cell line which is grown in a bioreactor. Another preferred source of GAGs is a synthetic source. In this respect, GAGs may be obtained from the synthetic elaboration of commercially available starting materials into more complicated chemical form through techniques known, or conceivable, to one skilled in the art. An example of such a commercially available starting material is glucosamine. Another preferred source of GAGs is a semi-synthetic source. In this respect, synthetic elaboration of a natural starting material, which possesses much of the complexity of the desired material, is elaborated synthetically using techniques known, or conceivable, to one skilled in the art. Examples of such a natural starting material are chitin and dextran, and examples of the types of synthetic steps that may elaborate that starting material, into a GAG mixture suitable for use in the present invention, are amide bond hydrolysis, oxidation and sulfation. Another example of a semi-synthetic route to GAGs of the desired structure comprises the synthetic interconversion of related GAGs to obtain GAGs suitable for use in the present invention.

Heparan Sulphate (HS)

In preferred aspects of the invention the glycosaminoglycan or proteoglycan is preferably a heparan sulfate.

Heparan sulfate proteoglycans (HSPGs) represent a highly diverse subgroup of proteoglycans and are composed of heparan sulfate glycosaminoglycan side chains covalently attached to a protein backbone. The core protein exists in three major forms: a secreted form known as perlecan, a form anchored in the plasma membrane known as glypican, and a transmembrane form known as syndecan. They are ubiquitous constituents of mammalian cell surfaces and most extracellular matrices. There are other proteins such as agrin, or the amyloid precursor protein, in which an HS chain may be attached to less commonly found cores.

"Heparan Sulphate" ("Heparan sulfate" or "HS") is initially synthesised in the Golgi apparatus as polysaccharides consisting of tandem repeats of D-glucuronic acid (GlcA) and N-acetyl-D-glucosamine (GlcNAc). The nascent polysaccharides may be subsequently modified in a series of steps: N-deacetylation/N-sulfation of GlcNAc, C5 epimerisation of GlcA to iduronic acid (IdoA), O-sulphation at C2 of IdoA and GlcA, O-sulphation at C6 of N-sulphoglucosamine (GlcNS) and occasional O-sulphation at C3 of GlcNS. N-deacetylation/N-sulphation, 2-O-, 6-O- and 3-O-sulphation of HS are mediated by the specific action of HS N-deacetylase/N-sulfotransferase (HSNDST), HS 2-O-sulfotransferase (HS2ST), HS 6-O-sulfotransferase (HS6ST) and HS 3-O-sulfotransferase, respectively. At each of the modification steps, only a fraction of the potential substrates are modified, resulting in considerable sequence diversity. This structural complexity of HS has made it difficult to determine its sequence and to understand the relationship between HS structure and function.

Heparan sulfate side chains consist of alternately arranged D-glucuronic acid or L-iduronic acid and D-glucosamine, linked via (1→4) glycosidic bonds. The glucosamine is often N-acetylated or N-sulfated and both the uronic acid and the glucosamine may be additionally O-sulfated. The specificity of a particular HSPG for a particular binding partner is created by the specific pattern of carboxyl, acetyl and sulfate groups attached to the glucosamine and the uronic acid. In contrast to heparin, heparan sulfate contains less N- and O-sulfate groups and more N-acetyl groups. The heparan sulfate side chains are linked to a serine residue of the core protein through a tetrasaccharide linkage (-glucuronosyl-β-(1→3)-galactosyl-β-(1→3)-galactosyl-β-(1→4)-xylosyl-β-1-O-(Serine)) region.

Both heparan sulfate chains and core protein may undergo a series of modifications that may ultimately influence their biological activity. Complexity of HS has been considered to surpass that of nucleic acids (Lindahl et al, 1998, J. Biol. Chem. 273, 24979; Sugahara and Kitagawa, 2000, Curr. Opin. Struct. Biol. 10, 518). Variation in HS species arises from the synthesis of non-random, highly sulfated sequences of sugar residues which are separated by unsulfated regions of disaccharides containing N-acetylated glucosamine. The initial conversion of N-acetylglucosamine to N-sulfoglucosamine creates a focus for other modifications, including epimerization of glucuronic acid to iduronic acid and a complex pattern of O-sulfations on glucosamine or iduronic acids. In addition, within the non-modified, low sulfated, N-acetylated sequences, the hexuronate residues remain as glucuronate, whereas in the highly sulfated N-sulfated regions, the C-5 epimer iduronate predominates. This limits the number of potential disaccharide variants possible in any given chain but not the abundance of each. Most modifications occur in the N-sulfated domains, or directly adjacent to them, so that in the mature chain there are regions of high sulfation separated by domains of low sulfation (Brickman et al. (1998), J. Biol. Chem. 273(8), 4350-4359, which is herein incorporated by reference in its entirety).

It is hypothesized that the highly variable heparan sulfate chains play key roles in the modulation of the action of a large number of extracellular ligands, including regulation and presentation of growth and adhesion factors to the cell, via a complicated combination of autocrine, juxtacrine and paracrine feedback loops, so controlling intracellular signaling and thereby the differentiation of stem cells. For example, even though heparan sulfate glycosaminoglycans may be genetically described (Alberts et al. (1989) Garland Publishing, Inc, New York & London, pp. 804 and 805), heparan sulfate glycosaminoglycan species isolated from a single source may differ in biological activity. As shown in Brickman et al, 1998, Glycobiology 8, 463, two separate pools of heparan sulfate glycosaminoglycans obtained from neuroepithelial cells could specifically activate either FGF-1 or FGF-2, depending on mitogenic status. Similarly, the capability of a heparan sulfate (HS) to interact with either FGF-1 or FGF-2 is described in WO 96/23003. According to this patent application, a respective HS capable of interacting with FGF-1 is obtainable from murine cells at embryonic day from about 11 to about 13, whereas a HS capable of interacting with FGF-2 is obtainable at embryonic day from about 8 to about 10.

As stated above HS structure is highly complex and variable between HS. Indeed, the variation in HS structure is considered to play an important part in contributing toward the different activity of each HS in promoting cell growth and directing cell differentiation. The structural complexity is considered to surpass that of nucleic acids and although HS structure may be characterised as a sequence of repeating disaccharide units having specific and unique sulfation patterns at the present time no standard sequencing technique equivalent to those available for nucleic acid sequencing is available for determining HS sequence structure. In the absence of simple methods for determining a definitive HS sequence structure HS molecules are positively identified and structurally characterised by skilled workers in the field by a number of analytical techniques. These include one or a combination of disaccharide analysis, tetrasaccharide analysis, HPLC and molecular weight determination. These analytical techniques are well known to and used by those of skill in the art.

Two techniques for production of di- and tetra-saccharides from HS include nitrous acid digestion and lyase digestion. A description of one way of performing these digestion techniques is provided below, purely by way of example, such description not limiting the scope of the present invention.

Nitrous Acid Digestion

Nitrous acid based depolymerisation of heparan sulphate leads to the eventual degradation of the carbohydrate chain into its individual disaccharide components when taken to completion.

For example, nitrous acid may be prepared by chilling 250 µl of 0.5 M $H_2SO_4$ and 0.5 M $Ba(NO_2)_2$ separately on ice for 15 min. After cooling, the $Ba(NO_2)_2$ is combined with the $H_2SO_4$ and vortexed before being centrifuged to remove the barium sulphate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH is added to the sample and the mixture heated to 50° C. for 20 min. The mixture is then cooled to 25° C. and acidified glacial acetic acid added to bring the sample to pH 3. The mixture is then neutralised with 10 M NaOH and the volume decreased by freeze drying. Final samples are run on a Bio-Gel P-2 column to separate di- and tetrasaccharides to verify the degree of degradation.

Lyase Digestion

Heparinise III cleaves sugar chains at glucuronidic linkages. The series of Heparinase enzymes (I, II and III) each display relatively specific activity by depolymerising certain heparan sulphate sequences at particular sulfation recognition sites. Heparinase I cleaves HS chains with NS regions along the HS chain. This leads to disruption of the sulphated domains. Heparinase III depolymerises HS with the NA domains, resulting in the separation of the carbohydrate chain into individual sulphated domains. Heparinase II primarily cleaves in the NA/NS "shoulder" domains of HS chains, where varying sulfation patterns are found. Note: The repeating disaccharide backbone of the heparan polymer is a uronic acid connected to the amino sugar glucosamine. "NS" means the amino sugar is carrying a sulfate on the amino group enabling sulfation of other groups at C2, C6 and C3. "NA" indicates that the amino group is not sulphated and remains acetylated.

For example, for depolymerisation in the NA regions using Heparinase III both enzyme and lyophilised HS samples are prepared in a buffer containing 20 mM Tris-HCL, 0.1 mg/ml BSA and 4 mM $CaCl_2$ at pH 7.5. Purely by way of example, Heparinase III may be added at 5 mU per 1 µg of HS and incubated at 37° C. for 16 h before stopping the reaction by heating to 70° C. for 5 min.

Di- and tetrasaccharides may be eluted by column chromatography.

Heparin-Binding Domains

Cardin and Weintraub (Molecular Modeling of Protein-Glycosaminoglycan Interactions, Arteriosclerosis Vol. 9 No. 1 January/February 1989 p. 21-32), incorporated herein in entirety by reference, describes consensus sequences for polypeptide heparin-binding domains. The consensus sequence has either a stretch of di- or tri-basic residues separated by two or three hydropathic residues terminated by one or more basic residues. Two particular consensus sequences were identified: XBBXBX [SEQ ID NO:3] and XBBBXXBX [SEQ ID NO:4] in which B is a basic residue (e.g. Lysine, Arginine, Histidine) and X is a hydropathic residue (e.g. Alanine, Glycine, Tyrosine, Serine). Heparin-binding domains are reported to be abundant in amino acids Asn, Ser, Ala, Gly, Ile, Leu and Tyr and have a low occurrence of amino acids Cys, Glu, Asp, Met, Phe and Trp.

These consensus sequences may be used to search protein or polypeptide amino acid sequences in order to identify candidate heparin-binding domain amino acid sequences which may be synthesised and tested for GAG binding in accordance with the present invention.

WO 2005/014619 A2 also discloses numerous heparin-binding peptides. The contents of WO 2005/014619 A2 are incorporated herein in entirety by reference.

Bone Fracture

In some aspects the present invention is concerned with the therapeutic use (human and veterinary) of HS/BMP2 to treat bone fracture. HS/BMP2 is reported here to augment wound healing in bone. HS/BMP2 stimulates bone regeneration following injury and contributes to improved wound healing in bone. HS/BMP2 provides improvements in the speed of bone fracture repair enabling a reduction in the recovery time from injury.

Bone fracture is a medical condition. In this application "fracture" includes damage or injury to bone in which a bone is cracked, broken or chipped. A break refers to discontinuity in the bone. A fracture may be caused by physical impact, or mechanical stress or by medical conditions such as osteoporosis or osteoarthritis.

Orthopaedic classification of fractures includes closed or open and simple or multi-fragmentary fractures. In closed fractures the skin remains intact, whilst in an open fracture the bone may be exposed through the wound site, which brings a higher risk of infection. Simple fractures occur along a single line, tending to divide the bone in two. Multi-fragmentary fractures spilt the bone into multiple pieces.

Other fracture types include, compression fracture, compacted fracture, spiral fracture, complete and incomplete fractures, transverse, linear and oblique fractures and comminuted fractures.

In most subjects bone healing (fracture union) occurs naturally and is initiated following injury. Bleeding normally leads to clotting and attraction of white blood cells and fibroblasts, followed by production of collagen fibres. This is followed by bone matrix (calcium hydroxyapatite) deposition (mineralisation) transforming the collagen matrix into bone. Immature re-generated bone is typically weaker than mature bone and over time the immature bone undergoes a process of remodelling to produce mature "lamellar" bone. The complete bone healing process takes considerable time, typically many months.

Bones in which fractures occur and which may benefit from treatment using HS/BMP2 include all bone types, particularly all mammalian bones including, but not limited to, long bones (e.g. femur, humerus, phalanges), short bones (e.g. carpals, tarsals), flat bones (e.g. cranium, ribs, scapula, sternum, pelvic girdle), irregular bones (e.g. vertebrae), sesamoid bones (e.g. patella).

Bones in which fractures occur and which may benefit from treatment using HS/BMP2 include skeletal bone (i.e. any bone of the skeleton), bones of the cranio-facial region, bones of the axial skeleton (e.g. vertebrae, ribs), appendicular bone (e.g. of the limbs), bone of the pelvic skeleton (e.g. pelvis).

Bones in which fractures occur and which may benefit from treatment using HS/BMP2 also include those of the head (skull) and neck, including those of the face such as the jaw, nose and cheek. In this respect, in some preferred embodiments HS/BMP2 may be used to assist in repair or regeneration of bone during dental or facial or cranial surgery, which may include reconstruction of bones (as distinct from teeth) of the face and/or mouth, e.g. including the jawbone.

Bone fracture also includes pathological porosity, such as that exhibited by subjects with osteoporosis.

Although not limiting to the present invention, the primary actions of HS/BMP2 may be on cells within, adjacent to, or caused to migrate into the wound site and may be on the bone stem cells, the preosteoblasts or the osteoblasts, or on any of the ancillary or vasculogenic cells found or caused to migrate into or within the wound bed.

HS/BMP2 and pharmaceutical compositions and medicaments comprising HS/BMP2 are provided for use in a method of treatment of bone fracture in a mammalian subject.

Treatment may comprise wound healing in bone. The treatment may involve repair, regeneration and growth of bone. HS/BMP2 facilitates fracture repair by facilitating new bone growth. HS/BMP2 acts to improve the speed of fracture repair enabling bone healing to occur faster leading to improved recovery time from injury. Treatment may lead to improved bone strength.

Treatment may also include treatment of osteoporosis or osteoarthritis.

Administration of HS/BMP2 is preferably to the tissue surrounding the fracture. This may include administration directly to bone tissue in which the fracture has occurred. Administration may be to connective tissue surrounding the bone or fracture or to vasculature (e.g. blood vessels) near to and supplying the bone. Administration may be directly to the site of injury and may be to a callus formed by initial healing of the wound.

Medicaments and pharmaceutical compositions according to the present invention may be formulated for administration by a number of routes. Most preferably HS/BMP2 is formulated in fluid or liquid form for injection.

In some embodiments the HS/BMP2 is formulated as a controlled release formulation, e.g. in a drug capsule for implantation at the wound site. The HS/BMP2 may be attached to, impregnated on or soaked into a carrier material (e.g. a biomaterial) such as nanofibres or biodegradable paper or textile.

Pharmaceutical compositions, medicaments, implants and prostheses comprising HS/BMP2 may also comprise BMP2. Owing to the ability of HS/BMP2 to bind BMP2, the HS/BMP2 may act as a carrier of BMP2 assisting in delivery of BMP2 to the wound site and maintenance of BMP2 stability.

Administration is preferably in a "therapeutically effective amount", this being sufficient to improve healing of the bone fracture compared to a corresponding untreated fracture. The actual amount administered, and rate and time-course of administration, will depend on the nature and severity of the fracture. Prescription of treatment, e.g. decisions on dosage etc, is within the responsibility of general practitioners and other medical doctors, and will typically take account of the nature of the fracture, the condition of the individual patient, the site of delivery, the method of administration and other factors known to practitioners. Single or multiple administrations of HS/BMP2 doses may be administered in accordance with the guidance of the prescribing medical practitioner. Purely by way of example, HS/BMP2 may be delivered in dosages of at least 1 ng/ml, more preferably at least 5 ng/ml and optionally 10 ng/ml or more. Individual HS/BMP dosages may be of the order less than 1 mg and greater than 1 µg, e.g. one of about 5 µg, about 10 µg, about 25 µg, about 30 µg, about 50 µg, about 100 µg, about 0.5 mg, or about 1 mg. Examples of the techniques and protocols mentioned above can be found in Remington's Pharmaceutical Sciences, 20th Edition, 2000, pub. Lippincott, Williams & Wilkins.

HS/BMP2 may be used to treat bone fracture alongside other treatments, such as administration of pain relieving or anti-inflammatory medicaments, immobilisation and setting of the bone, e.g. immobilising the injured limb in a plaster cast, surgical intervention, e.g. to re-set a bone or move a bone to correct displacement, angulation or dislocation. If surgery is required HS/BMP2 may be administered directly to (e.g. applied to) the fracture during the surgical procedure.

Biomaterials

Pharmaceutical compositions and medicaments of the invention may take the form of a biomaterial that is coated and/or impregnated with HS/BMP2. An implant or prosthesis may be formed from the biomaterial. Such implants or prostheses may be surgically implanted to assist in bone growth, regeneration, restructuring and/or remodelling.

HS/BMP2 may be applied to implants or prostheses to accelerate new bone formation at a desired location. It will be appreciated that heparan sulphates, unlike proteins, are particularly robust and have a much better ability to withstand the solvents required for the manufacture of synthetic bioscaffolds and application to implants and prostheses.

The biomaterial may be coated or impregnated with HS/BMP2. Impregnation may comprise forming the biomaterial by mixing HS/BMP2 with the constitutive components of the biomaterial, e.g. during polymerisation, or absorbing HS/BMP2 into the biomaterial. Coating may comprise adsorbing the HS/BMP2 onto the surface of the biomaterial.

The biomaterial should allow the coated or impregnated HS/BMP2 to be released from the biomaterial when administered to or implanted in the subject. Biomaterial release kinetics may be altered by altering the structure, e.g. porosity, of the biomaterial.

In addition to coating or impregnating a biomaterial with HS/BMP2, one or more biologically active molecules may be impregnated or coated on the biomaterial. For example, at least one chosen from the group consisting of: BMP-2, BMP-4, OP-1, FGF-1, FGF-2, TGF-β1, TGF-β2, TGF-β3; VEGF; collagen; laminin; fibronectin; vitronectin. In addition or alternatively to the above bioactive molecules, one or more bisphosphonates may be impregnated or coated onto the biomaterial along with HS/BMP2. Examples of useful bisphosphonates may include at least one chosen from the group consisting of: etidronate; clodronate; alendronate; pamidronate; risedronate; zoledronate.

Biomaterials coated or impregnated with HS/BMP2 may be useful in both medical and veterinary purposes. It will be appreciated that the present invention may improve the quality of life of a patient or potentially extend the life of an animal, for example a valuable racehorse for use in breeding.

The biomaterial provides a scaffold or matrix support. The biomaterial may be suitable for implantation in tissue, or may be suitable for administration (e.g. as microcapsules in solution).

The implant or prosthesis should be biocompatible, e.g. non-toxic and of low immunogenicity (most preferably non-immunogenic). The biomaterial may be biodegradable such that the biomaterial degrades as wound healing occurs, ultimately leaving only the regenerated bone in situ in the subject. Alternatively a non-biodegradable biomaterial may be used, e.g. to guide bone regeneration over a large discontinuity and/or to act as a structural support during bone healing, with surgical removal of the biomaterial being an optional requirement after successful wound healing.

Biomaterials may be soft and/or flexible, e.g. hydrogels, fibrin web or mesh, or collagen sponges. A "hydrogel" is a substance formed when an organic polymer, which can be natural or synthetic, is set or solidified to create a three-dimensional open-lattice structure that entraps molecules of water or other solutions to form a gel. Solidification can occur by aggregation, coagulation, hydrophobic interactions or cross-linking.

Alternatively biomaterials may be relatively rigid structures, e.g. formed from solid materials such as plastics or biologically inert metals such as titanium.

The biomaterial may have a porous matrix structure which may be provided by a cross-linked polymer. The matrix is preferably permeable to nutrients and growth factors required for bone growth.

Matrix structures may be formed by crosslinking fibres, e.g. fibrin or collagen, or of liquid films of sodium alginate, chitosan, or other polysaccharides with suitable crosslinkers, e.g. calcium salts, polyacrylic acid, heparin. Alternatively scaffolds may be formed as a gel, fabricated by collagen or alginates, crosslinked using well established methods known to those skilled in the art.

Suitable polymer materials for matrix formation include, but are not limited by, biodegradable/bioresorbable polymers which may be chosen from the group of: agarose, collagen, fibrin, chitosan, polycaprolactone, poly(DL-lactide-co-caprolactone), poly(L-lactide-co-caprolactone-co-glycolide), polyglycolide, polylactide, polyhydroxyalcanoates, co-polymers thereof, or non-biodegradable polymers which may be chosen from the group of: cellulose acetate; cellulose butyrate, alginate, polysulfone, polyurethane, polyacrylonitrile, sulfonated polysulfone, polyamide, polyacrylonitrile, polymethylmethacrylate, co-polymers thereof.

Collagen is a promising material for matrix construction owing to its biocompatibility and favourable property of supporting cell attachment and function (U.S. Pat. No. 5,019,087; Tanaka, S.; Takigawa, T.; Ichihara, S. & Nakamura, T. Mechanical properties of the bioabsorbable polyglycolic acid-collagen nerve guide tube *Polymer Engineering & Science* 2006, 46, 1461-1467). Clinically acceptable collagen sponges are one example of a matrix and are well known in the art (e.g. from Integra Life Sciences).

Fibrin scaffolds (e.g. fibrin glue) provide an alternative matrix material. Fibrin glue enjoys widespread clinical application as a wound sealant, a reservoir to deliver growth factors and as an aid in the placement and securing of biological implants (Rajesh Vasita, Dhirendra S Katti. Growth factor delivery systems for tissue engineering: a materials perspective. *Expert Reviews in Medical Devices.* 2006; 3(1): 29-47; Wong C, Inman E, Spaethe R, Helgerson S. *Thromb. Haemost.* 2003 89(3): 573-582; Pandit A S, Wilson D J, Feldman D S. Fibrin scaffold as an effective vehicle for the delivery of acidic growth factor (FGF-1). *J. Biomaterials Applications.* 2000; 14(3); 229-242; DeBlois Cote M F. Doillon C J. Heparin-fibroblast growth factor fibrin complex: in vitro and in vivo applications to collagen based materials. *Biomaterials.* 1994; 15(9): 665-672.).

Luong-Van et al (In vitro biocompatibility and bioactivity of microencapsulated heparan sulphate *Biomaterials* 28 (2007) 2127-2136), incorporated herein by reference, describes prolonged localised delivery of HS from polycaprolactone microcapsules.

A further example of a biomaterial is a polymer that incorporates hydroxyapatite or hyaluronic acid.

One example of a biomaterial suitable for use in combination with HS/BMP2 is the JAX™ bone void filler (Smith & Nephew). Jax granules are composed of high purity calcium sulfate and retain their shape to provide a scaffold with controlled, inter-granular porosity and granule migration stability. Jax granules dissolve safely and completely in the body.

Other suitable biomaterials include ceramic or metal (e.g. titanium), hydroxyapatite, tricalcium phosphate, demineralised bone matrix (DBM), autografts (i.e. grafts derived from the patient's tissue), or allografts (grafts derived from the tissue of an animal that is not the patient). Biomaterials may be synthetic (e.g. metal, fibrin, ceramic) or biological (e.g. carrier materials made from animal tissue, e.g. non-human mammals (e.g. cow, pig), or human).

The biomaterial can be supplemented with additional cells. For example, one can "seed" the biomaterial (or co-synthesise it) with undifferentiated bone precursor cells, e.g. stem cells such as mesenchymal stem cells, more preferably human mesenchymal stem cells.

The subject to be treated may be any animal or human. The subject is preferably mammalian, more preferably human. The subject may be a non-human mammal (e.g. rabbit, guinea pig, rat, mouse or other rodent (including cells from any animal in the order Rodentia), cat, dog, pig, sheep, goat, cattle (including cows, e.g. dairy cows, or any animal in the order Bos), horse (including any animal in the order Equidae), donkey, and non-human primate). The non-human mammal may be a domestic pet, or animal kept for commercial purposes, e.g. a race horse, or farming livestock such as pigs, sheep or cattle. The subject may be male or female. The subject may be a patient.

Culture Media

Culture media comprising HS/BMP2 may be of any kind but is preferably liquid or gel and may contain other nutrients and growth factors (e.g. FGF-2). HS/BMP2 will preferably be present in non-trace amounts. For example, the concentration of HS/BMP2 in the culture media may range between about 1.0 ng/ml culture media to about 1000 ng/ml culture media. Preferably, the concentration of HS/BMP2 in the culture media is between about 5 ng/ml culture media and 200 ng/ml culture media, more preferably between about 20 ng/ml culture media and 170 ng/ml culture media.

BMP2 Protein

In this specification BMP2 refers to Bone morphogenetic protein 2 (also called bone morphogenic protein 2, BMP2 or BMP-2), which is a member of the TGF-β superfamily and is implicated in the development of bone and cartilage.

The amino acid sequence of BMP2 preprotein from *Homo sapiens* (SEQ ID NO:2) is shown in FIG. 35. Amino acids 1 to 23 represent the signal peptide, and amino acids 24 to 396 represent the amino acid sequence of the proprotein. The amino acid sequence of the mature protein is given as SEQ ID NO:5 herein.

In this specification "BMP2 protein" includes proteins having at least 70%, more preferably one of 75%, 80%, 85%, 90%, 95%, 96%, 97%, 98%, 99% or 100% sequence identity with the amino acid sequence of the BMP2 preprotein or BMP2 proprotein illustrated in FIG. 35 or with the amino acid sequence of the mature BMP2 protein of SEQ ID NO:5.

The BMP2 protein preferably also includes a heparin binding domain having the amino acid sequence of SEQ ID NO:1 or 6 (found at amino acids 283-300 of SEQ ID NO:2), or an amino acid sequence having one of 75%, 80%, 85%, 90%, 95%, 96%, 97%, 98%, or 99% sequence identity to SEQ ID NO:1 or 6.

Reference to BMP2 protein preferably includes the BMP-2 protein described in Ruppert et al (Eur J. Biochem 1996).

The BMP2 protein is preferably osteogenic, i.e. has the activity of inducing, or assisting in the induction of, osteoblast differentiation.

The BMP2 protein may be from, or derived from, any animal or human, e.g. non-human animals, e.g. rabbit, guinea pig, rat, mouse or other rodent (including from any animal in the order Rodentia), cat, dog, pig, sheep, goat, cattle (including cows, e.g. dairy cows, or any animal in the order Bos), horse (including any animal in the order Equidae), donkey, and non-human primate or other non-human vertebrate organism; and/or non-human mammalian animal; and/or human.

The invention includes the combination of the aspects and preferred features described except where such a combination is clearly impermissible or expressly avoided.

The section headings used herein are for organizational purposes only and are not to be construed as limiting the subject matter described.

Aspects and embodiments of the present invention will now be illustrated, by way of example, with reference to the accompanying figures. Further aspects and embodiments will be apparent to those skilled in the art. All documents mentioned in this text are incorporated herein by reference.

BRIEF DESCRIPTION OF THE FIGURES

Embodiments and experiments illustrating the principles of the invention will now be discussed with reference to the accompanying figures in which:

FIG. 3. tGAGs (2.5 mg) loaded onto an underivatised Hi-Trap streptavidin column. All GAGs elute from the column in the flowthrough, indicating no "background" attachment of GAGs to the column.

FIG. 4. BMP2-HBP (1 mg) pre-incubated with tGAGs (25 mg) for 30 min. Elution profile shows the peptide (280 nm) exiting the column in the flowthrough together with the tGAG sample.

The chromatogram (232 nm) reveals that very few GAG fragments bound to the peptide.

Figure 22:
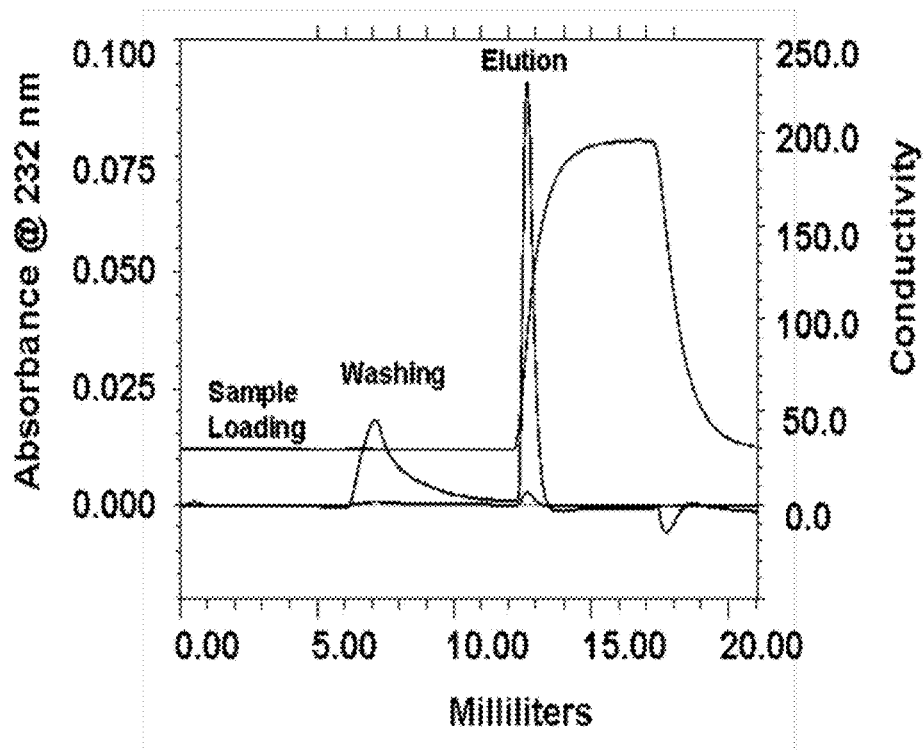

FIG. 22. Chromatogram showing steps in isolation of BMP-2 peptide specific HS by affinity chromatography.

Figure 23:
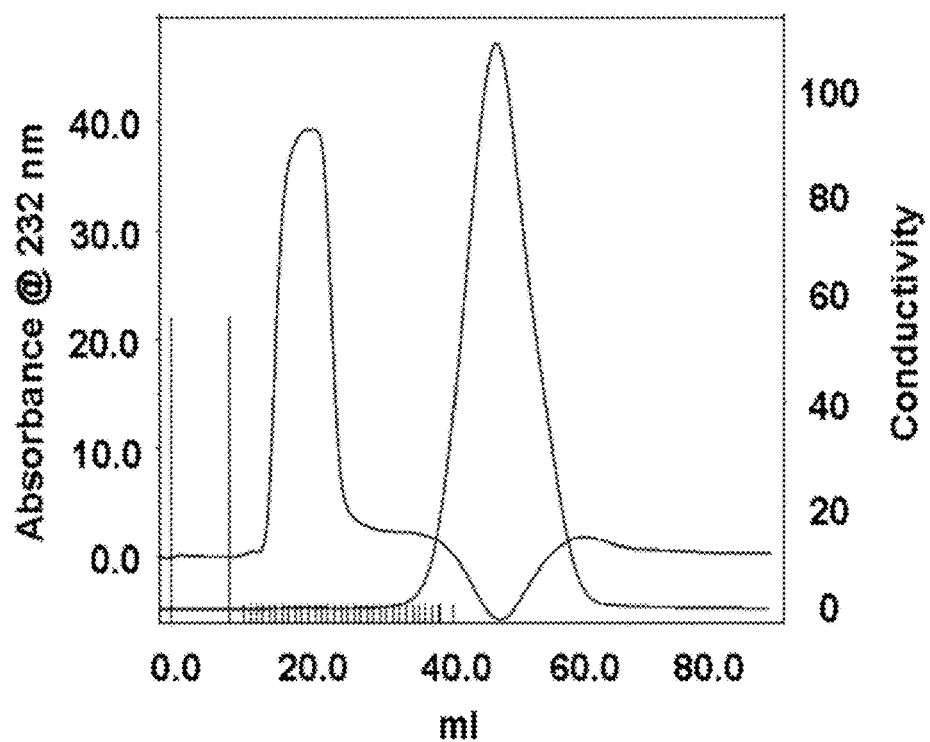

FIG. 23. Chromatogram showing elution of BMP-2 peptide specific HS (GAG+) by affinity chromatography.

Figure 24:
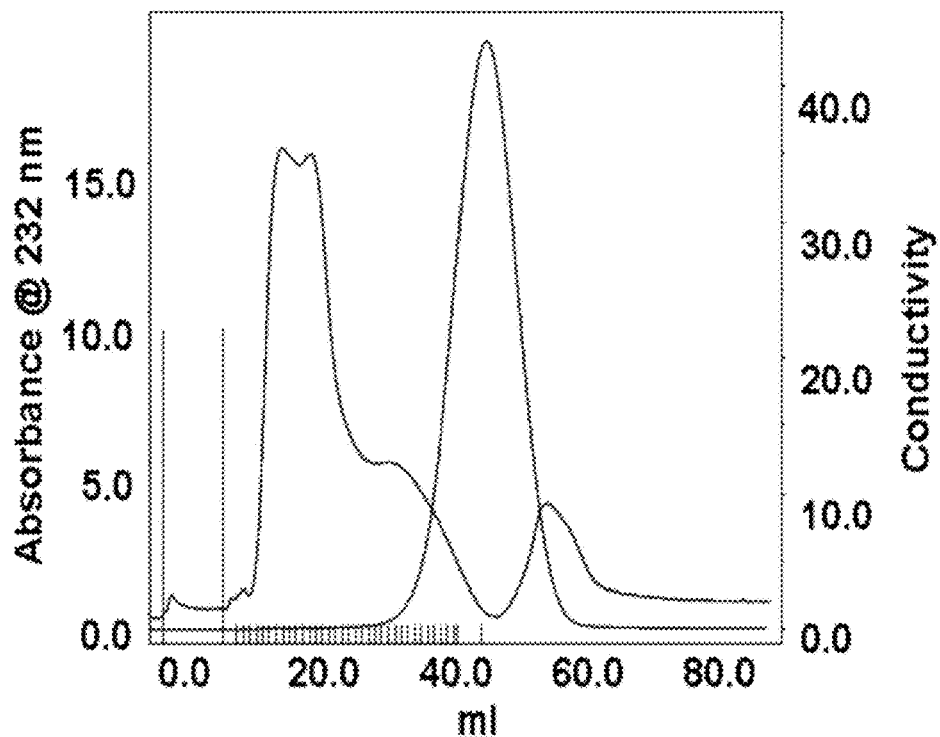

FIG. 24. Chromatogram showing elution of BMP-2 peptide non-specific HS (GAG−) by affinity chromatography.

Figure 25:
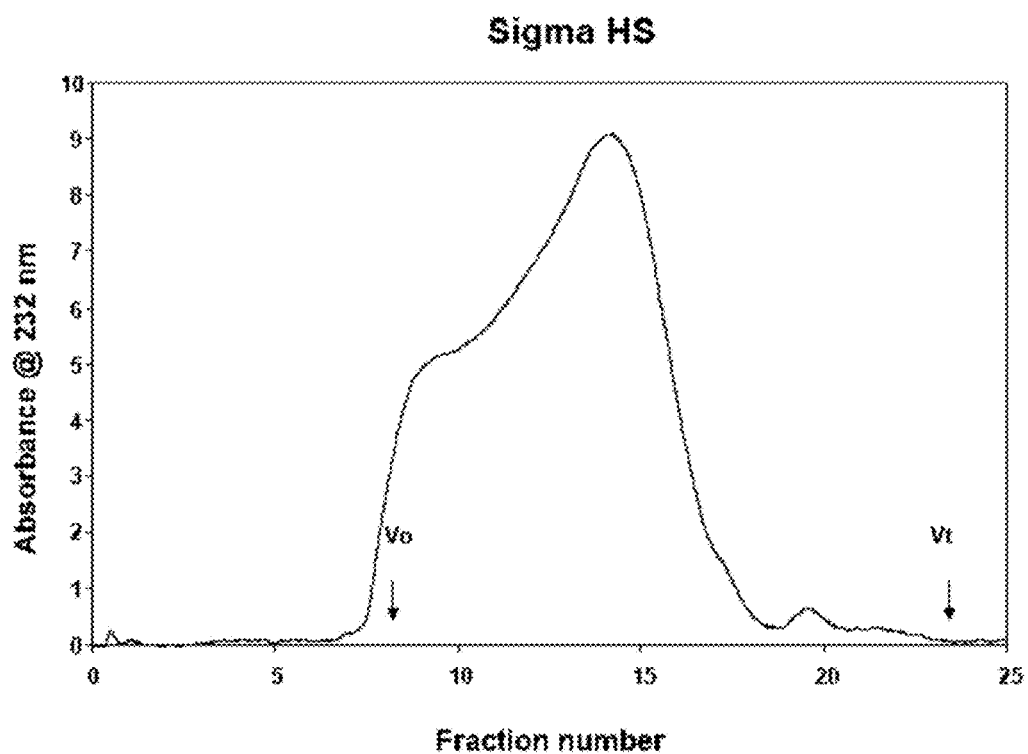

FIG. 25. Chromatogram showing elution of Sigma HS (H9902) standard under size exclusion chromatography on Superdex 75 column.

Figure 26:
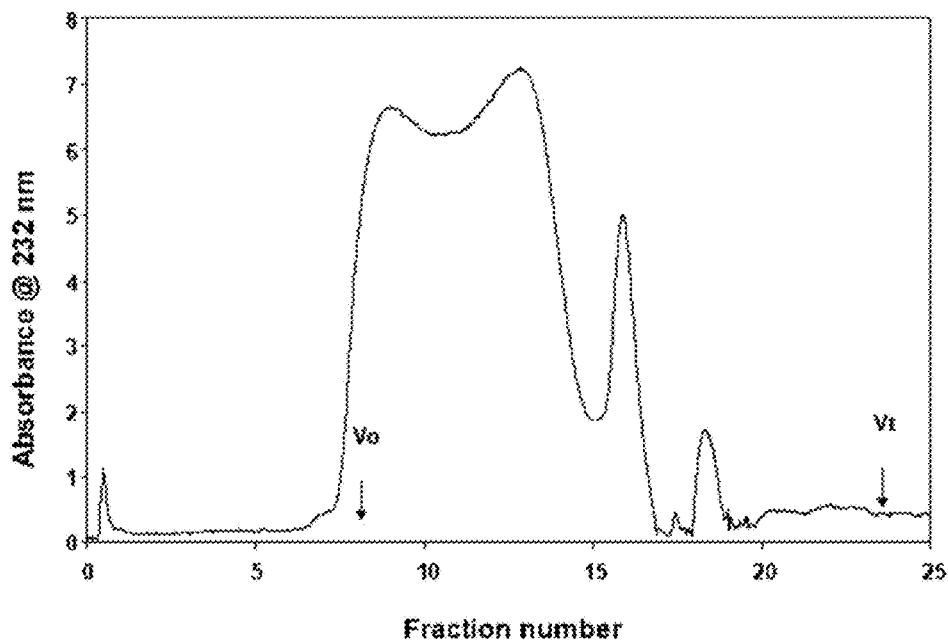

FIG. 26. Chromatogram showing elution of BMP-2 peptide specific HS (GAG+) under size exclusion chromatography on Superdex 75 column.

Figure 27:
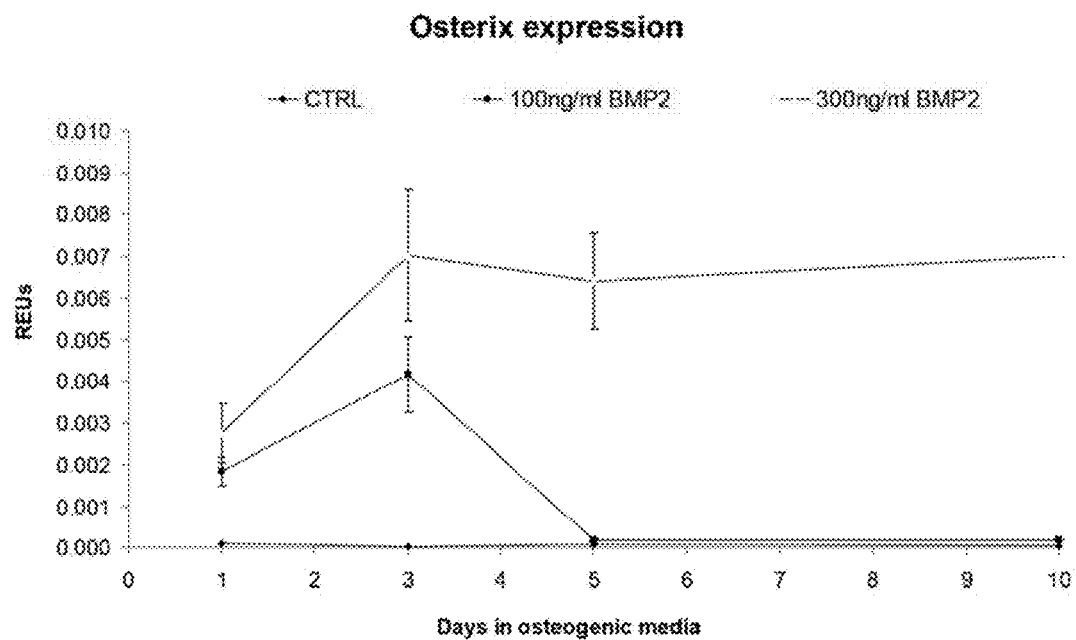

FIG. 27. Graph showing Osterix expression in C2C12 cells in response to control media, 100 ng/ml BMP2 and 300 ng/ml BMP2.

Figure 28:
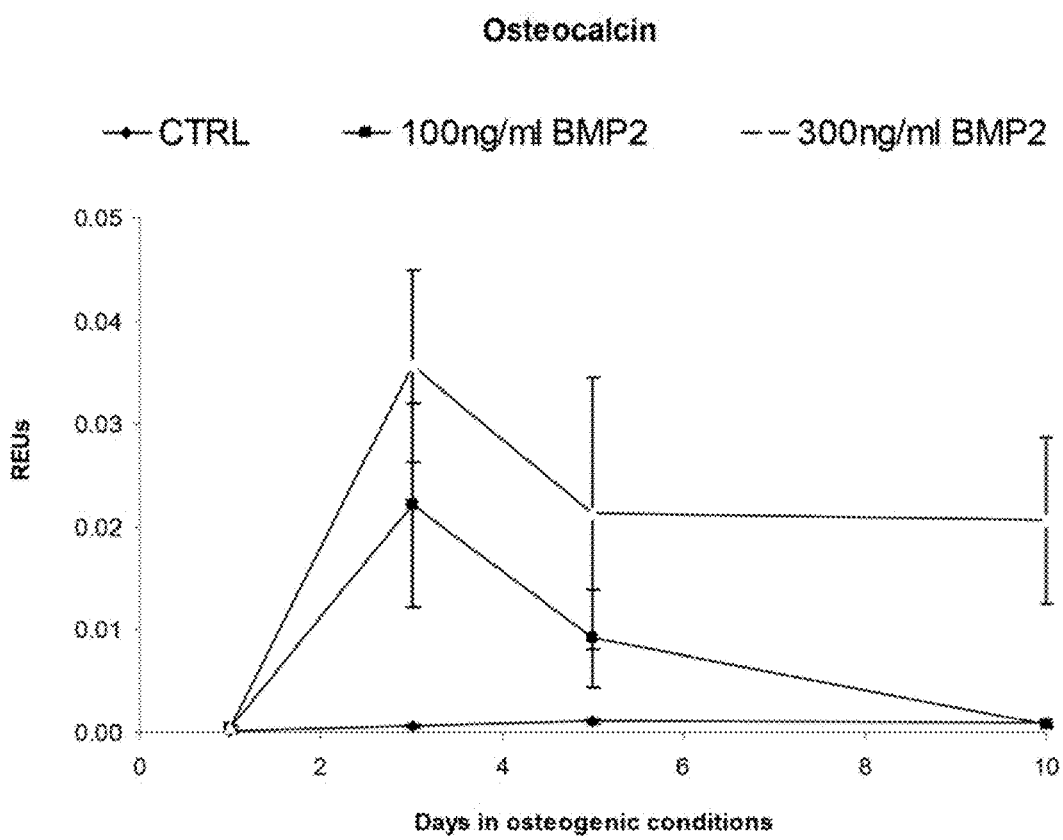

FIG. 28. Graph showing Osteocalcin expression in C2C12 cells in response to control media, 100 ng/ml BMP2 and 300 ng/ml BMP2.

Figure 29:
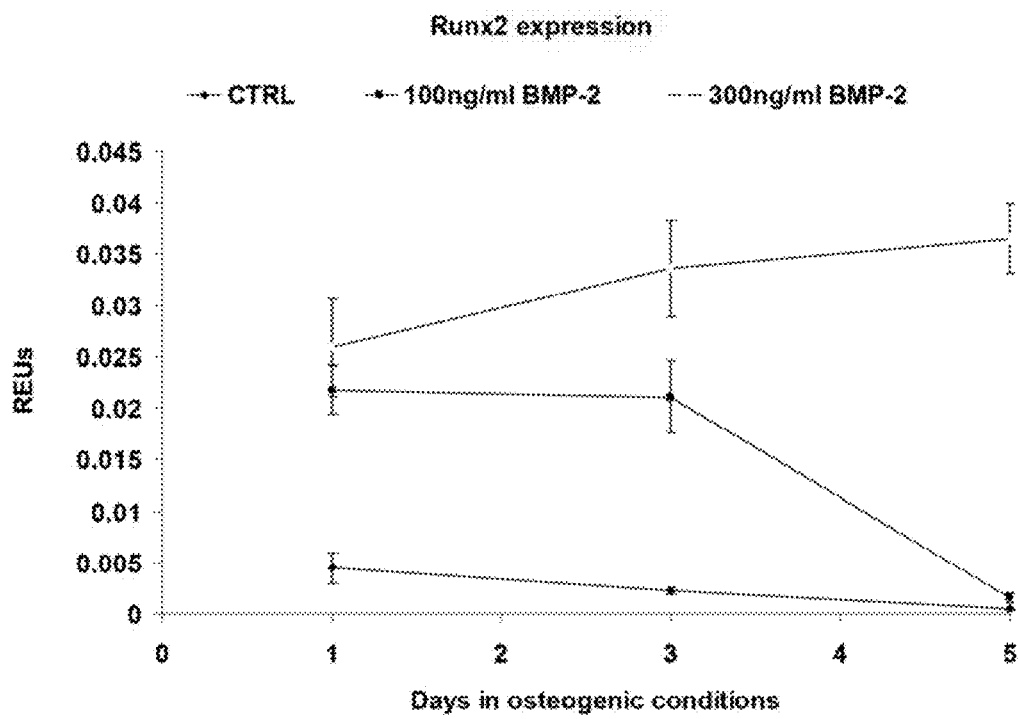

FIG. 29. Graph showing Runx2 expression in C2C12 cells in response to control media, 100 ng/ml BMP2 and 300 ng/ml BMP2.

Figure 30:
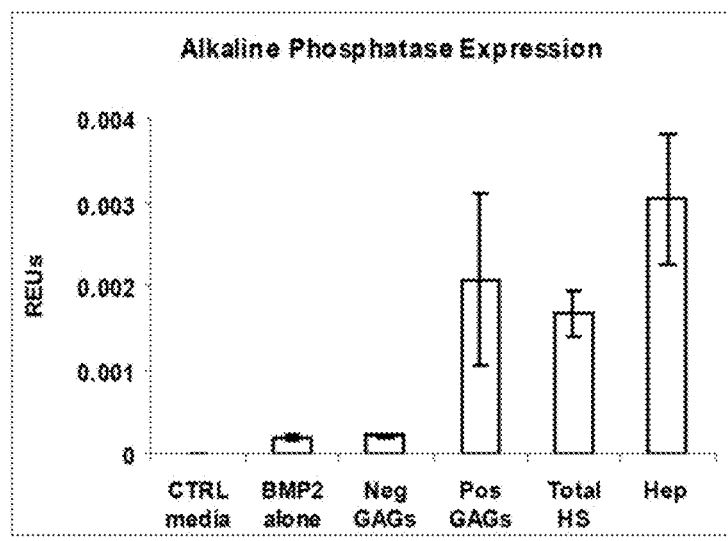

FIG. 30. Graph showing expression of Alkaline Phosphatase as measured by quantitative PCR in C2C12 cells in response to control media, BMP-2, Negative GAG (GAG), Positive GAGs (GAG+), Total HS and Heparin (Hep).

Figure 31:
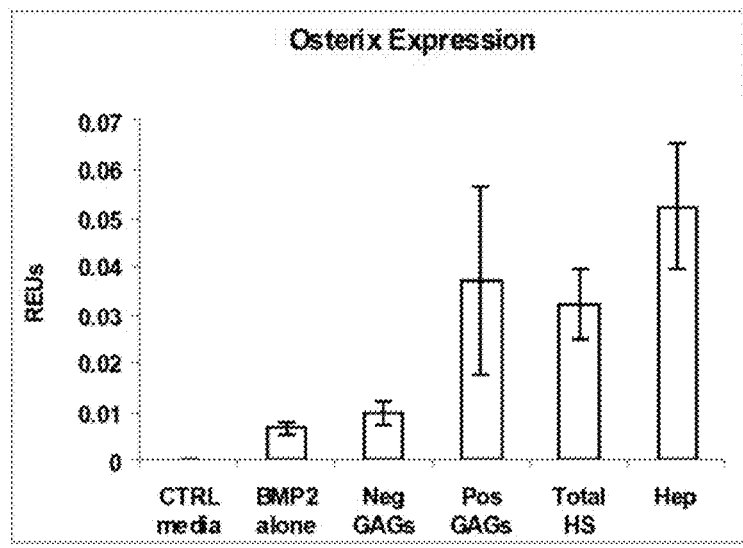

FIG. 31. Graph showing expression of Osterix as measured by quantitative PCR in C2C12 cells in response to control media, BMP-2, Negative GAG (GAG−)+BMP-2, Positive GAGs (GAG+)+BMP-2, Total HS and Heparin (Hep).

Figure 32:
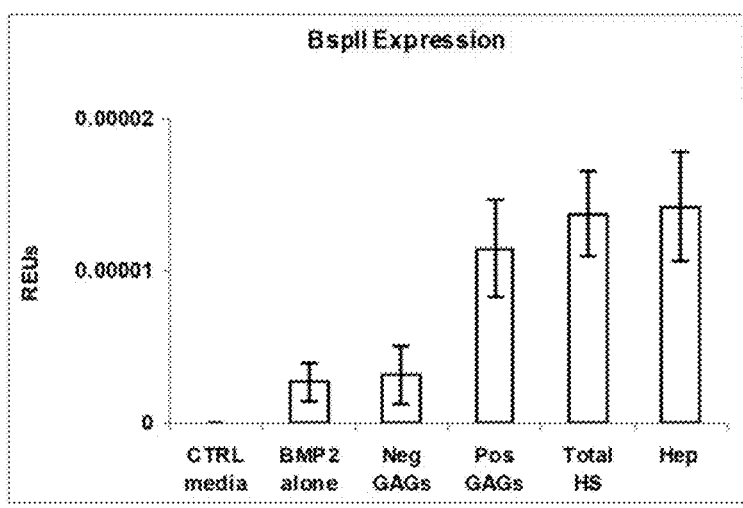

FIG. 32. Graph showing expression of BspII as measured by quantitative PCR in C2C12 cells in response to control media, BMP-2, Negative GAG (GAG−)+BMP-2, Positive GAGs (GAG+)+BMP-2, Total HS and Heparin (Hep).

Figure 33:
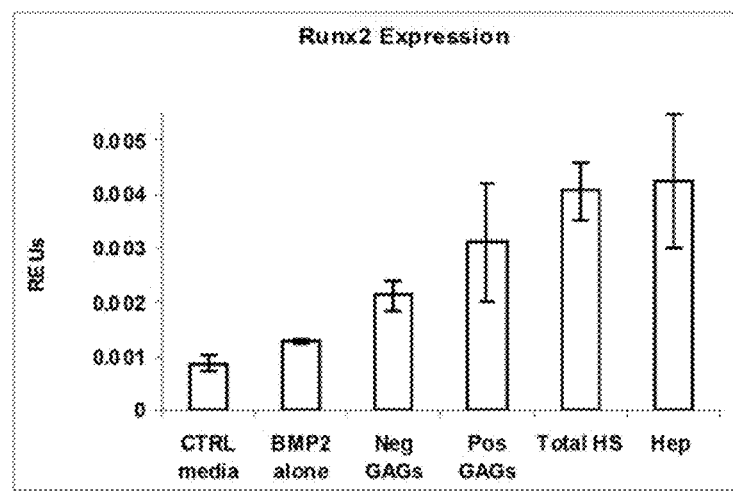

FIG. 33. Graph showing expression of Runx2 as measured by quantitative PCR in C2C12 cells in response to control media, BMP-2, Negative GAG (GAG−)+BMP-2, Positive GAGs (GAG+)+BMP-2, Total HS and Heparin (Hep).

Figure 34:
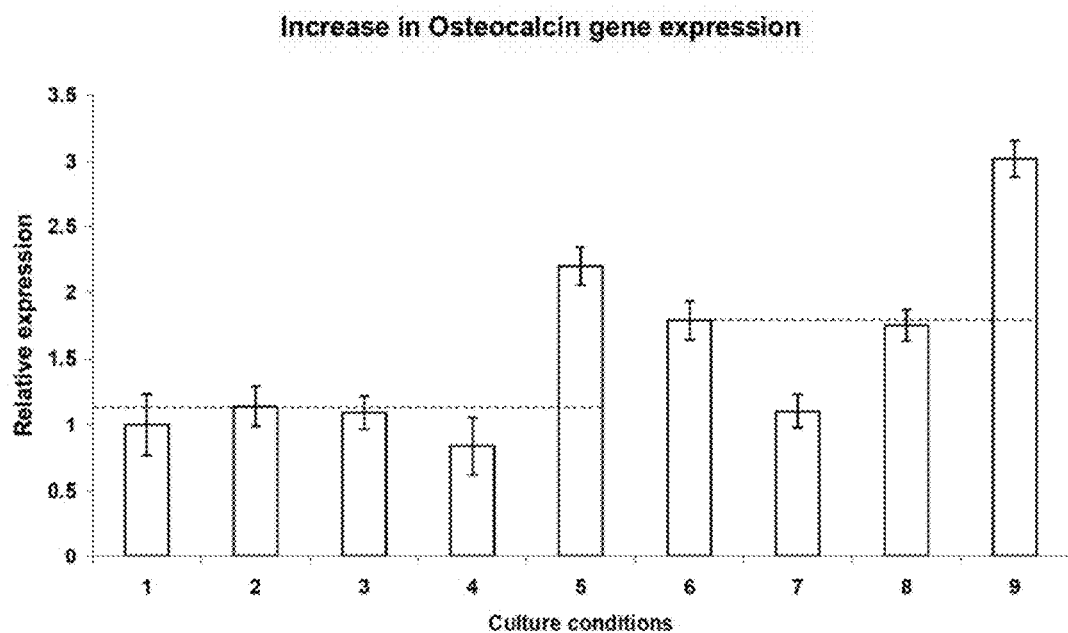

FIG. 34. Graph showing expression of Osteocalcin in C2C12 cells in response to BMP and GAG+(+BMP-2) isolated from MC3T3-E1 cells.

FIG. 35. Amino acid sequence of bone morphogenetic protein 2 preprotein from *Homo sapiens*, NCBI Accession No. NP_001191 (NP_001191.1 GI:4557369) (SEQ ID NO:2).

Figure 36:
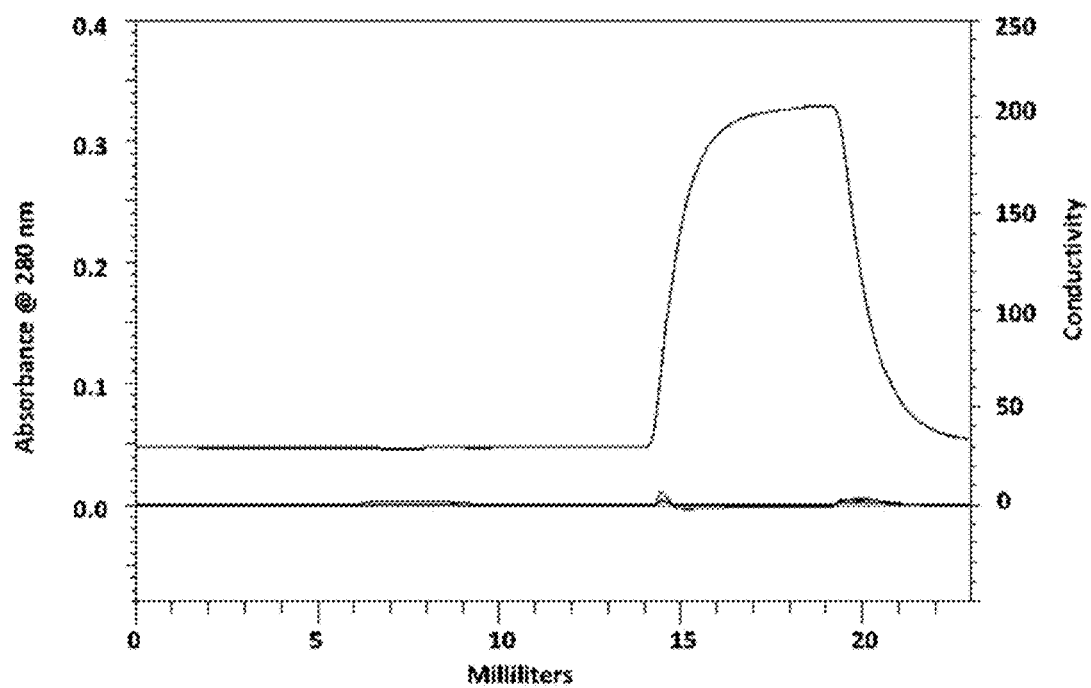

FIG. 36. Chromatogram showing elution of BMP-2 peptide specific HS by affinity chromatography. 6 mg Biotinylated BMP2-peptide (SEQ ID NO:1) was coupled to a 1 ml Streptavidin column. The chromotagram shows that all of the biotinylated BMP2-peptide bound to the column.

Figure 37:
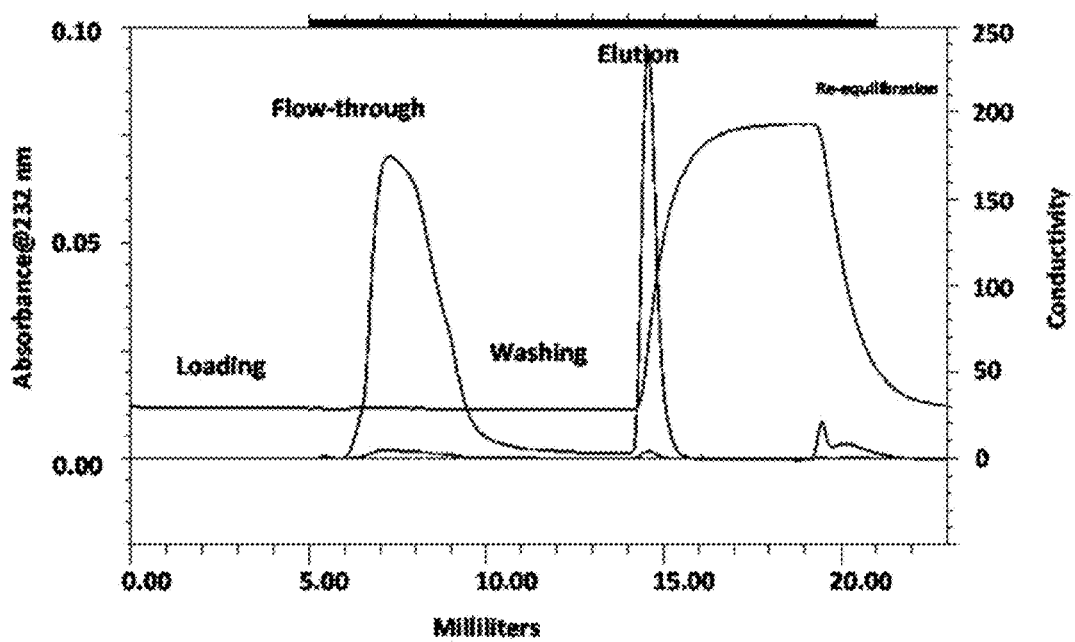

FIG. 37. Chromatogram showing purification of BMP2-peptide (SEQ ID NO:1) specific heparan sulphate.

Figure 38:
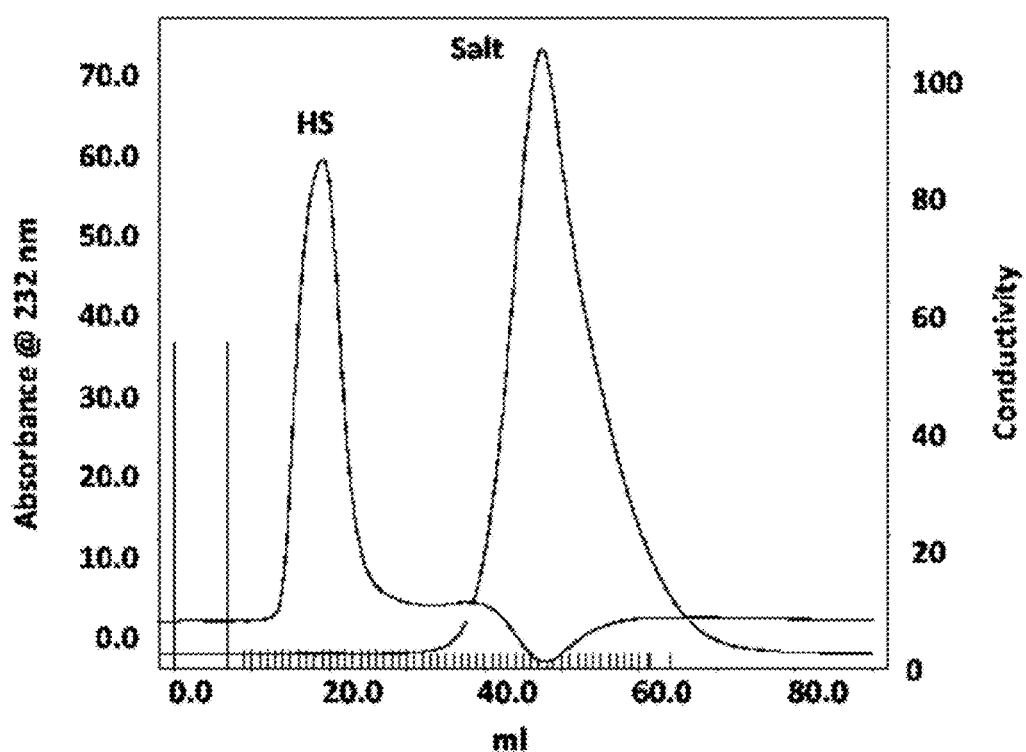

FIG. 38. Chromatogram showing desalting of BMP2 peptide (SEQ ID NO:1) column bound heparan sulphate.

Figure 39:
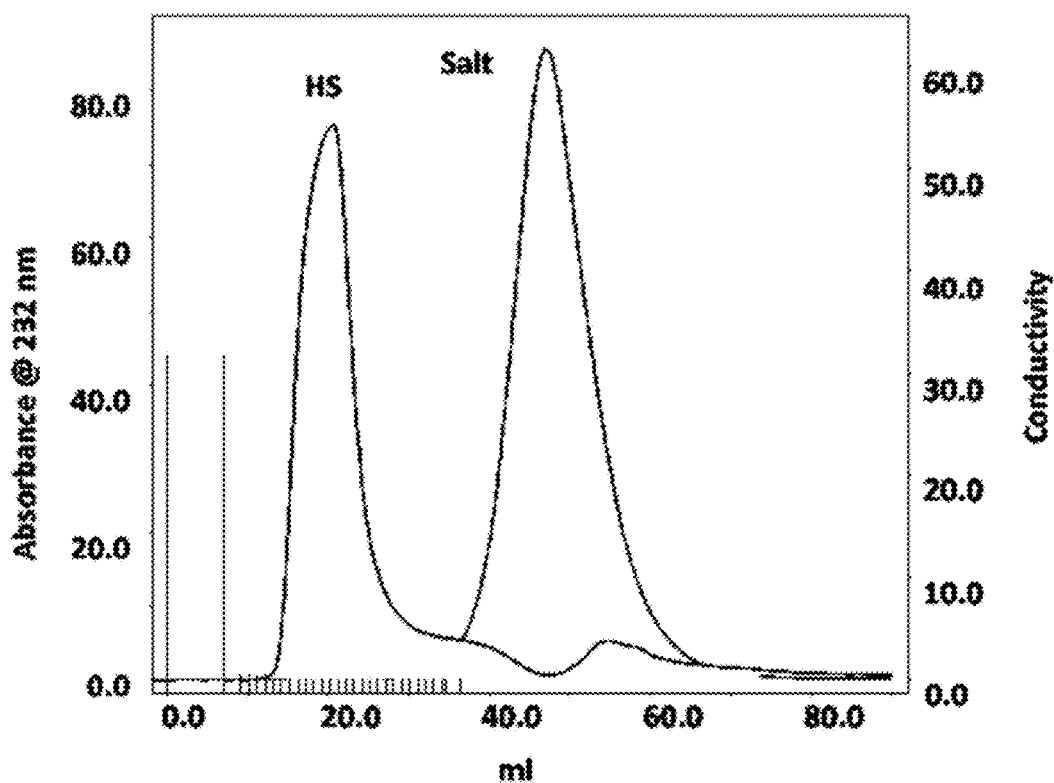

FIG. 39. Chromatogram showing desalting of BMP2 peptide (SEQ ID NO:1) column unbound heparan sulphate.

Figure 40:
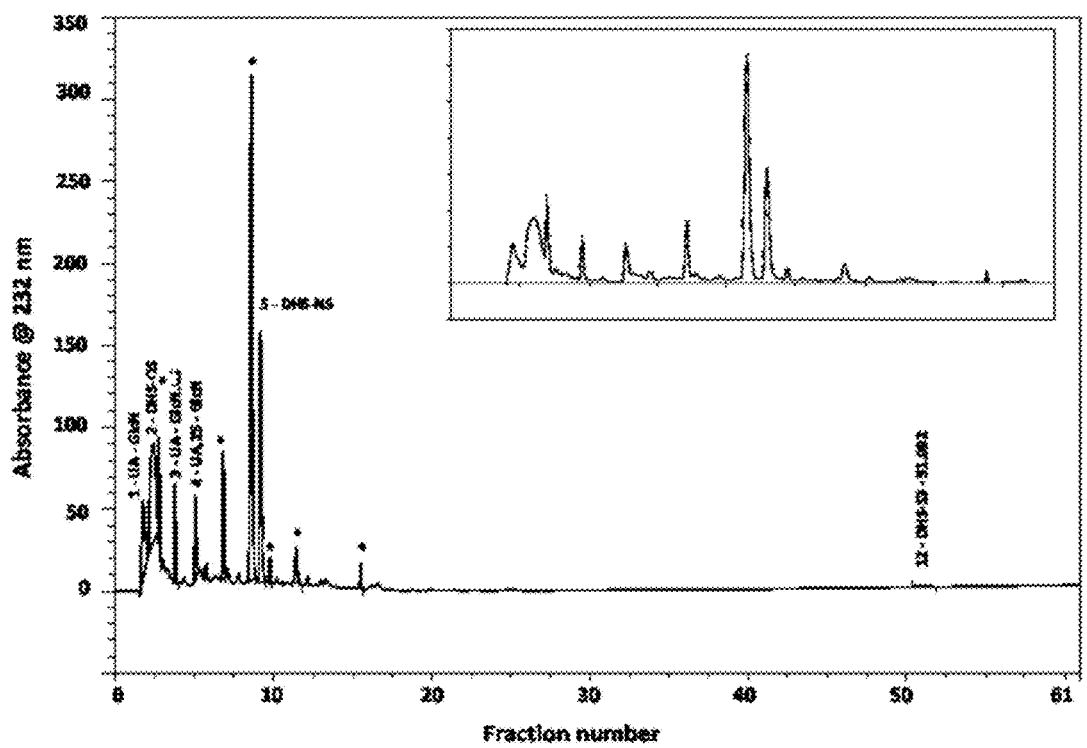

FIG. 40. SAX-HPLC profile following disaccharide digestion of BMP2 positive heparan sulphate.

Figure 41:
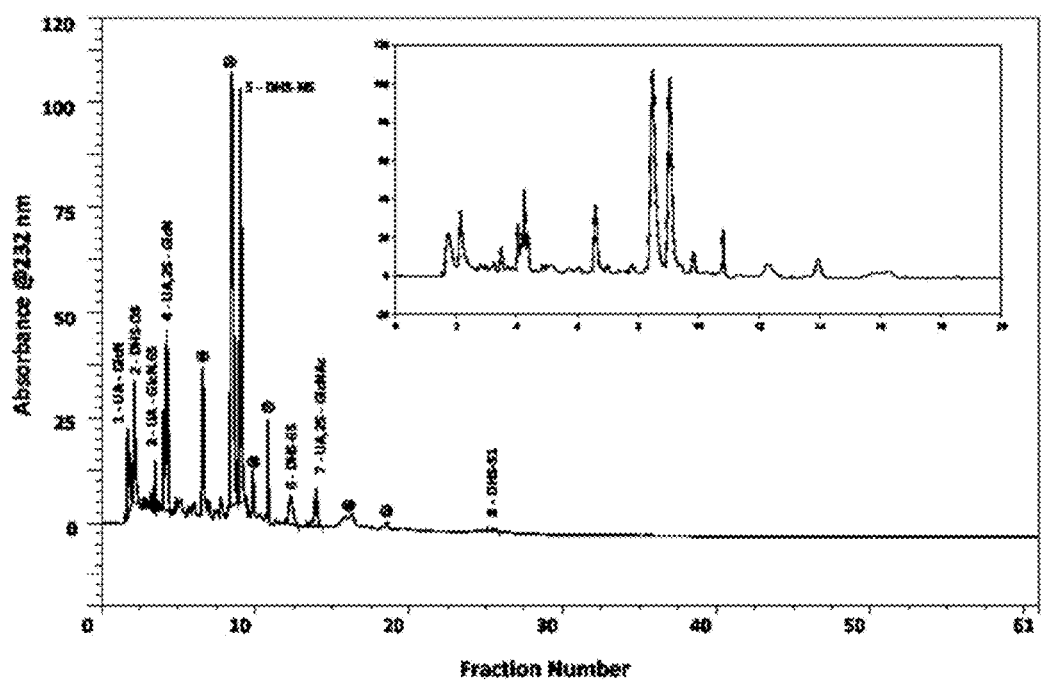

FIG. 41. SAX-HPLC profile following disaccharide digestion of BMP2 negative heparan sulphate.

Figure 42:
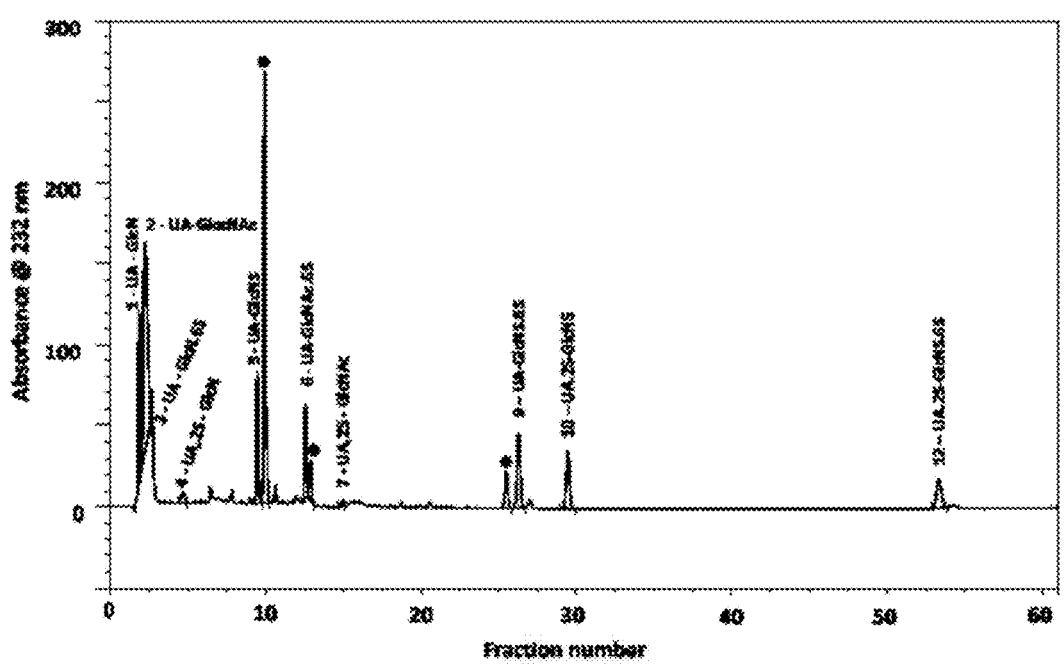

FIG. 42. SAX-HPLC profile following disaccharide digestion of Celsus HS.

FIG. 43. Table showing lyase-derived disaccharide percentage composition of BMP2-specific HS, BMP2-non-specific HS and Celsus HS. The area under each peak was integrated to calculate the percentage of each disaccharide. --=not detected.

Figure 44:
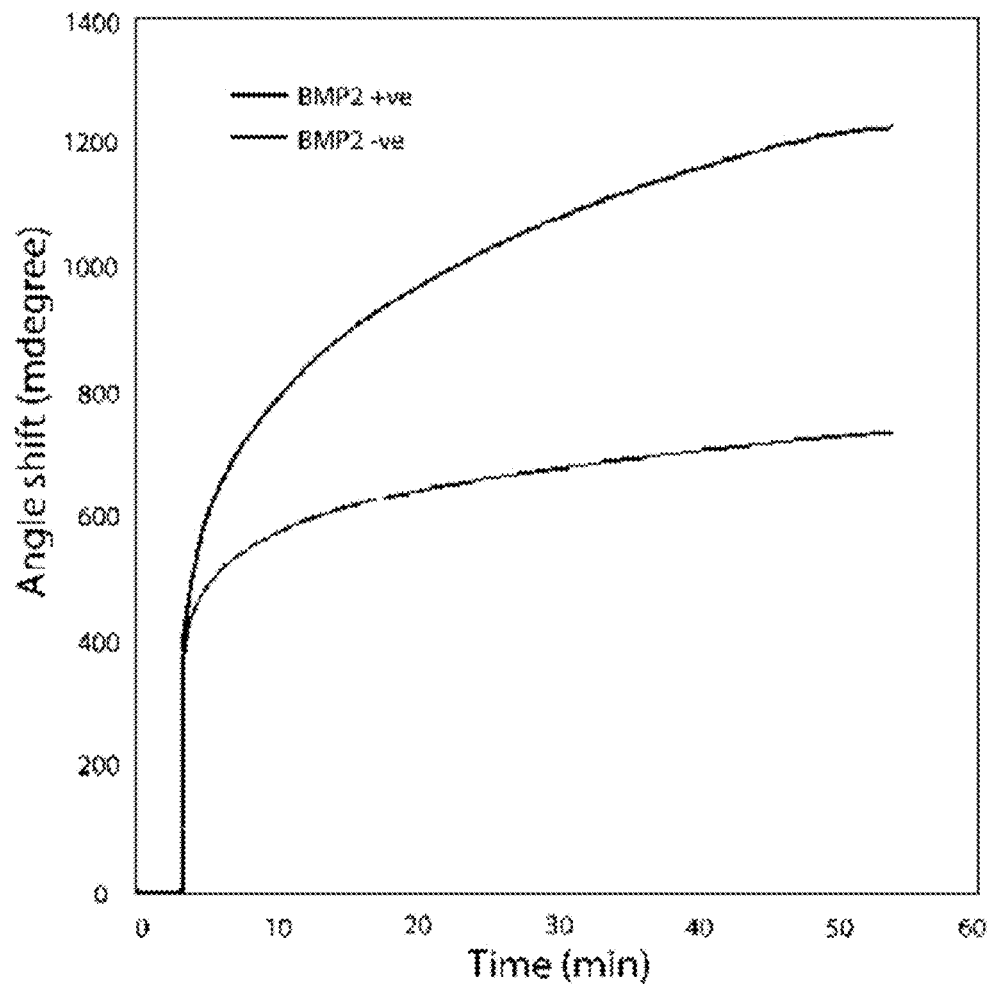

FIG. 44. Chart showing surface plasmon resonance (SPR) analysis of BMP2 positive and BMP2 negative HS.

Figure 45:
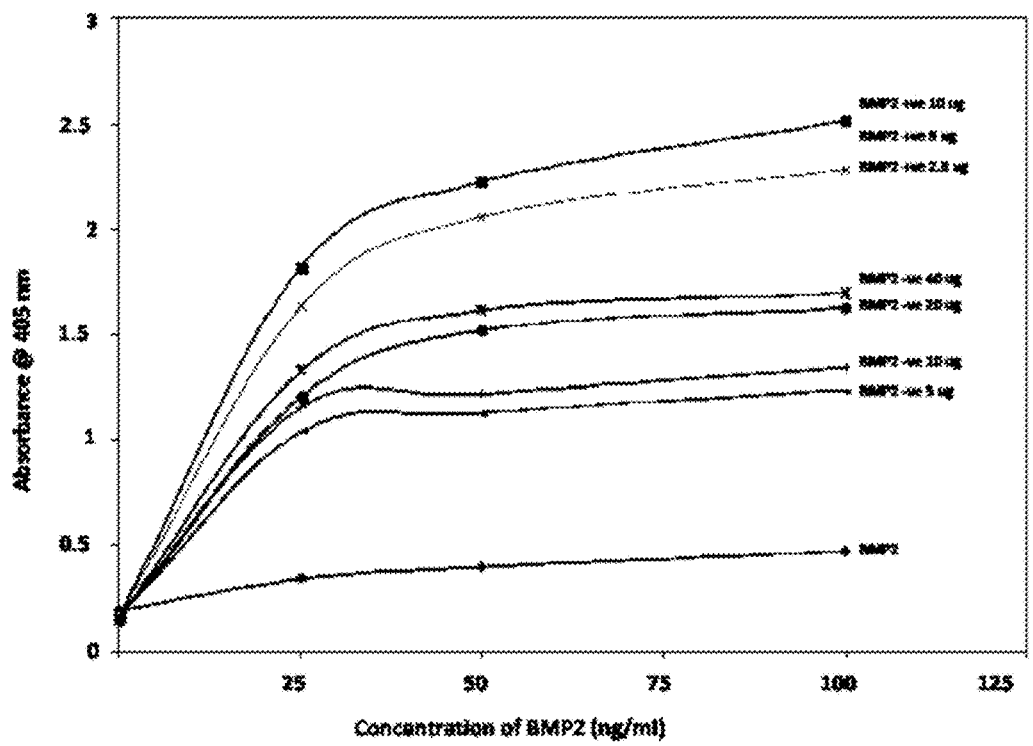

FIG. 45. Chart showing BMP2 binding capacity of BMP2 positive and BMP2 negative Celsus HS preparations coated on an Iduron Heparin/GAG binding plate.

Figure 46:
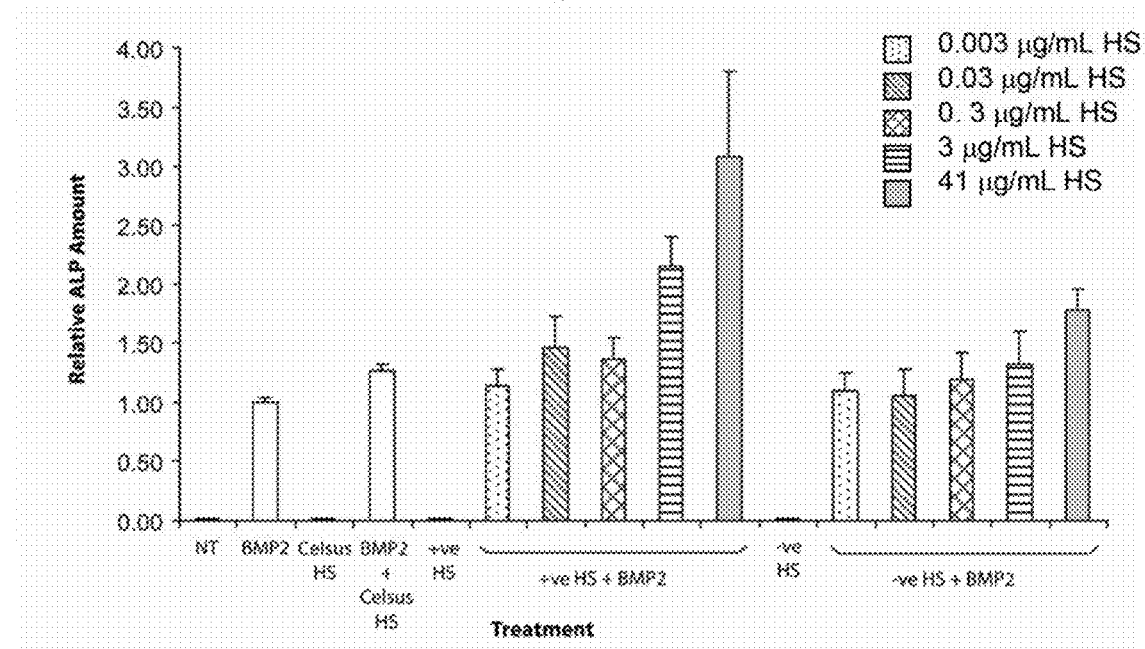

FIG. 46. Chart showing Alkaline Phosphatase (ALP) activity of BMP2 positive and BMP2 negative HS on C2C12 cells.

Figure 47:
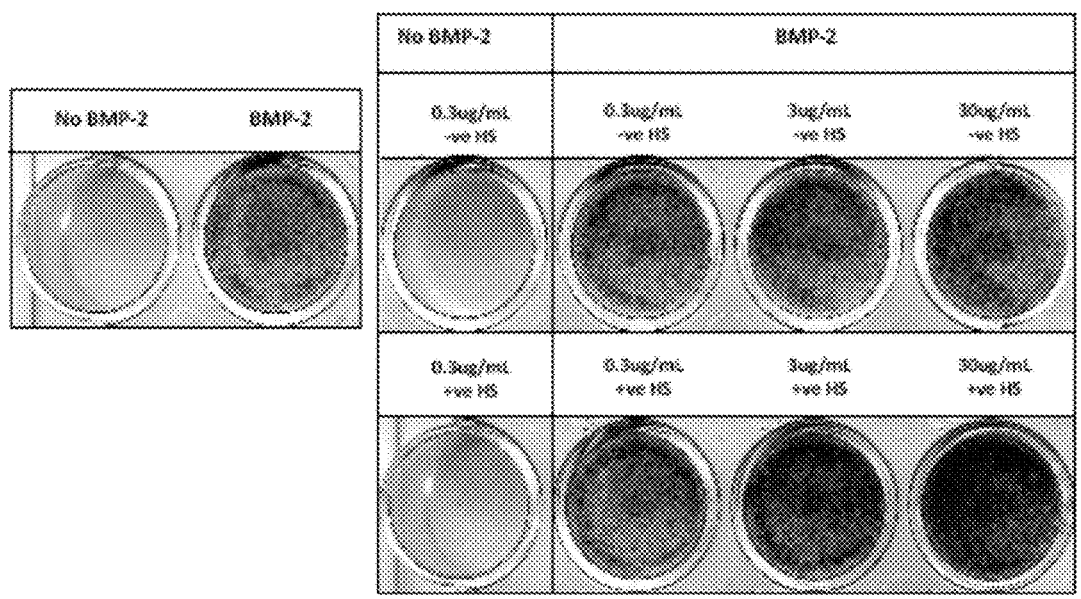

FIG. 47. Photographs of immunohistochemical analysis of HS enhancement of ALP activity. BMP2 specific HS enhanced ALP activity induced by BMP2 at a greater degree compared to non-specific HS when evaluated histochemically. BMP2 at 100 ng/ml was introduced in combination with 0, 0.3, 3 and 30 μg/ml of BMP2 positive or BMP2 negative HS.

FIG. 48. Chart showing BMP2 binding capacity of selectively (2-O, 6-O and N) de-sulfated BMP2 positive HS and indicating charge-substitution pattern of HS chains required for binding to BMP2.

FIG. 49. Chart showing effect of heparin on BMP-2 stability.

Figure 50:

FIG. 50. SEM photograph of JAX™-tricalcium phosphate bone filler, X-ray photographs of Rabbit ulna defect model. Illustration of combination with 30 μg HS/BMP2 in 200 μl hydrogel (88% water, glycerol, sodium carboxymethyl cellulose).

Figure 51:
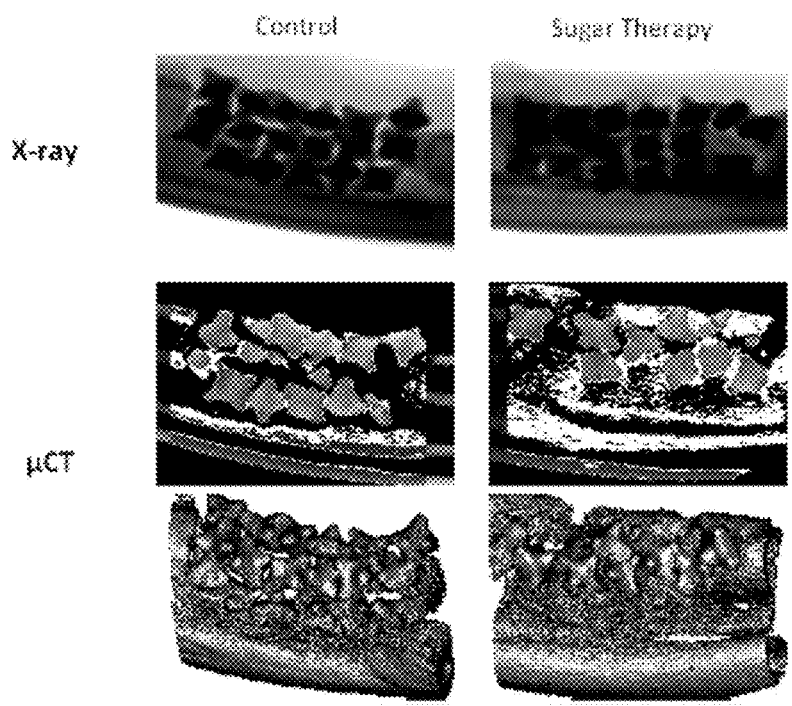

FIG. 51. X-ray and microCT scan analysis of Rabbit ulna defect model treated with JAX™ bone filler (control) or JAX™ bone filler plus HS/BMP2 at 4 weeks from treatment.

Figure 52:
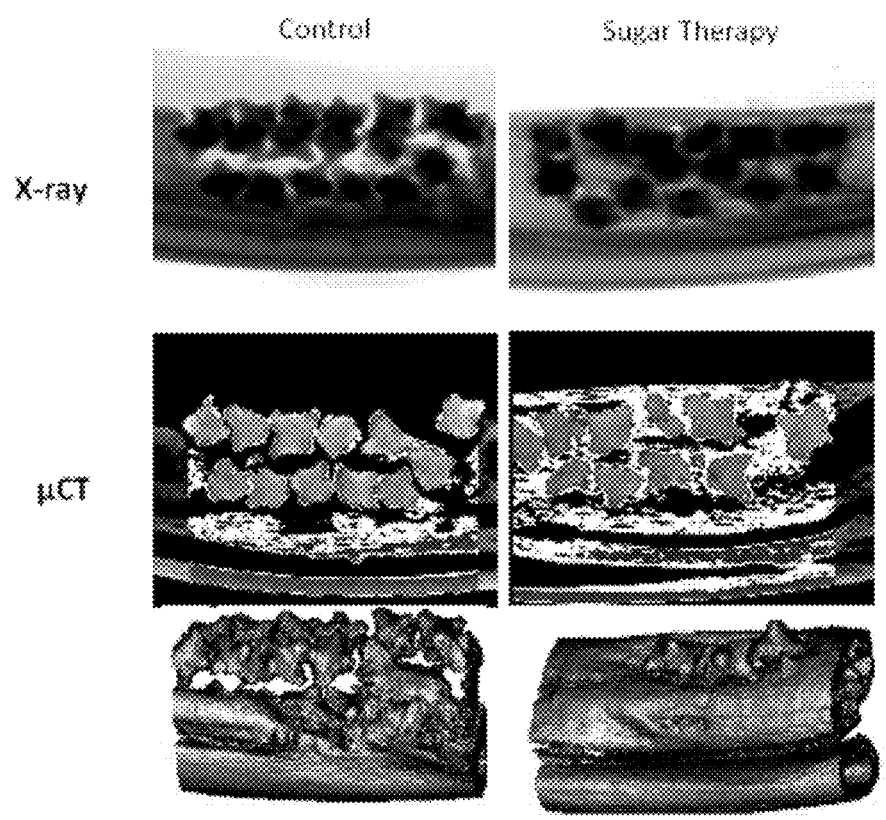

FIG. 52. X-ray and microCT scan analysis of Rabbit ulna defect model treated with JAX™ bone filler (control) or JAX™ bone filler plus HS/BMP2 at 8 weeks from treatment.

Figure 53:
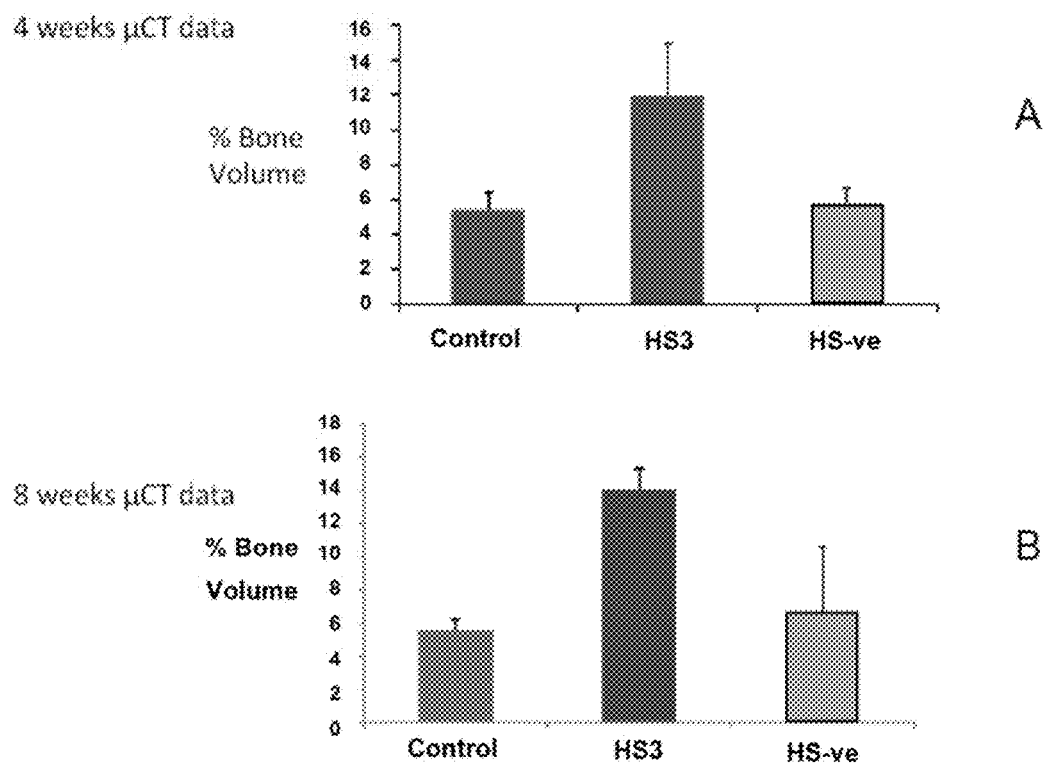

FIG. 53. Charts showing % bone volume as assessed by microCT scan in Rabbit ulna defect model treated with JAX™ bone filler (control), JAX™ bone filler plus HS/BMP2 (HS3) or JAX™ bone filler plus BMP2 negative HS at (A) 4 weeks from treatment and (B) 8 weeks from treatment.

Figure 54:
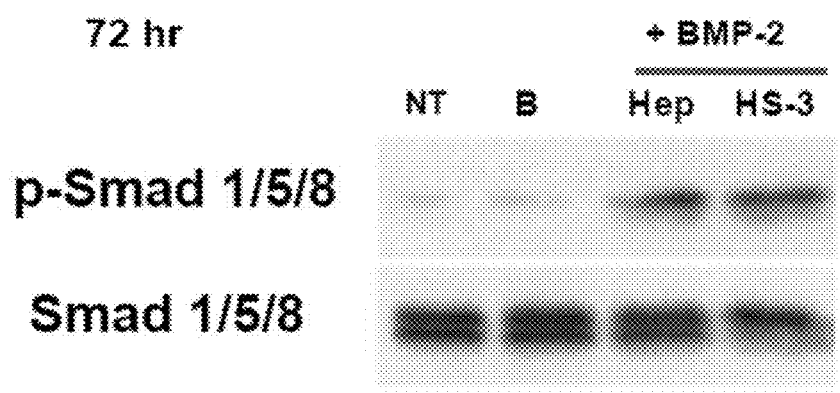

FIG. 54. Immunoblot showing levels of Smad 1/5/8 phosphorylation following exposure to negative control, BMP2 alone, BMP2+Heparin or BMP2+HS3.

Figure 55:
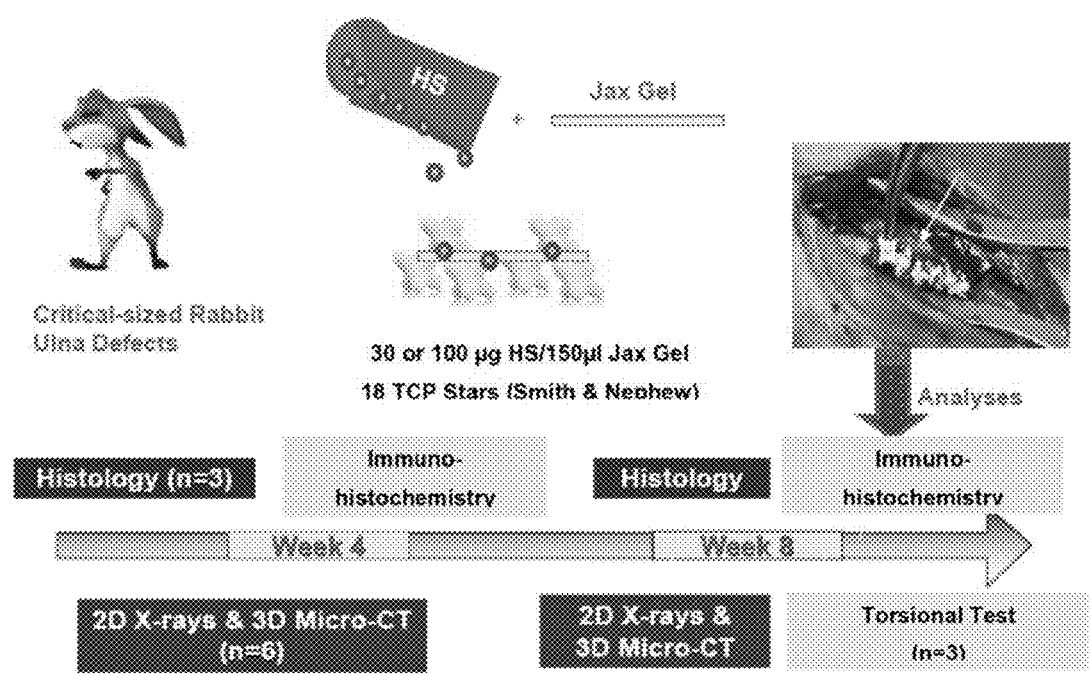

FIG. 55. Diagrammatic illustration of experimental design of non-union critical rabbit ulna defect repair.

Figure 56:
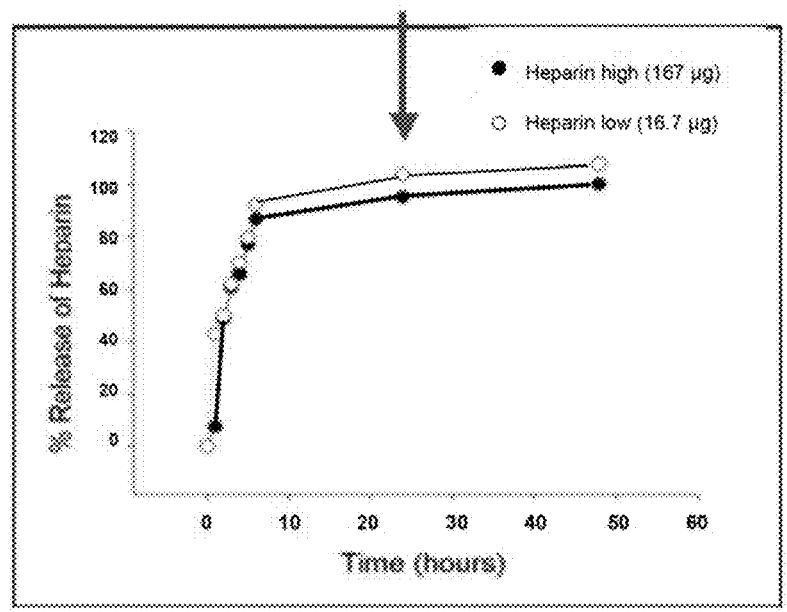

FIG. 56. Chart showing percentage release of heparin from JAX™ granules over time.

Figure 57:
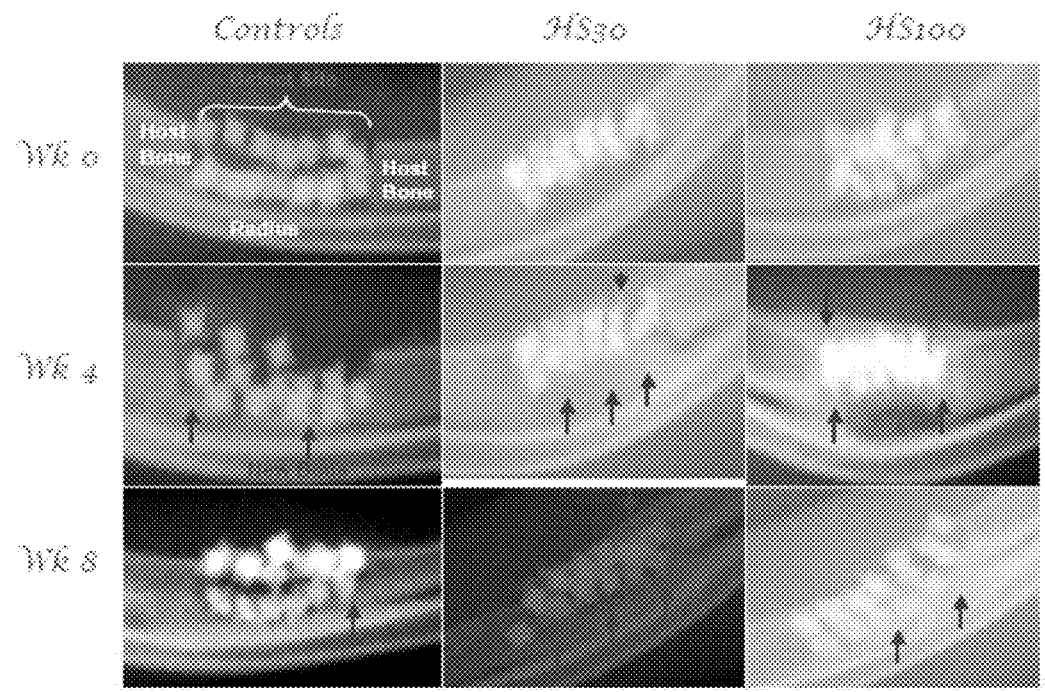

FIG. 57. X-ray micrographs showing healing rabbit ulna defect model treated with Jax™ bone filler plus control (no HS), 30 μg HS3 (HS30) or 100 μg HS3 (HS100) at weeks 0, 4 and 8.

Figure 58:
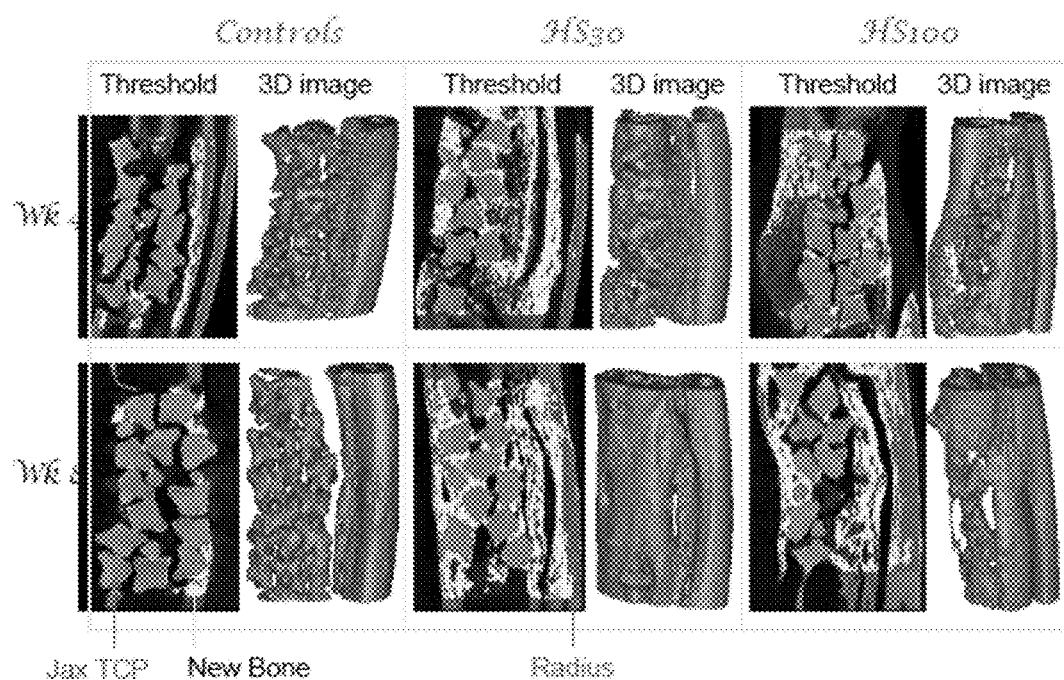

FIG. 58. Micrographs showing micro CT (computerized tomography) with 3D image rendering of the Jax stars within bone defects after 4 and 8 weeks post-surgery, compared to image-processed X-ray reconstructions (new bone in yellow). MicroCT rendered images in grey to the right of the X-ray images.

Figure 59:
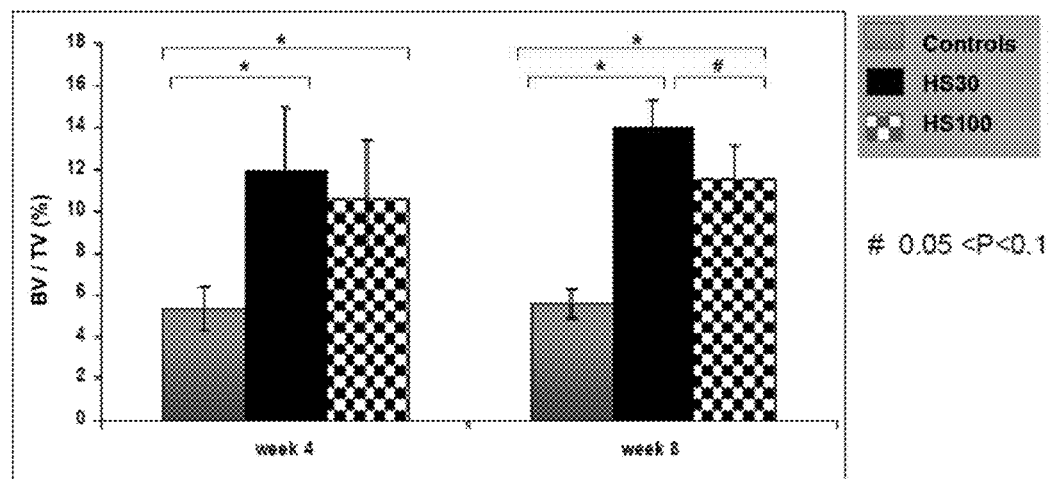

FIG. 59. Chart showing quantification of the % bone volume of total volume (BV/TV) for the treatment groups (control Vs HS30 and HS100) at weeks 4 and 8.

Figure 60:
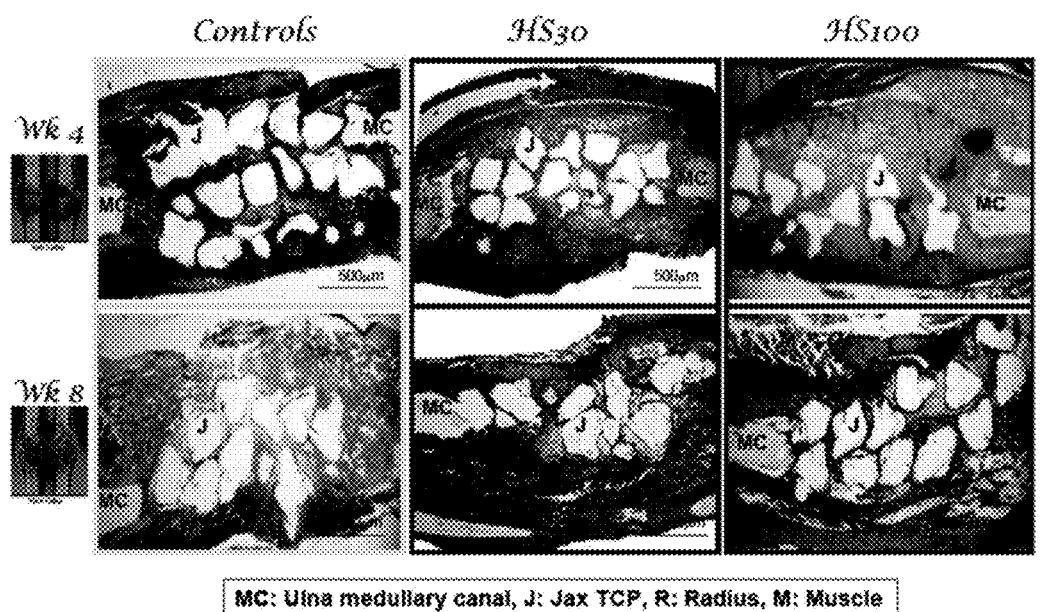

FIG. 60. Micrographs showing H&E staining (vide infra) for the 3 treatment groups (control (no HS), 30 μg HS3 (HS30) or 100 μg HS3 (HS100)) over weeks 4 and 8.

Figure 61:
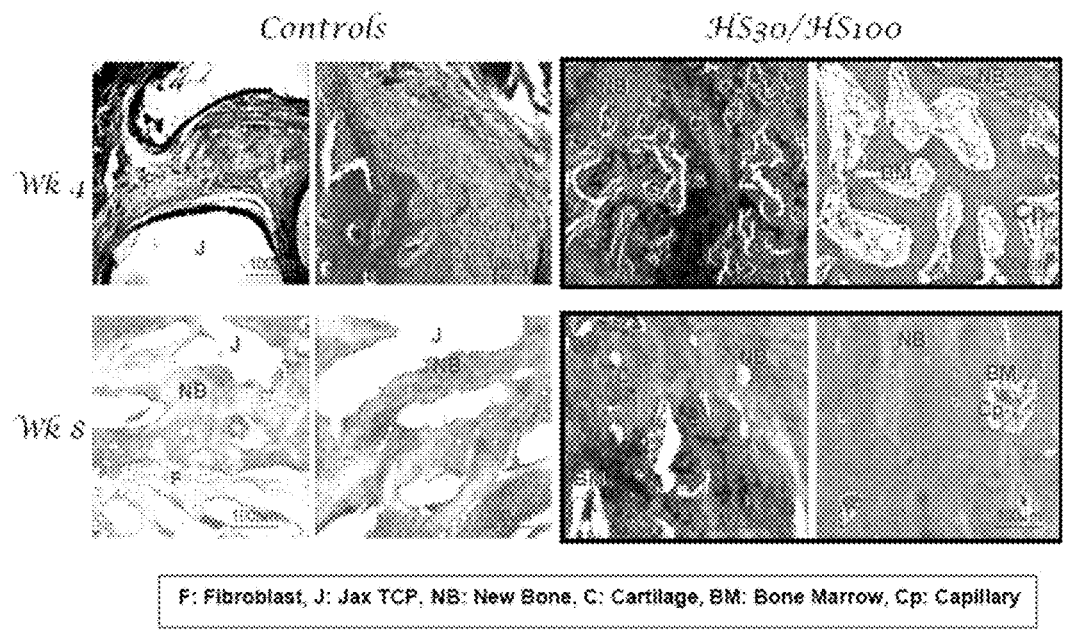

FIG. 61. Higher magnification micrographs (compared with FIG. 60) showing H&E staining for the 3 treatment groups (control (no HS), 30 μg HS3 (HS30) or 100 μg HS3 (HS100)) over weeks 4 and 8.

Figure 62:
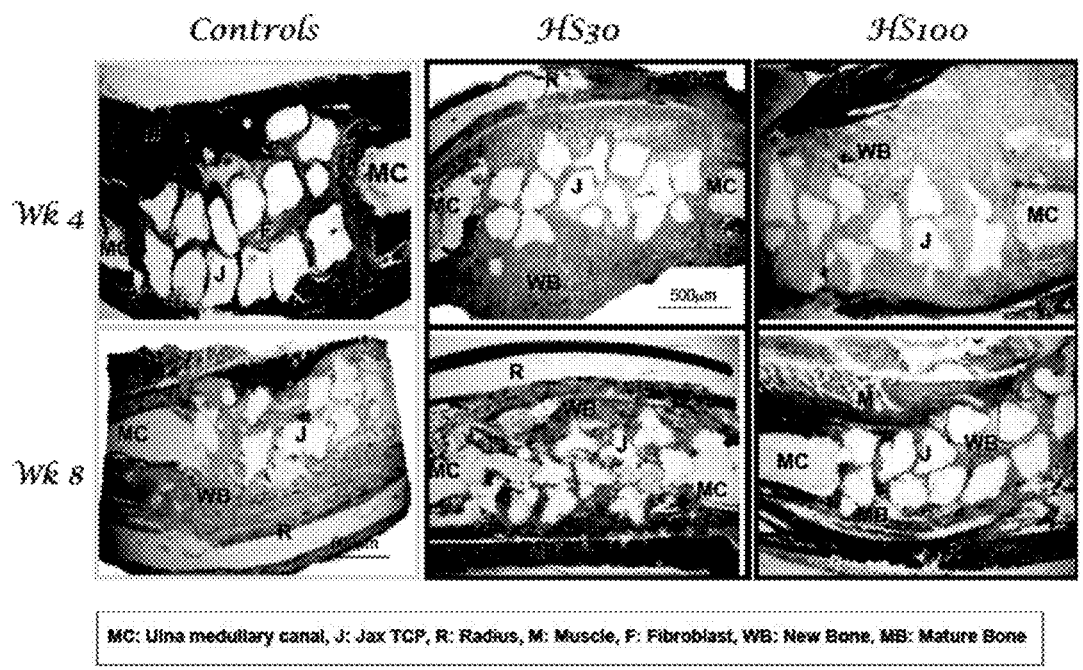

FIG. 62. Micrographs showing Ralis Tetrachrome staining (vide infra) for the 3 treatment groups (control (no HS), 30 μg HS3 (HS30) or 100 μg HS3 (HS100)) over weeks 4 and 8.

Figure 63:
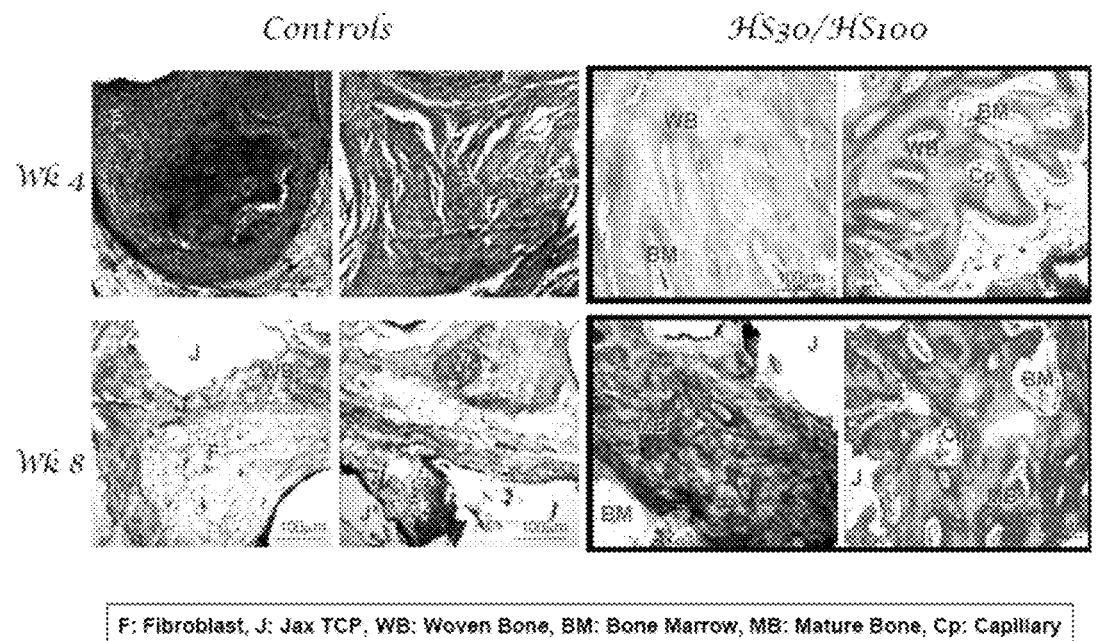

FIG. 63. Higher magnification micrographs (compared with FIG. 62) showing Ralis Tetrachrome staining for the 3 treatment groups (control (no HS), 30 μg HS3 (HS30) or 100 μg HS3 (HS100)) over weeks 4 and 8.

Figure 64:
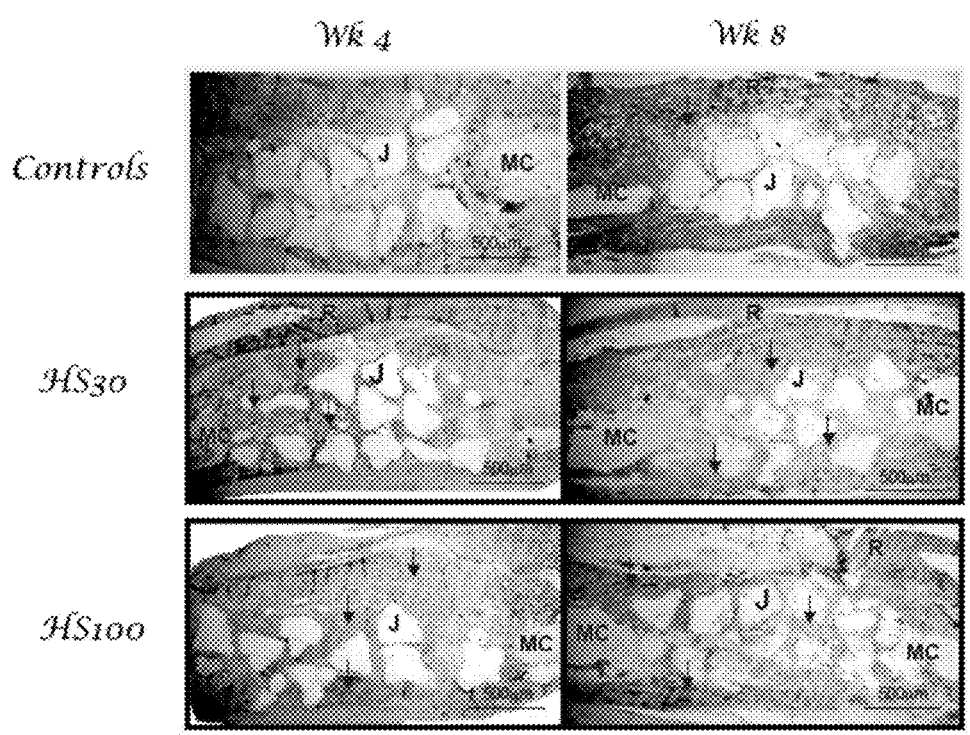

FIG. 64. Micrographs showing osteocalcin immunostaining (vide infra) for the 3 treatment groups (control (no HS), 30 μg HS3 (HS30) or 100 μg HS3 (HS100)) over weeks 4 and 8.

Figure 65:
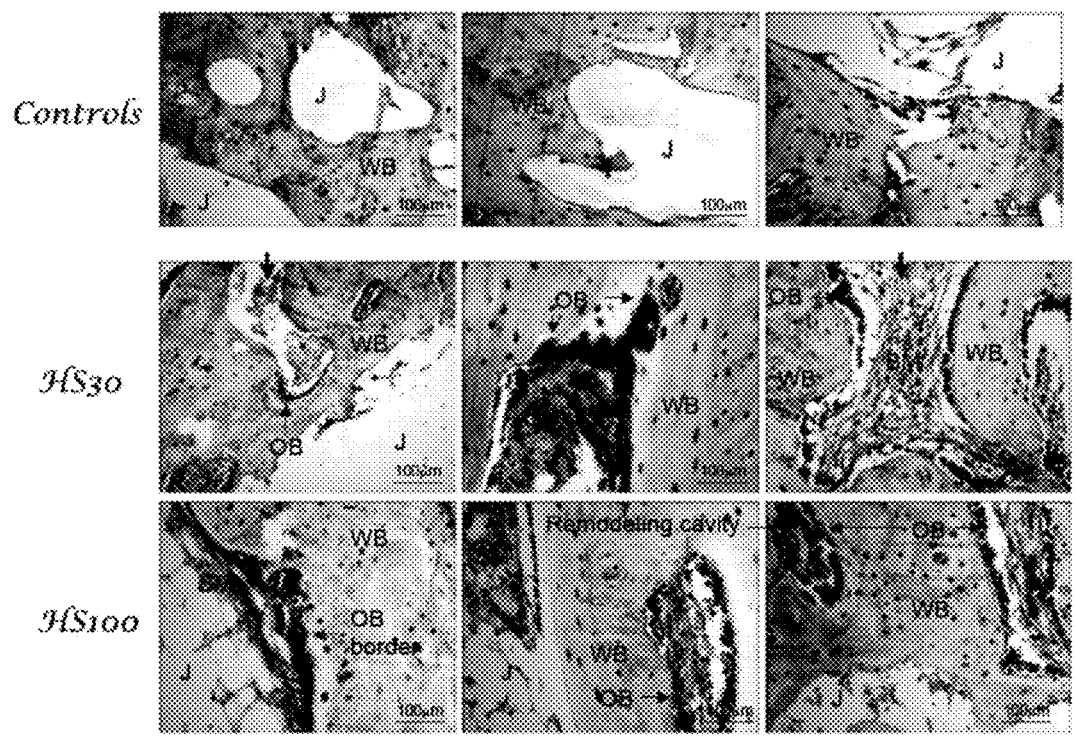

FIG. 65. Higher magnification micrographs (compared with FIG. 64) showing osteocalcin immunostaining for the 3 treatment groups (control (no HS), 30 μg HS3 (HS30) or 100 μg HS3 (HS100)) over weeks 4 and 8.

Figure 66:
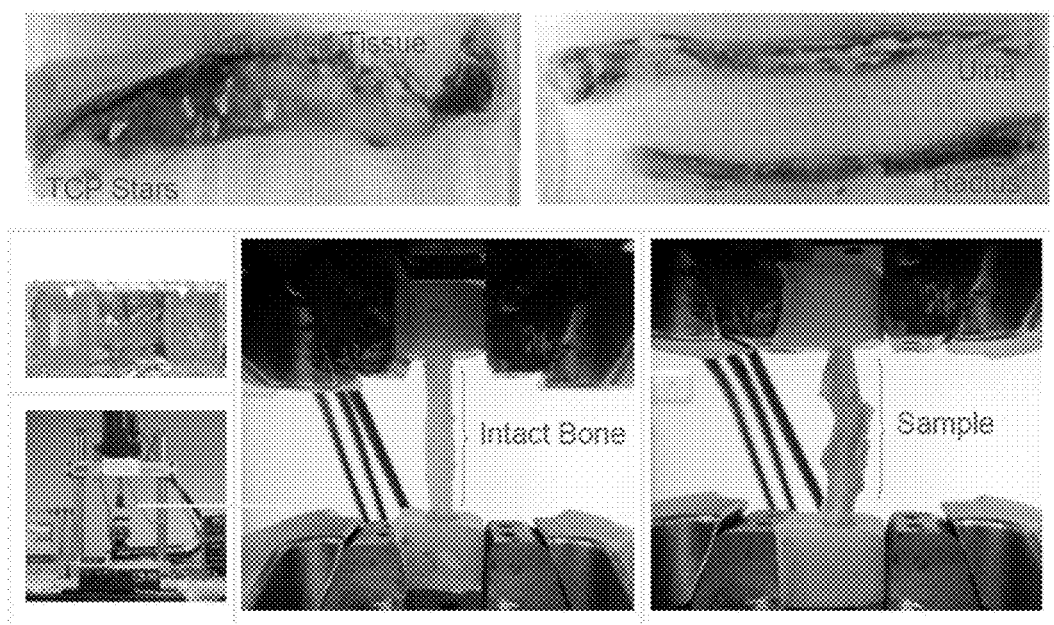

FIG. 66. Photographic illustration of torsional testing apparatus.

Figure 67:
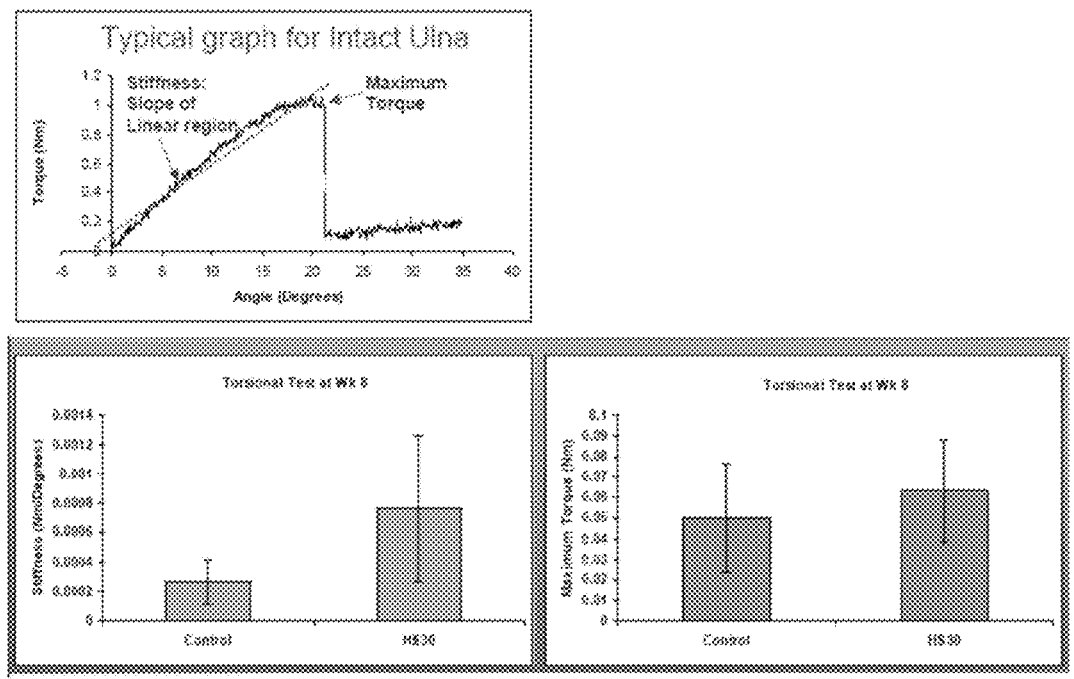

FIG. 67. Charts showing typical torsion vs. angle for intact ulna, plus stiffness and maximum torque for HS30 at week 8.

Figure 68:
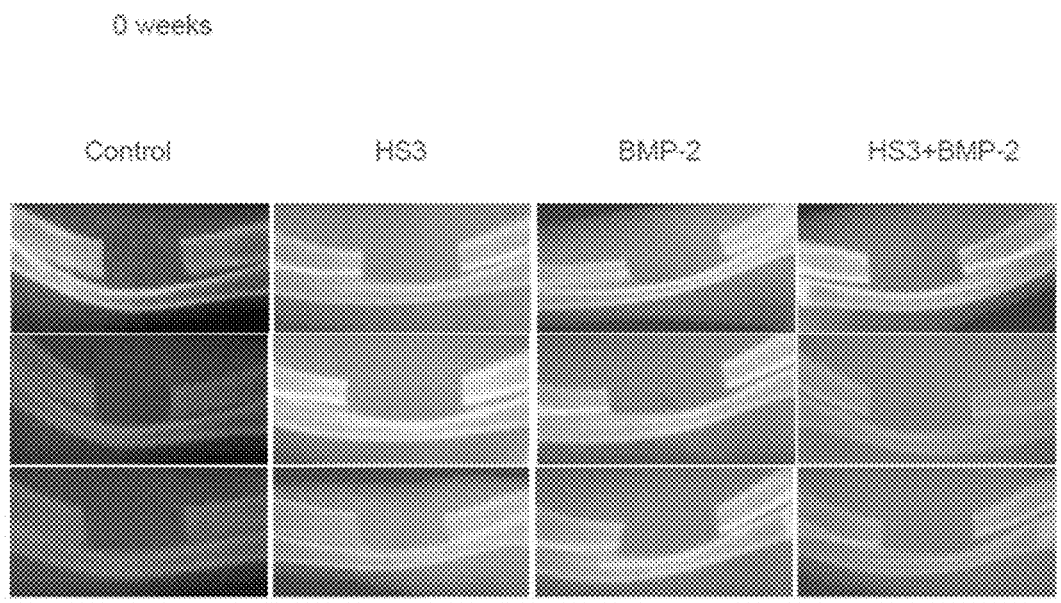

FIG. 68. X-ray micrographs at 0 weeks showing rabbit ulna defect model treated with collagen sponges soaked with one of the following treatments (total 300 μL, in PBS): 30 μg HS3, 10 μg BMP-2, 30 μg HS3+10 μg BMP-2 or an equal volume of PBS.

Figure 69:
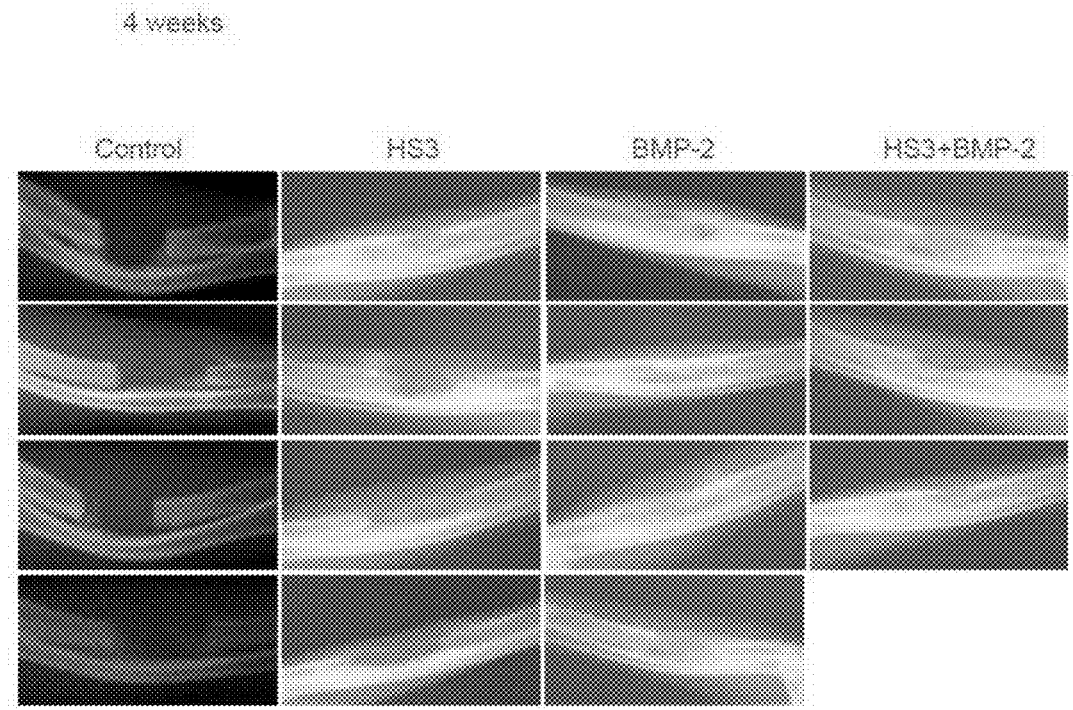

FIG. 69. X-ray micrographs at 4 weeks showing healing in rabbit ulna defect model treated with collagen sponges soaked with one of the following treatments (total 300 μL, in PBS): 30 μg HS3, 10 μg BMP-2, 30 μg HS3+10 μg BMP-2 or an equal volume of PBS.

Figure 70:
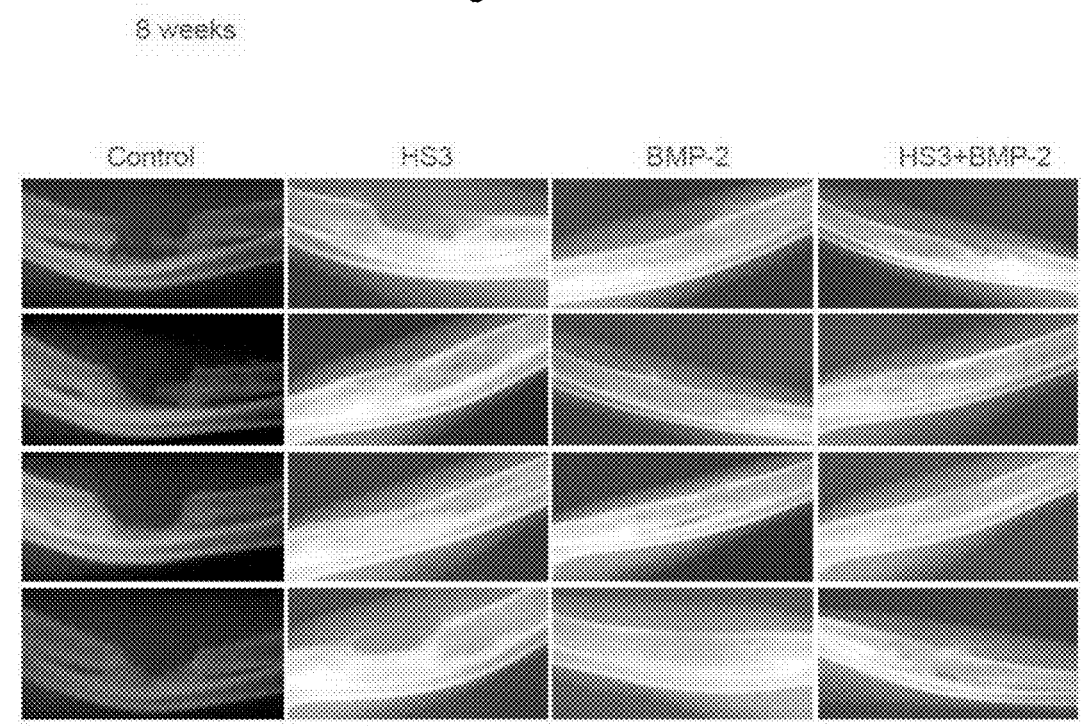

FIG. 70. X-ray micrographs at 8 weeks showing healing in rabbit ulna defect model treated with collagen sponges soaked with one of the following treatments (total 300 μL, in PBS): 30 μg HS3, 10 μg BMP-2, 30 μg HS3+10 μg BMP-2 or an equal volume of PBS.

Figure 71:
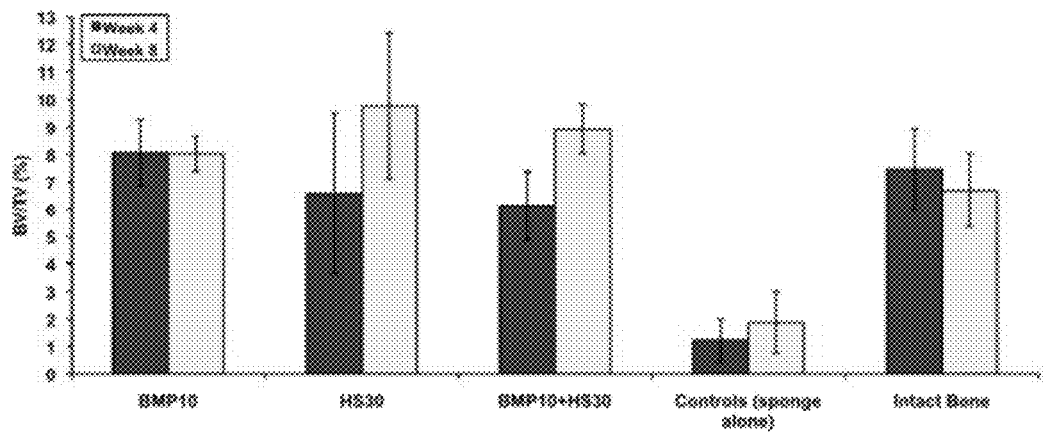

FIG. 71. Chart showing micro CT analysis at 4 and 8 weeks for rabbit ulna defect model treated with collagen sponges soaked with one of the following treatments (total 300 μL, in PBS): 30 μg HS3, 10 μg BMP-2, 30 μg HS3+10 μg BMP-2 or an equal volume of PBS.

Figure 72:
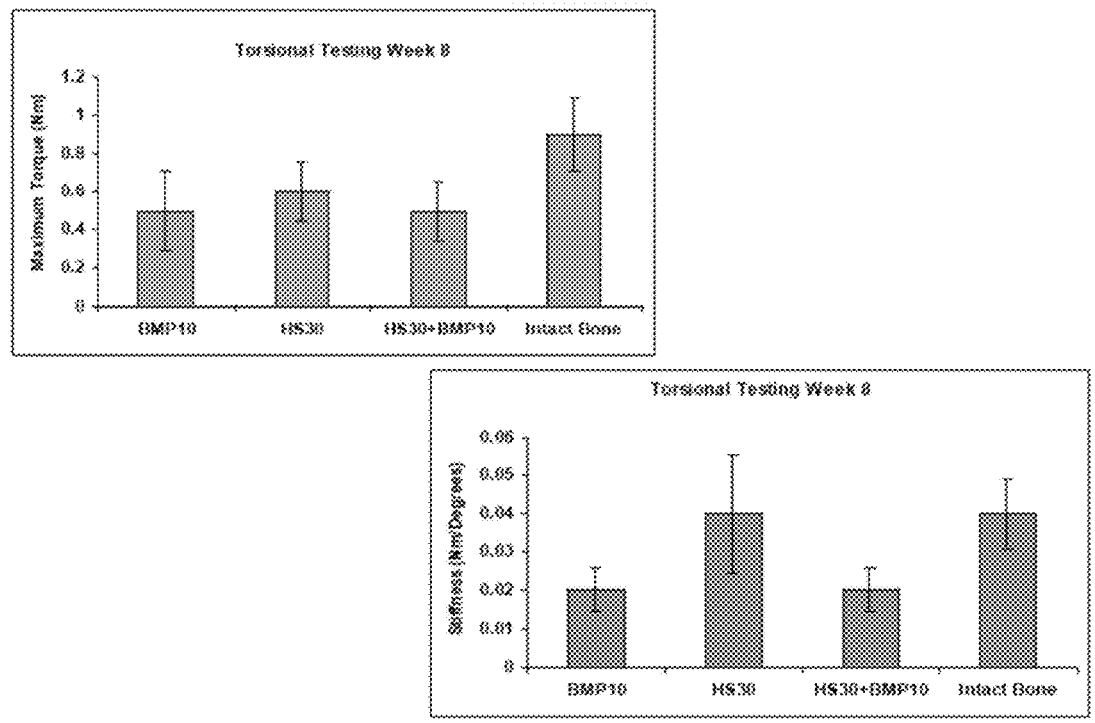

FIG. 72. Charts showing maximum torque and stiffness at week 8 for rabbit ulna defect model treated with collagen sponges soaked with one of the following treatments (total 300 μL, in PBS): 30 μg HS3, 10 μg BMP-2, 30 μg HS3+10 μg BMP-2 or an equal volume of PBS.

Figure 73:
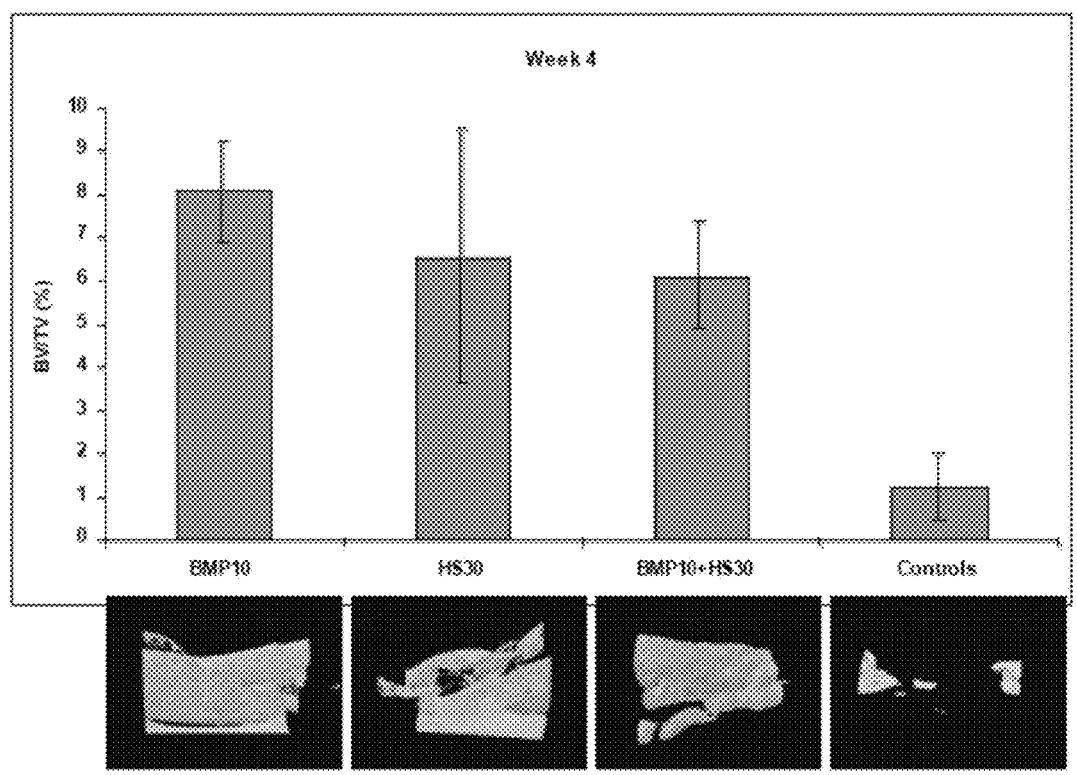

FIG. 73. Chart and micro CT image showing percentage bone volume at week 4 for rabbit ulna defect model treated with collagen sponges soaked with one of the following treatments (total 300 μL, in PBS): 30 μg HS3, 10 μg BMP-2, 30 μg HS3+10 μg BMP-2 or an equal volume of PBS.

Figure 74:
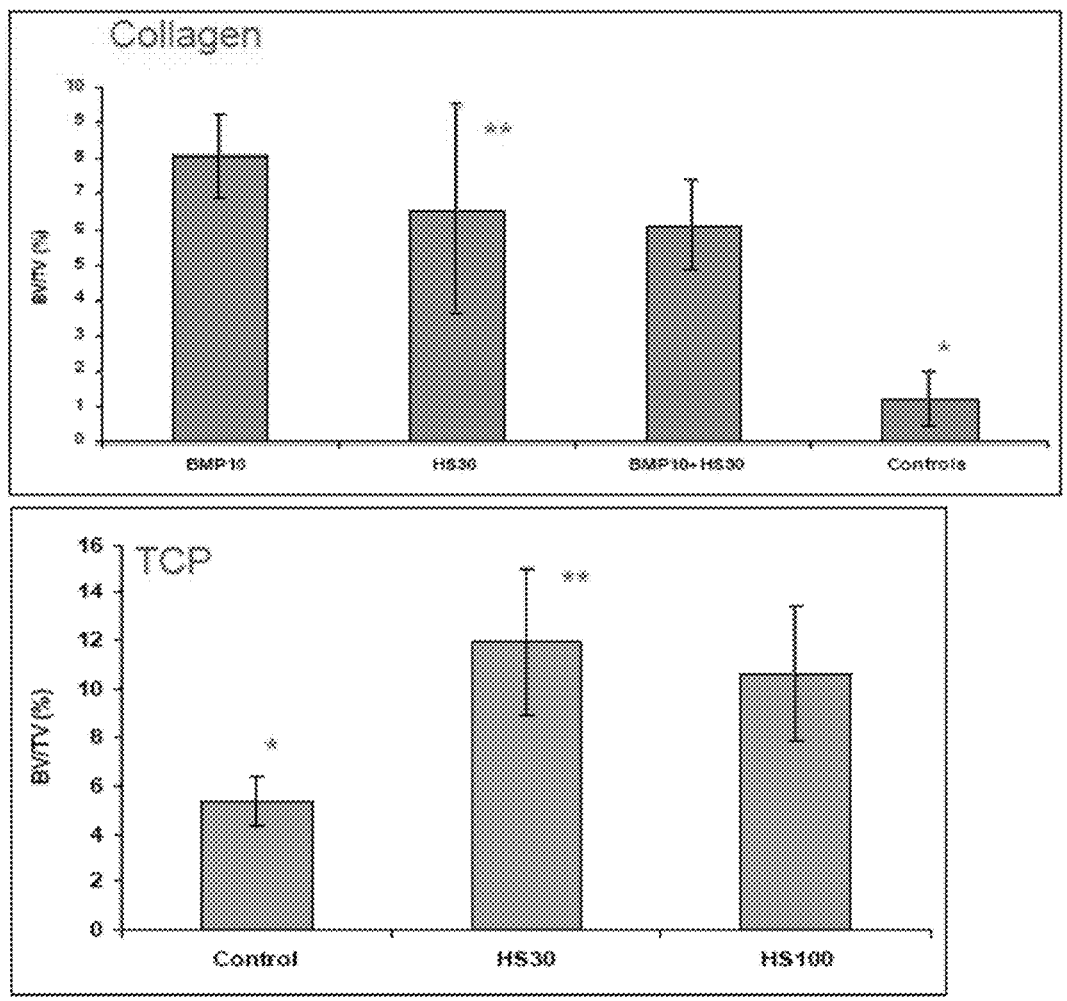

FIG. 74. Charts showing comparison at week 4 of percentage bone volume in the rabbit ulna defect model between treatment with Jax™ TCP stars and collagen sponges when combined with one of 10 μg BMP-2 (BMP10), 30 μg HS3 (HS30), 10 μg BMP-2+30 μg HS3, 100 μg HS3 (HS100) or control.

DETAILED DESCRIPTION OF THE INVENTION

The details of one or more embodiments of the invention are set forth in the accompanying description below including specific details of the best mode contemplated by the inventors for carrying out the invention, by way of example. It will be apparent to one skilled in the art that the present invention may be practiced without limitation to these specific details.

We investigated the potential of GAGs to augment the activities of bone morphogenic protein 2 (BMP2). The highly osteoinductive activity of BMP2 for the murine myogenic cell line C2C12 have been well characterised. Studies both in this cell line, and in vivo, have implicated a role for glycosaminoglycans in modulating this activity.

BMP2's affinity for heparin has similarly been well characterised. Numerous studies have been conducted that have sought to examine the dynamic interaction between BMP2 and GAGs. Some have proposed that the interaction is inhibitory, and so responsible for either sequestering the cytokine away from the receptor or inducing its association with its numerous inhibitors, such as noggin, that have been shown, similarly, to have an affinity for heparin. Alternative findings implicate the interaction between BMP2 and GAGs is one of maintaining a local concentration of the cytokine around cells that require its signalling in order to differentiate into the osteoblast lineage.

These findings also suggest that the association serves to significantly lengthen the half-life of the homodimer, so allowing it to remain active in the ECM for longer periods. As is the case with most systems, the actual role of this interaction is likely to be blend of some, or all of the above.

Although many studies have provided evidence for the interaction that BMP2 has with model sugars, the specific interaction between the BMP2 heparin-binding peptide (BMP2-HBP), a string of amino acids (QAKH-KQRKRLKSSCKRHP [SEQ ID NO: 1]) located at the N-terminal end of each BMP2 monomer, and appropriate glycosaminoglycans has received relatively little attention. A major question that arises is whether there is a complementary saccharide sequence embedded within an HS chain that controls the association with an absolute, or at least relative, specificity.

We sought to isolate a sequence-specific glycosaminoglycan that could modulate BMP2 activity via a direct interaction with the cytokine.

Example 1

Materials and Methods

Buffer Preparation

Preparation of all buffers for GAG extraction and analysis is conducted with strict attention paid to quality. It is vital that the pH of buffers is maintained at the correct level and that all buffers be filtered and degassed in order to prevent the clogging of columns with precipitates or bubbles. The formation of bubbles, in particular, can cause serious damage to columns, and in the case of sealed, pre-fabricated columns, leads to them becoming unusable.

All buffers used were filtered with 1×PBS without $Ca^{2+}$ or $Mg^{2+}$ (150 mM NaCl), or double distilled (dd$H_2$O) to make the final solutions.

Disruption Buffer

The 8M Urea/CHAPS disruption buffer consisted of PBS (150 mM NaCl) with 1% CHAPS, 8M Urea and 0.02% Na$N_3$ to prevent contamination by microbial growth during storage. This solution was used to disrupt matrix (MX) samples, so was not degassed or filtered.

PGAG Anion Exchange Low Salt (250 mM) Buffer

Low salt PGAG anion exchange buffer comprised PBS (150 mM NaCl) with an additional 100 mM NaCl. The buffer was equilibrated to pH 7.3 with NaOH and 0.02% Na$N_3$. The solution was then degassed under negative pressure and constant stirring until no further bubbles were released before being filtered through a 0.4 μm filter.

PGAG Anion Exchange High Salt (1M) Buffer

High salt PGAG anion exchange buffer comprised PBS (150 mM NaCl) with an additional 850 mM NaCl. The buffer was equilibrated to pH 7.3 with NaOH and 0.02% $NaN_3$ added. The solution was then degassed under negative pressure and constant stirring before being filtered through a 0.4 μm filter.

Pronase/Neuraminidase PGAG Reconstitution Buffer

This buffer was used to reconstitute desalted PGAG samples after anion exchange in order to prepare them for enzymatic digestion of the associated core proteins. It consisted of 25 mM sodium acetate ($CH_3COOHNa$). The buffer was equilibrated to pH 5.0 with glacial acetic acid ($CH_3COOH$). Both pronase and neuraminidase enzymes were reconstituted according to the manufacturer's instructions.

GAG Affinity Chromatography Low Salt (150 mM) Buffer

Low salt GAG anion exchange buffer was made using PBS (150 mM NaCl) without any additional salt. The buffer was equilibrated to pH 7.3 with NaOH and 0.02% $NaN_3$. The solution was degassed under negative pressure and constant stirring until no further bubbles were released before being filtered through a 0.4 μm filter.

GAG Affinity Chromatography High Salt (1M) Buffer

High salt GAG anion exchange buffer was made using PBS (150 mM NaCl) with an additional 850 mM NaCl. The buffer was equilibrated to pH 7.3 with NaOH and 0.02% $NaN_3$ was added, the solution was then degassed and filtered through a 0.4 μm filter.

Desalting Solution

The desalting solution was made using $ddH_2O$ that was equilibrated to pH 7.0 with 0.02% $NaN_3$. The solution was then degassed and filtered.

Sample Preparation

Matrix samples were disrupted using Disruption Buffer (8M Urea/CHAPS), then scraped off the culture surface in this buffer and stirred overnight at 37° C. to ensure maximal lysis. The samples were then centrifuged at 5000 g for 30 min and the supernatant was clarified through a 0.4 μm filter in preparation for PGAG extraction via anion exchange chromatography.

Column Preparation & Usage

The choice and preparation of the types of columns to be used for each sequential step in the isolation and characterisation of GAGs is of major importance for the success of the protocol. It was vital that at each step the columns were equilibrated and cleaned with great care.

Anion Exchange Columns

Due to the relatively large quantities of MX substrate used for GAG extraction, and the high load this places on the column system, it was necessary to pack and prepare a large anion exchange column manually, specifically for this study. Capto Q anion exchange beads (Pharmacia) were packed into a Pharmacia XK 26 column (Pharmacia) to produce a column with a maximum loading capacity of 500 ml of MX lysate per run.

Prior to use, both the column and all buffers were equilibrated to room temperature for 30 min, before washing and equilibrating the column in PGAG Anion Exchange Low Salt (250 mM) Buffer for 30 min until all absorbance channels remained stable. The clarified cell lysate was then passed through the column which was again rinsed in 500 ml of low salt buffer to remove any nonspecifically bound debris. PGAGs were then eluted using 250 ml of PGAG Anion Exchange High Salt (1M) Buffer and lyophilised prior to desalting. The column was then rinsed in low salt buffer and returned to 4° C. for storage.

Desalting Protocol

After PGAG/GAG isolation it was necessary to remove the high amount of salt that accumulated in the sample during elution from the column. For this step, all eluted samples of the same experimental group were combined and loaded onto 4× Pharmacia HiPrep™ 26/10 desalting columns. Prior to use, both the columns and all solutions were equilibrated to room temperature for 30 min before washing and equilibrating the column in Desalting Solution for 30 min until all absorbance channels achieved stability. Lyophilised samples were reconstituted in Desalting Solution in the minimum possible volume that resulted in a clear solution. This combination of columns permitted the loading of up to 60 ml of sample. Those fractions eluting from the column first were lyophilised and retained for further separation or cell culture application. The columns were then rinsed in Desalting Solution and returned to 4° C. for storage.

BMP2-HBP Column Preparation

The isolation of GAGs carrying relative affinities for BMP2 was conducted using a BMP2-HBP column. Approximately 2 mg of biotinylated BMP2-HBP was prepared in 1 ml of the GAG Affinity Chromatography Low Salt (150 mM) Buffer. This amount was loaded onto a HiTrap Streptavidin HP column (Pharmacia) and allowed to attach to the column for 5 min. The column was then subjected to a complete run cycle in the absence of GAGs. The column was washed in 13 ml of low salt buffer at a flow rate of 0.5 ml/min before being subjected to 10 ml of GAG High salt buffer at 1 ml/min. Finally the column was rinsed with 10 ml of low salt buffer. During this process data was carefully monitored to ensure that no peptide elution or column degradation was observed.

GAG+ Sample Isolation

Once the BMP2-HBP column had been prepared and tested for stability under normal running conditions, it was ready to be used for the separation of GAG+ chains from tGAG (total GAG) samples. tGAG samples (6 mg) were prepared in 3 ml of GAG affinity low salt (150 mM) buffer and injected into a static loop for loading onto the column. Prior to use both the BMP2-HBP column and all buffers were equilibrated to room temperature for 30 min before washing and equilibrating the column in low salt buffer for 30 min until all absorbance channels were stable. The sample was then loaded onto the column at 0.5 ml/min and the column and the sample rinsed in 10 ml of low salt buffer at 0.5 ml/min. Retained GAG+ samples were subsequently recovered by elution with 10 ml of high salt (1 M) buffer and lyophilised for desalting. The column was then rinsed in 10 ml of low salt buffer and stored at 4° C.

Pronase/Neuraminidase Treatment

In order to isolate GAG chains from their core proteins, they were digested using pronase and neuraminidase. Lyophilized PGAG samples were resuspended in a minimum volume of 25 mM sodium acetate (pH 5.0) and clarified by filtration through a 0.4 μm syringe filter. Total sample volume was dispensed into 10 ml glass tubes in 500 μl aliquots. 500 μl of 1 mg/ml neuraminidase was added and incubated for 4 h at 37° C. After incubation 5 ml of 100 mM Tris-acetate (pH 8.0) was added to each sample. An additional 1.2 ml of 10 mg/ml pronase, reconstituted in 500 mM Tris-acetate, 50 mM calcium acetate (pH 8.0), was added to each sample and incubated for 24 h at 36° C. After treatment all volumes were combined and prepared for anion exchange processing by centrifugation and filtration.

GAG Digestion Protocols

The analysis of GAGs, including their sulfated domain sizes and relative sulfation levels, was carried out by using established protocols including degradation by either nitrous acid or lyases.

Nitrous Acid Digestion

Nitrous acid-based depolymerisation of heparan sulfate leads to the eventual degradation of the carbohydrate chain into its individual disaccharide components when taken to completion. Nitrous acid was prepared by chilling 250 µl of 0.5 M $H_2SO_4$ and 0.5 M $Ba(NO_2)_2$ separately on ice for 15 min. After cooling, the $Ba(NO_2)_2$ was combined with the $H_2SO_4$ and vortexed before being centrifuged to remove the barium sulfate precipitate. 125 µl of $HNO_2$ was added to GAG samples resuspended in 20 µl of $H_2O$, and vortexed before being incubated for 15 min at 25° C. with occasional mixing. After incubation, 1 M $Na_2CO_3$ was added to the sample to bring it to pH 6. Next, 100 µl of 0.25 M $NaBH_4$ in 0.1 M NaOH was added to the sample and the mixture was heated to 50° C. for 20 min. The mixture was then cooled to 25° C. and acidified with glacial acetic acid to pH 3 in the fume hood. The mixture was then neutralised with 10 M NaOH and the volume was then decreased by freeze drying. The final samples were run on a Bio-Gel P-2 column to separate di- and tetrasaccharides to verify degradation.

Heparinase III Digestion

Heparinase III is an enzyme that cleaves sugar chains at glucuronidic linkages. The series of heparinase enzymes (I, II and III) each display relatively specific activity by depolymerising certain heparan sulfate sequences at particular sulfation recognition sites. Heparinase I cleaves HS chains within NS regions along the chain. This leads to the disruption of the sulfated domains that are thought to carry most of the biological activity of HS. Heparinase III depolymerises HS within the NA domains, resulting in the separation of the carbohydrate chain into individual sulfated domains. Lastly, Heparinase II primarily cleaves in the NA/NS "shoulder" domains of HS chains, where varying sulfation patterns are found.

In order to isolate potential active domains we focused on the depolymerisation of GAG+NA regions. Both the enzyme and lyophilised HS samples were prepared in a buffer containing 20 mM Tris-HCl, 0.1 mg/ml BSA and 4 mM $CaCl_2$ at pH 7.5. The concentration of heparinase III added to each sample is governed by the relative quantity of HS components in the sample. Our analysis, via nitrous acid depolymerisation, indicated that the GAG+ samples consisted of predominantly HS; thus the enzyme was used at 5 mU per 1 µg of HS. The sample was incubated at 37° C. for 16 h before the reaction was stopped by heating to 70° C. for 5 min. The sample was then applied to the appropriate column system for further analysis.

Cell Culture

GAG Production

In order to isolate GAG species representative of developing osteoblasts, MC3T3 cells were grown in osteogenic conditions for 8 days. The cellular component was removed via incubation in a dilute solution of 0.02 M ammonium hydroxide ($NH_4OH$) at 25° C. for 5 min. After 5 min, $NH_4OH$ was removed by inversion of the culture surfaces. Treated cultures were allowed to dry in a laminar flow cabinet overnight. The following day the treated cultures were washed three times with sterile PBS and allowed to dry in the laminar flow cabinet. Prepared matrix cultures were then stored under sterile conditions in 4° C. until primary proteoglycans were liberated via treatment with disruption buffer and anion exchange chromatography.

BMP2-Specific GAG Bioactivity

C2C12 myoblasts were subcultured every 48 h, to a maximum of 15 passages, by plating at $1.3 \times 10^4$ cells/$cm^2$ in Dulbecco's modified Eagle's medium (DMEM) supplemented with 10% FCS. Osteogenic differentiation was induced at $2 \times 10^4$ cells/$cm^2$ in DMEM supplemented with 5% FCS, nominated concentrations of recombinant human bone morphogenic protein-2 (rhBMP2) and glycosaminoglycan fractions with a positive or negative affinity for rhBMP2 (GAG+ and GAG− respectively). rhBMP2 and GAG fractions were pre-incubated for 30 min at 25° C. prior to addition to their corresponding C2C12 cultures. The cultures were permitted to grow under these conditions for 5 days, with media for each condition being changed every 48 h, before mRNA samples were extracted and prepared for RQ-PCR analysis. Real time PCR for osteocalcin expression was conduced using the ABI Prism 7000® sequence detection system (PerkinElmer Life Sciences). Primers and probes were designed using Primer Express software (v2.1, PE Applied Biosystems). The target probe was redesigned to incorporate LNA bases and labelled with BHQ-1 (Sigma-Proligo). The ribosomal subunit gene 18S (VIC/TAMRA) was used as an endogenous control, with each condition consisting of three repeats, each tested in triplicate. The raw PCR data was analysed using the ABI Sequence Detector software. Target gene expression values were normalised to 18S expression prior to the calculation of relative expression units (REUs).

Results

Anion Exchange Chromatography

In order to successfully extract GAGs from MX samples, it is necessary to remove other matrix proteins that may contaminate the sample. As GAGs constitute the most negatively charged molecules in the ECM, this is most effectively accomplished with anion exchange chromatography.

Figure 1:
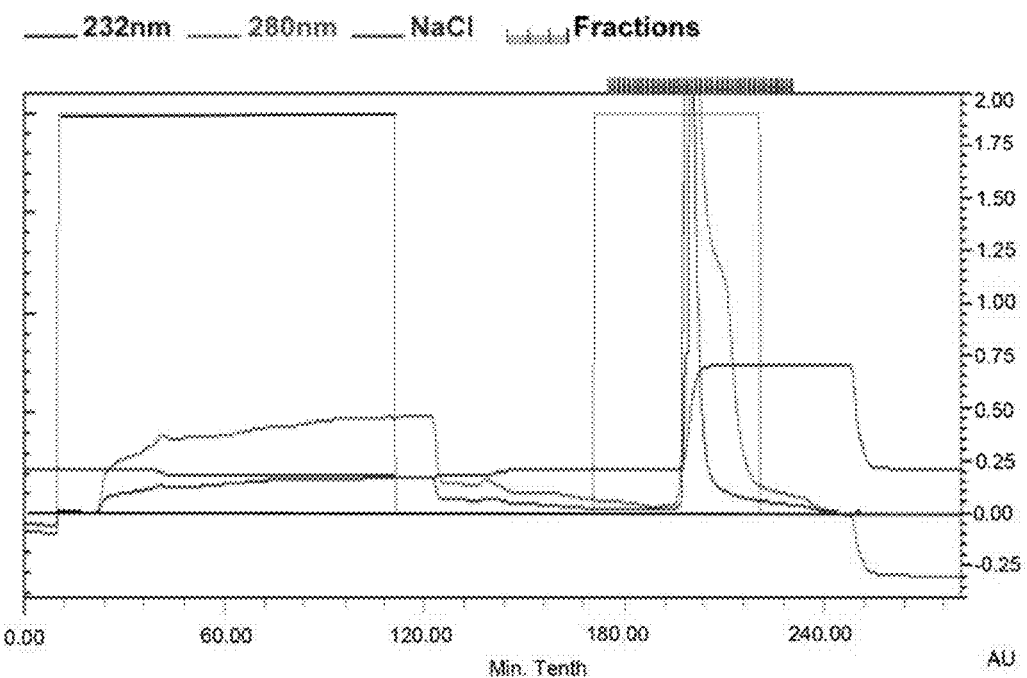
FIG. 1. Anion exchange chromatography of MX samples disrupted using 8 M Urea/CHAPS buffer. A large GAG peak is observed after 1M NaCl elution.

Samples were disrupted using 8M Urea/CHAPS buffer and loaded onto the anion exchange column. Unwanted protein and ECM debris were washed from the column and the negatively charged GAGs eluted with 1 M NaCl. A typical chromatogram (FIG. 1) clearly shows the flowthrough of a large amount of nonadherent debris, as well as the clean and tight elution of a large quantity of GAGs from the MX preparation. Thus not only does this result demonstrate the purification of GAGs by this method, it also confirms the retention of a large number of GAGs in the ECM after treatment with $NH_4OH$.

Desalting

Figure 2:
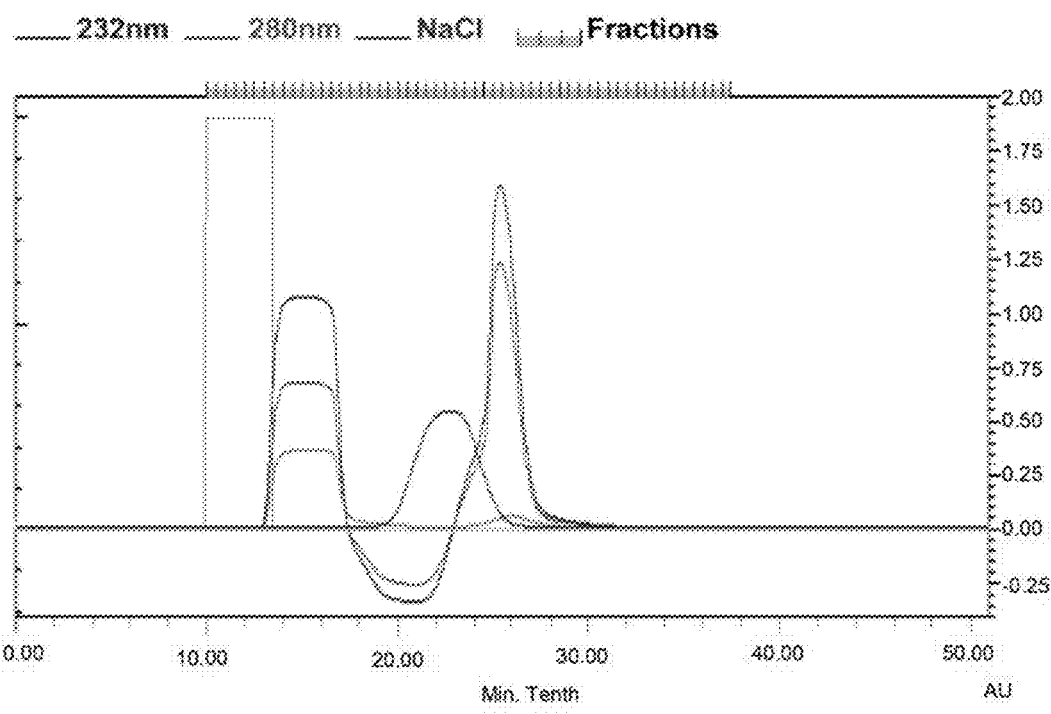
FIG. 2. Representative chromatogram of the desalting system during MX-derived GAG purification. The initial peak (12-18 min) represents full length GAG chains. The conductivity peak and debris peak (19-30 min) represent salt and GAG debris elution.

Virtually all chromatography methods employed to purify and analyse GAGs at various stages of processing require elution with high-salt buffers. As high salt conditions interfere with affinity-based chromatography, it is necessary to desalt samples after each stage of processing. This process is generally completed with size exclusion chromatography. Under these conditions larger molecules, such as GAGs, exit the column before small molecules, including the salt and small GAG debris. The separation of GAGs from the contaminating salt can be followed on the resulting chromatogram (FIG. 2) which also serves to confirm that the GAG chains remained intact during the treatment process.

BMP2-HBP Column System

Column Preparation

Due to the prohibitive costs involved in creating a BMP2 growth factor column with commercially available reagents, we instead utilised a biotinylated preparation of the known heparin-binding domain of BMP2 (BMP2-HBP). This peptide was immobilised on a Hi-Trap Streptavidin HP column (1 ml) in order to specifically retain GAG chains with an affinity for the specific heparin-binding domain peptide.

First we examined any background affinity the GAGs may have had for the naked streptavidin column by running the total GAG (tGAG) fraction against a column bed devoid of BMP2-HBP (FIG. 3). Our results confirmed that our MX derived tGAG samples carried no inherent affinity for the streptavidin column. We further investigated two separate methods of exposing tGAGs to the BMP2-HBP for the purpose of separating chains with a specific affinity. The peptide was either pre-incubated for 30 min with 25 mg of tGAGs prior to loading onto the streptavidin column, or was loaded first, with the tGAGs being run through the column bed thereafter.

Figure 5:
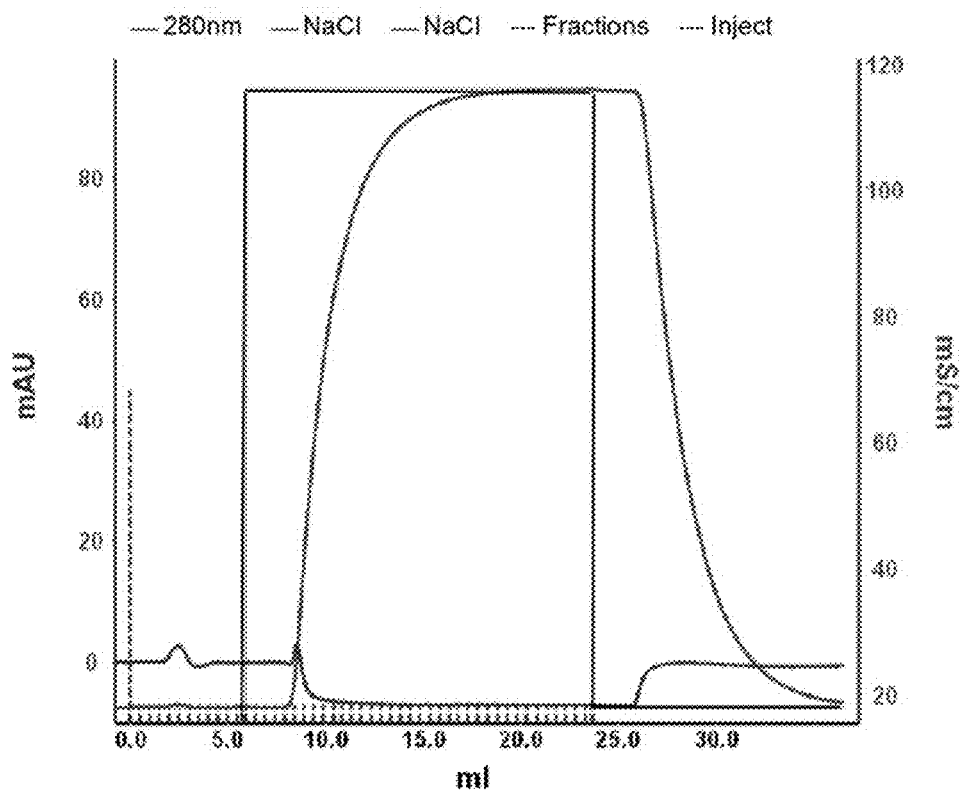
FIG. 5. BMP2-HBP (1 mg) loaded onto a Hi-Trap column. The 280 nm absorbance levels indicate that the peptide remains attached to the column even under high salt conditions; thus there was successful coupling of the biotinylated peptide to the streptavidin linker.

Pre-incubation of tGAGs with the BMP2-HBP revealed the complete inability of the peptide to associate with the column (FIG. 4), let alone mediate any isolation of specific GAGs. When the peptide was loaded onto the column alone, however, its association with the column was absolute, with effectively no elution of peptide, even under 1 M salt conditions (FIG. 5). This high affinity association indicates that the biotin-streptavidin association is functioning correctly, and suggests a possible inhibition of binding to the column, when loaded together with tGAGs, due to steric hindrance.

Column Loading Capacities

Figure 6:
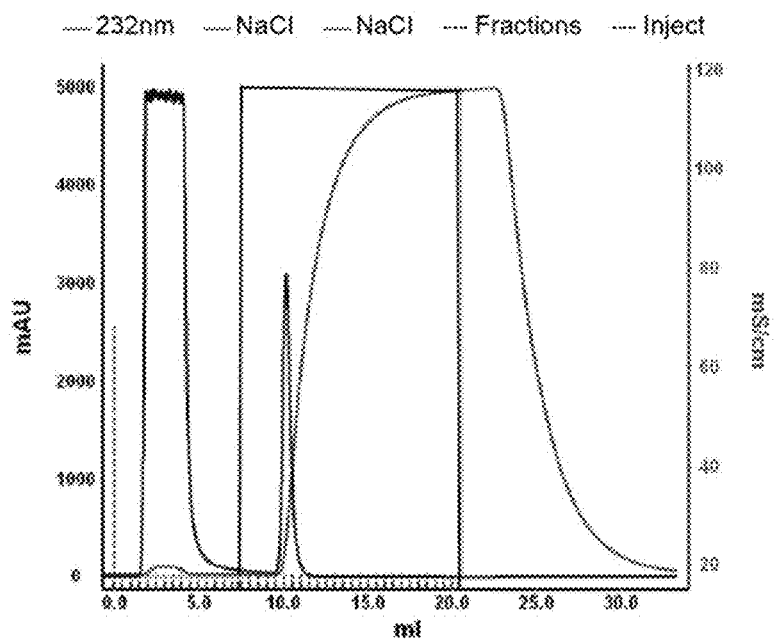
FIG. 6. BMP2-HBP (1 mg) coupled column loaded with of 25 mg of tGAGs. The chromatogram (232 nm) clearly shows both an overloading of the column, in the flow through as well as the binding of some GAGs to the BMP2-HBP bed.
Figure 7:
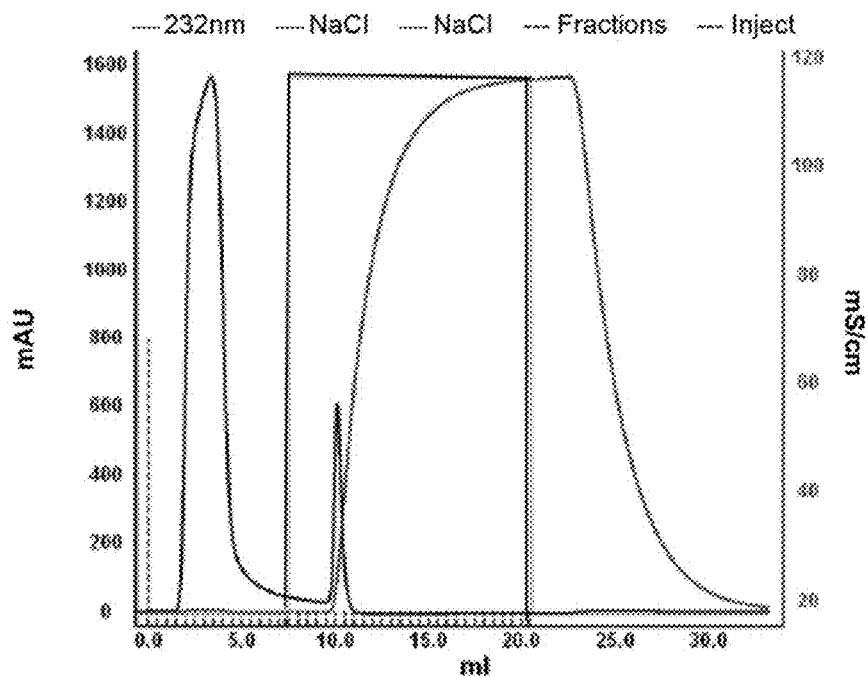
FIG. 7. Re-application of the GAG− (flowthrough) fractions from the previous experiment (FIG. 6). The presence of a significant GAG+ elution peak indicates that all available BMP2-HBP binding sites had been saturated, resulting in a large proportion of susceptible GAGs exiting the column in the flowthrough.

As the proportion of tGAGs that were likely to have a relative affinity for the BMP2-HBP was unknown, we first sought to standardise the quantities of tGAGs loaded onto the peptide column at each run for separation. Hi-Trap columns were prepared by immobilising 1 mg of the BMP2-HBP for the extraction of tGAGs with a specific affinity for the BMP2 heparin-binding site. This amount was selected so as to maximise the quantity of available peptide for future experiments should column stability become compromised over time. Instability is a significant problem with peptide columns, with corresponding impacts on consistency. Initial attempts at loading of 25 mg of tGAGs onto a 1 mg BMP2-HBP coupled column resulted in a clear overloading, as observed via absorbance at 232 nm in the flowthrough (FIG. 6). Although a significant elution peak was observed, tGAGs with affinity for the HBP were lost in the flowthrough due to overloading. This was examined by re-running the flowthrough through the peptide column (FIG. 7). This resulted in a significant GAG+(elution) peak, indicating that the previous run had saturated the column.

Figure 8:
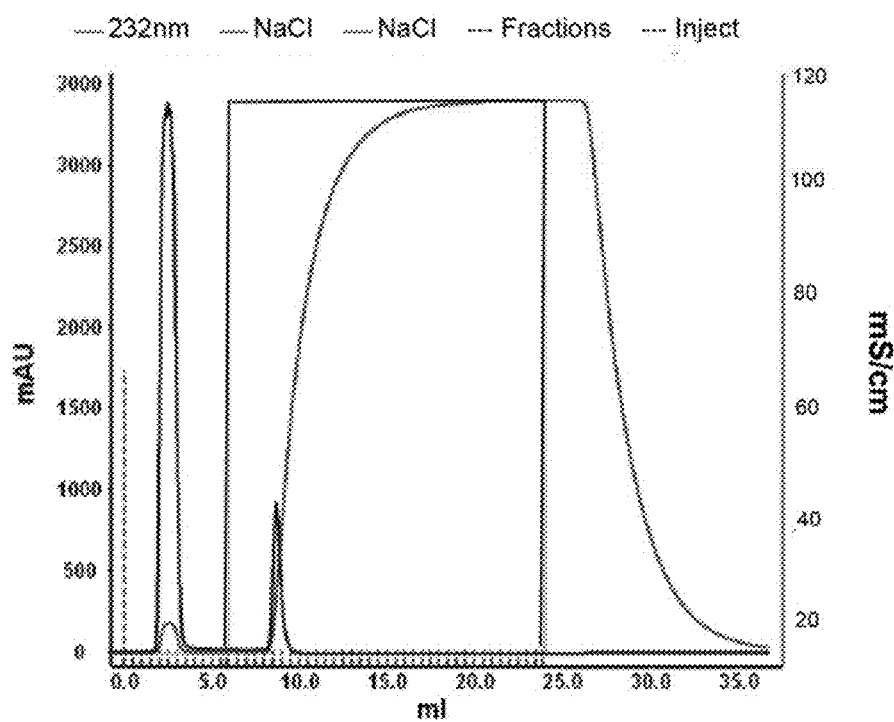
FIG. 8. BMP2-HBP (2 mg) coupled column loaded with tGAGs (6 mg). The chromatogram (232 nm) clearly shows no overloading of the column, and the presence of a GAG subpopulation with a relative affinity for the BMP2-HBP.
Figure 9:
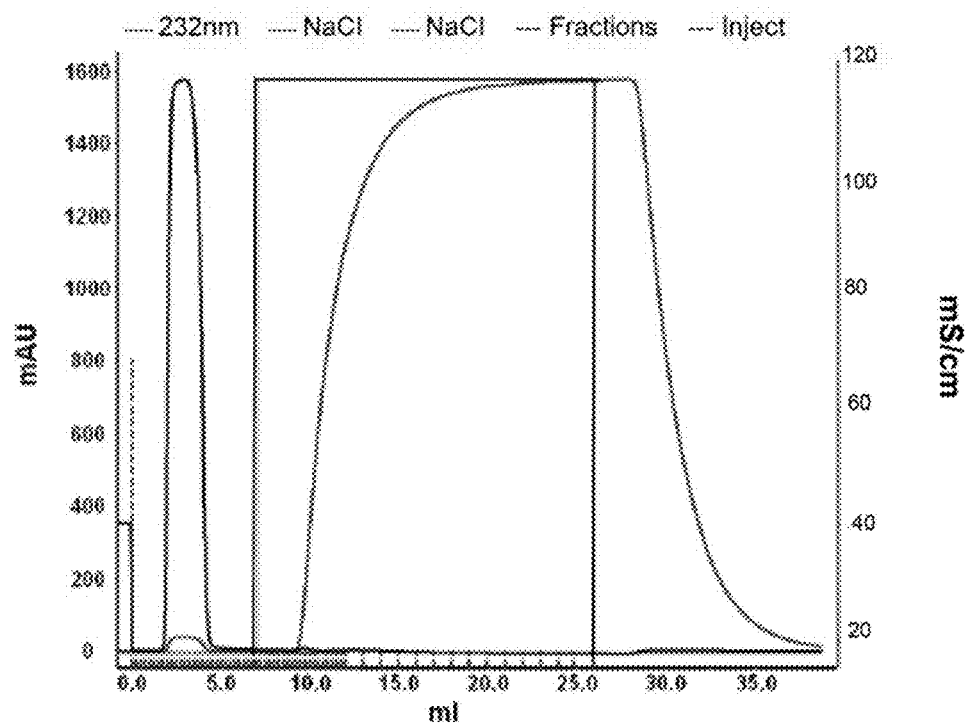
FIG. 9. Re-run of GAG− (flowthrough) from previous run (FIG. 8). The absence of a GAG+ elution peak indicates that the available BMP2-HBP binding sites were not saturated in the previous run, allowing the efficient extraction of GAG+ sugars in a single run.

Further optimisation led us to routinely load no more than 6 mg of tGAGs onto a 2 mg BMP2-HBP column. This, as evidenced by the flowthrough peak (FIG. 8) and the absence of a positive-binding fraction (FIG. 9), forestalled column overloading. The extraction of those tGAGs with an affinity for the BMP-HBP from each sample set in a single pass allowed us, in turn, to separate GAG+ and GAG− fractions more efficiently.

GAG Domain Analysis

GAG+ Chain Specificity

With the establishment of a standardised protocol, we were able to reproducibly isolate GAG+ fractions for further analysis.

Given the domain structure of heparan sulfate that mediates the binding specificity for proteins, it is likely that multi-domain GAG chains that bind to the column are in fact composed of a large proportion of chain with little or no specific affinity for BMP2. Similarly, it is possible that chains that appeared GAG− may in fact contain domains that carry some affinity for the BMP2-HBP. In order to examine these possibilities, it was necessary to break down the GAG chains into their component domains for more extensive examination.

The enzyme heparinase III (heparitinase I) cleaves HS chains primarily in those areas flanking highly sulfated regions, thereby liberating the highly charged, protein-associating domains that bind susceptible growth factors, in this case the BMP2-HBP. Both GAG+ and GAG− fractions were exposed to heparinise digestion, although neither fraction showed any change in their affinity for the BMP2-HBP (FIG. 10).

Heparinase III digestion of both full length GAG+ and GAG− fractions was subsequently conducted, and both digested sample sets subsequently loaded onto the BMP2-HBP column to assess retention affinity.

Figure 10:
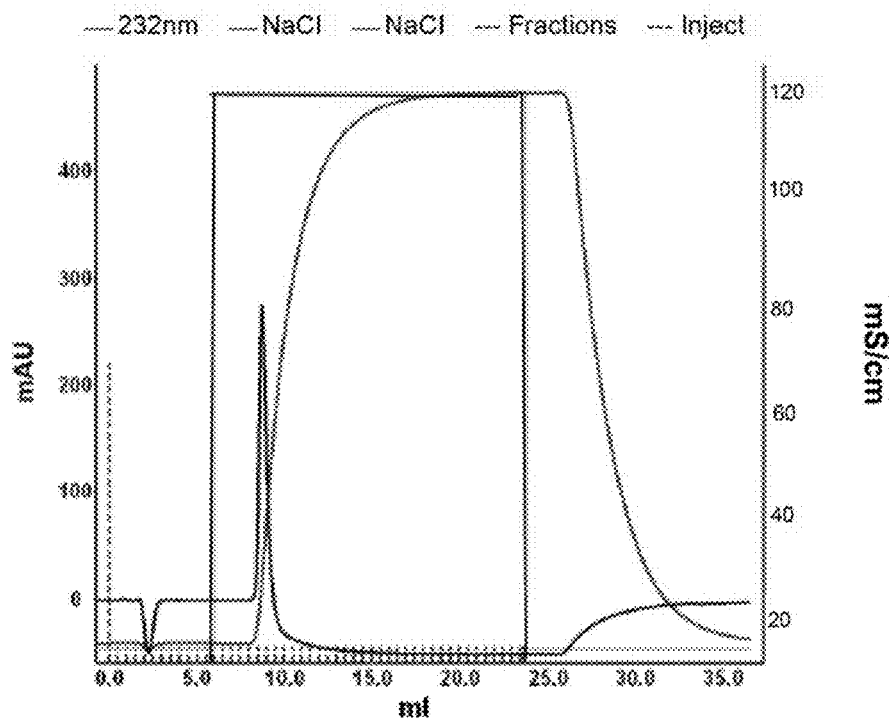
FIG. 10. Re-application of isolated full length GAG+ fractions (2 mg) shows no change in affinity for the BMP2-HBP (2 mg) column prior to heparinase III digestion. A reapplication of GAG− fractions against the BMP2-HBP column also showed no change in affinity, with all GAGs exiting the column in the flowthrough essentially as in FIG. 9.
Figure 12:
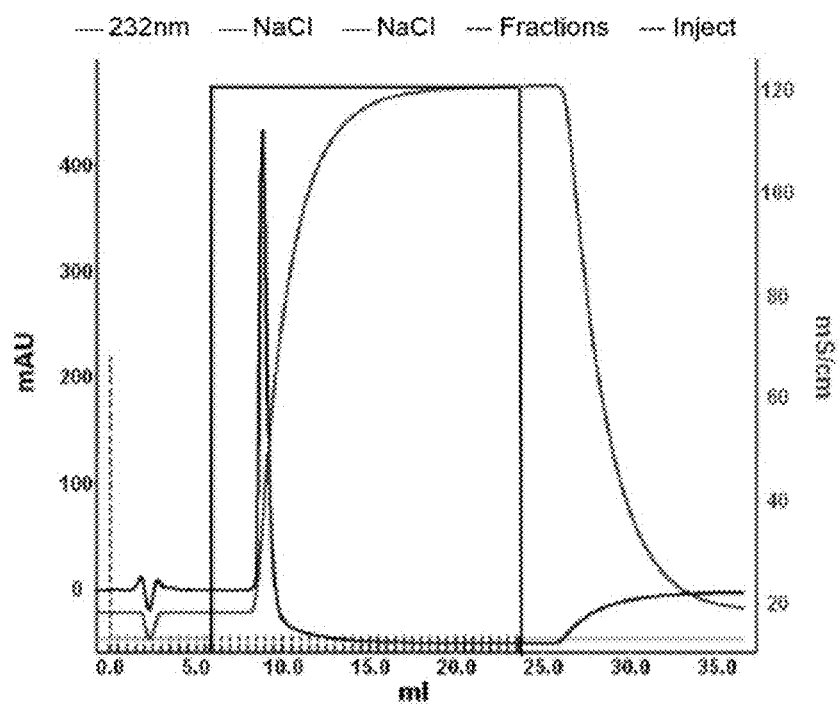
FIG. 12. GAG+ fractions (2 mg) digested with heparinase 3 before loading onto the BMP2-HBP (2 mg) column. The chromatogram (232 nm) demonstrates that the GAG+ samples are retained by the column, suggesting that all domains on the full length GAG+ chain have a relative affinity for the BMP2-HBP. The increase in the absorbance peak, as compared to the same dry weight quantity of GAG+(FIG. 10), indicates the efficacy of the heparinase 3 treatment.
Figure 13:
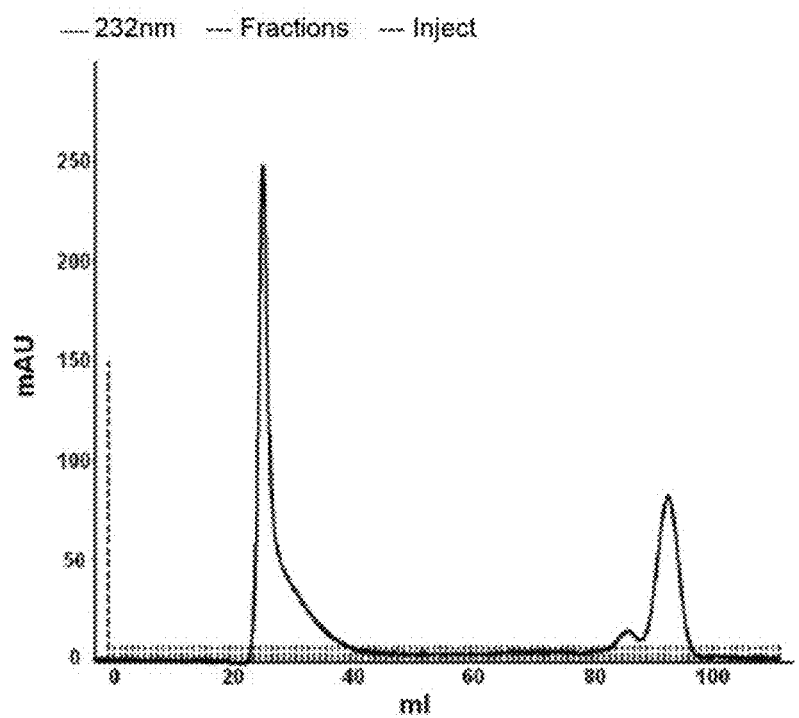
FIG. 13. Full length GAG+ chains separated using a Biogel P10 column with an exclusion limit of between 1.5 kDa and 20 kDa. The chromatogram shows that a large proportion of the sample chains have an overall molecular weight of more than 20 kDa.

The efficacy of the heparinase digestion was validated by the increase in relative absorbance of samples of equal dry weight after enzymatic digestion, as shown in FIGS. 10 and 12. As the monitoring of GAG chains at 232 nm is via the sugar chain itself and, in particular, unsaturated bonds, any cleavage along the chain's length by heparinase III, resulting in unsaturated bonds of HS fragments, leads to an increase in absorbance.

Figure 11:
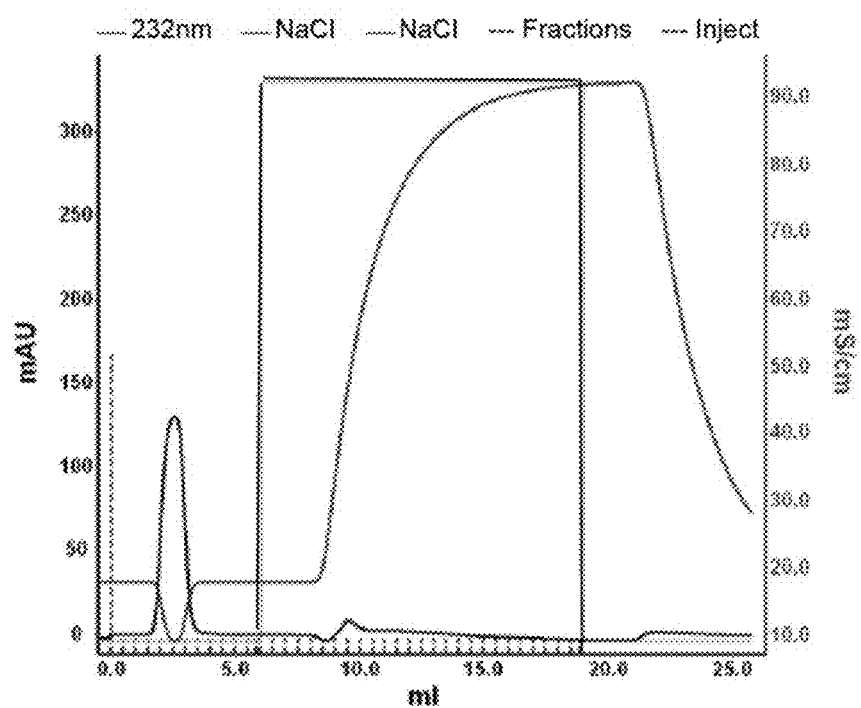
FIG. 11. GAG− fractions (1 mg) digested with heparinase III before loading onto the BMP2-HBP (2 mg) column. The chromatogram (232 nm) clearly shows that no GAG samples remain bound to the column, but exit in the flowthrough. This indicates the absence of any GAG+ domains in the full length GAG− chains.

Interestingly, heparinase digestion of full length GAG− chains yielded no fractions carrying any notable affinity for the BMP2-HBP (FIG. 11). However, the digestion of full-length GAG+ samples similarly resulted in no fractions that lacked affinity for the BMP2-HBP (FIG. 12). This result suggests that entire chains of BMP-binding GAG are produced containing domain repeats that have a specific affinity for the HBP. Alternatively, the HBP may not be able to yield sufficient discrimination between GAG+ domains with varying affinity under these minimalist conditions.

GAG+ Composition

Full Length GAG+ Sizing

In order to examine the composition of GAG+ fractions from the BMP2-HBP column, we first examined their average size. This was to ensure that we were actually separating GAG chains of reasonable length, rather than small fragments not carrying any specific affinity. Although any sizing of GAG chains is problematical, owing to their relatively rigid rod-like conformation, a set of assumptions invoking Stoke's radius and apparent sphericity can be made.

Full length GAG+ samples were loaded onto Biogel P10 gel filtration columns (1 cm×120 cm) with an exclusion limit of between 20 kDa to 1.5 kDa. Absorbance measured at 232 nm indicated a large proportion of GAG+ molecules had an overall apparent size greater than 20 kDa (FIG. 13).

It has been posited that sugar chains must be longer than approximately 10-14 rings in order to potentiate significant biological activity for the FGF family of mitogens. In terms of apparent molecular weight, a chain of 14 fully sulphated disaccharides corresponds to approximately 8.7 kDa. As the majority of chains found in the GAG+ samples show an apparent molecular weight >20 kDa, it is reasonable to assume that the interaction that they carry for the BMP2-HBP has some specific affinity and is not the result of a general non-specific interaction.

GAG+ Sugar Species

There are five major glycosaminoglycan sugar families: hyaluronan, keratin sulfate, dermatan sulfate, chondroitin sulfate and heparan sulfate. Of these five, only heparan sulfate, chondroitin sulfate and dermatan sulfate have the capacity to generate variably sulfated domains that may code for specific interactions with particular cytokines such as BMP2. The identification of the type of sugar species isolated using the BMP2-HBP column was of crucial importance for this study, and was determined using a combination of diagnostic chemical and enzymatic degradations. In particular, heparan sulfate, one of the major GAG candidates for the interaction with BMP2, can be completely degraded into its disaccharide components in the presence of nitrous acid.

Figure 14:
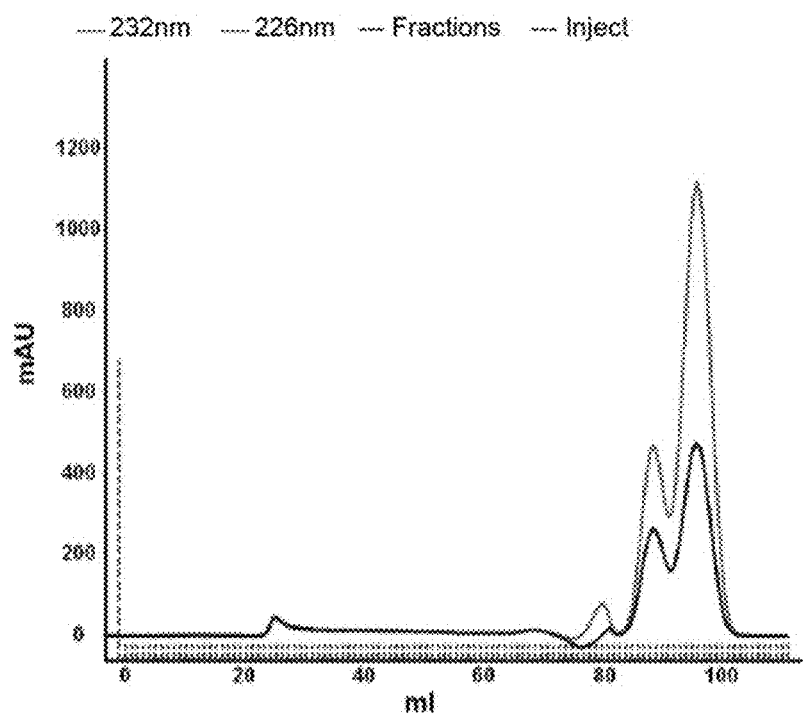
FIG. 14. Full length GAG+ sugar chains treated with nitrous acid for 20 min to diagnostically degrade heparan sulfate species. The chromatogram, generated from a Biogel P10 sizing column, shows an almost complete degradation of all GAG+ chains as compared to FIG. 13, indicating that GAG+ isolated chains consist primarily of heparan sulfate.

Thus, our HBP-retained GAG samples were incubated with nitrous acid for 20 min prior to separation on a Biogel P10 sizing column. Examination of the resulting chromatogram revealed an almost complete degradation of all GAG+ sugar samples, as measured by absorbance at 232 nm and 226 nm (FIG. 14).

This result strongly suggests that the full length sugar chains isolated specifically against the BMP2-HBP consist primarily of heparan sulfate, as other sugar chains are not affected by nitrous acid depolymerisation.

Although almost all the GAG+ chains could be degraded in such a manner, a small peak was nevertheless observed at higher molecular weights (>20 kDa). It can be postulated to consist of chondroitin sulfates, of which CS-B (dermatan sulfate) and CS-E (chondroitin-4,6-sulfate) demonstrate sulfation complexity akin to heparan sulfates.

GAG Species Analysis

BMP2-HBP Specific GAGs (Alternative Species)

The degradation of full length GAG+ chains by exposure to nitrous acid clearly indicated that the majority of GAG+ sugar chains consisted of the heparan sulfate sugar species (FIG. 14). The degradation of the GAG+ sample was not, however, complete as was observed by the remnant peak in the high molecular weight region. The presence of this peak points strongly to the possibility of other species of sugar chains, such as chrondroitin or dermatan sulfate. We next sought to examine the possible affinity the other two sugar types may have for this cytokine by first examining a variety of commercially available chondroitin and dermatan sugars for their affinity to the BMP2-HBP column.

We tested chondroitin-4-sulfate (C4S), chondroitin-6-sulfate (C6S) and dermatan sulfate (DS) by, in each instance, loading 6 mg of the sugar onto the BMP2-HBP column under the same conditions used to isolate GAG+ chains from MC3T3 matrix samples.

Figure 15:
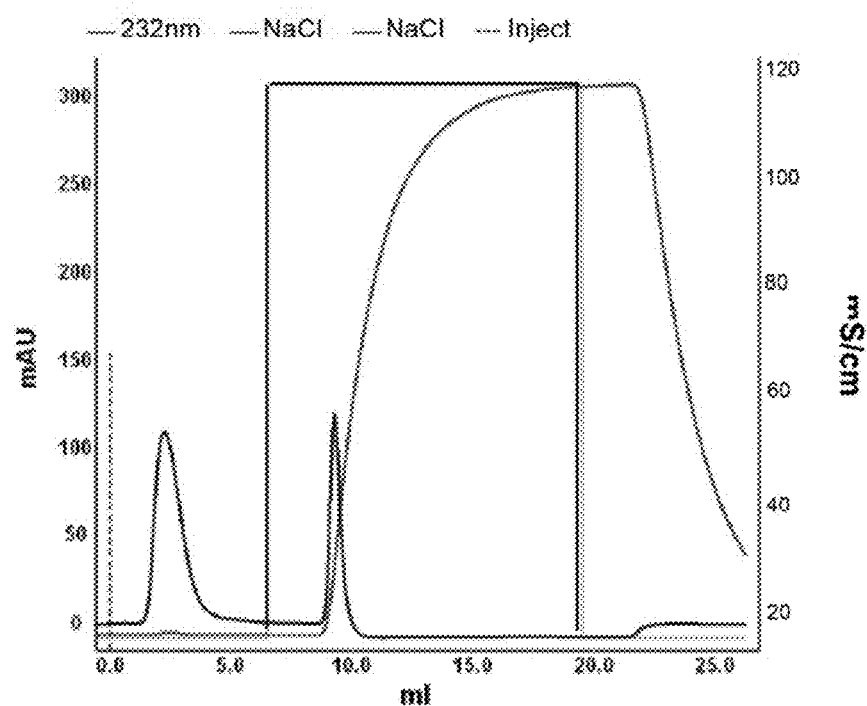
FIG. 15. Chondroitin-4-sulfate (6 mg) loaded onto BMP2-HBP (2 mg) column. The chromatogram clearly illustrates a significant proportion of the GAG chains having an affinity for the peptide, as they eluted at a similar salt concentration as the GAG+ samples.
Figure 16:
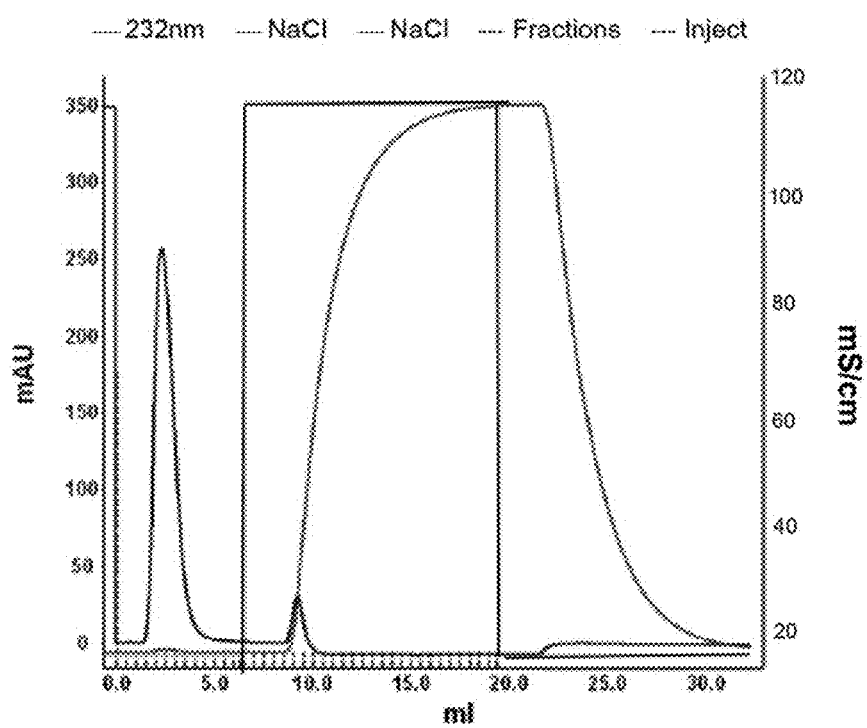
FIG. 16. Chondroitin-6-sulfate (6 mg) loaded onto BMP2-HBP (2 mg) column. The chromatogram indicates that few of the C6S GAG chains have any affinity for the peptide column.
Figure 17:
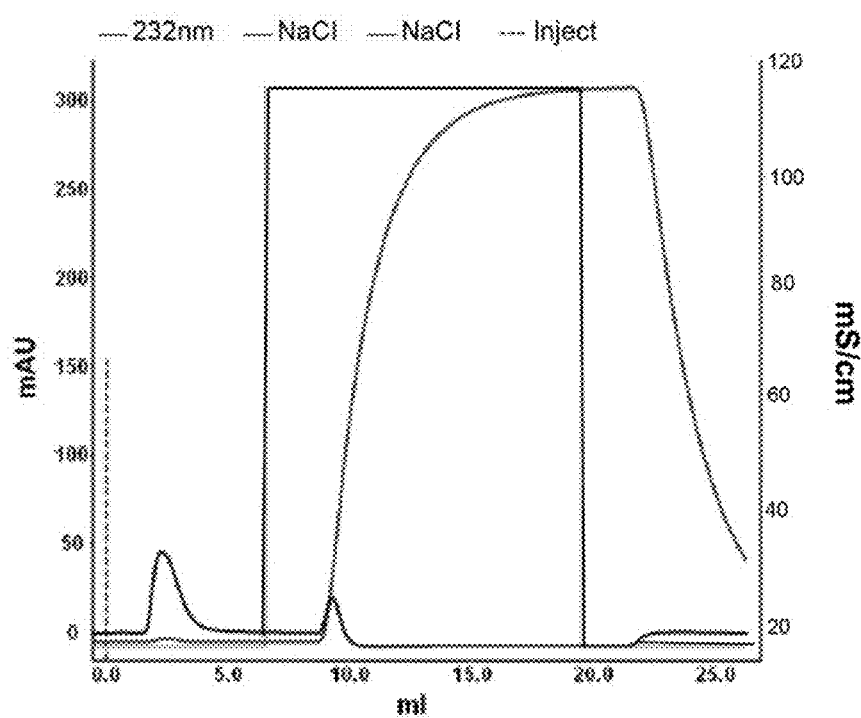
FIG. 17. Dermatan sulfate (6 mg) loaded onto the BMP2-HBP (2 mg) affinity column. The chromatogram indicates that few of the DS GAG chains had any affinity for the peptide, with only a small proportion of the GAGs being eluted at a similar salt concentration to GAG+ samples.

The chromatograms illustrating the affinity of each of the 3 sugar chain types showed that only C4S (FIG. 15) had any significant affinity for the peptide. This affinity taken together with the lack of affinity for the BMP2-HBP column observed for both C6S (FIG. 16) and DS (FIG. 17) samples, appears to indicate that C4S has a particular, potentially significant, interaction with the BMP2 heparin-binding site.

As any potential interaction between chondroitin sulfate and BMP2 has not yet been well characterised, these results led us to question the validity of column chromatography as an accurate monitor of the BMP2/heparan interaction. In order to further explore the specificity of the interaction dynamic, we tested several commercially available sugar species for their affinity to the column. These included heparan sulfate, low molecular weight heparin (Heparin-LMW), high molecular weight heparin (Heparin-HMW) and Heparin-HMW treated with heparinase I.

Figure 18:
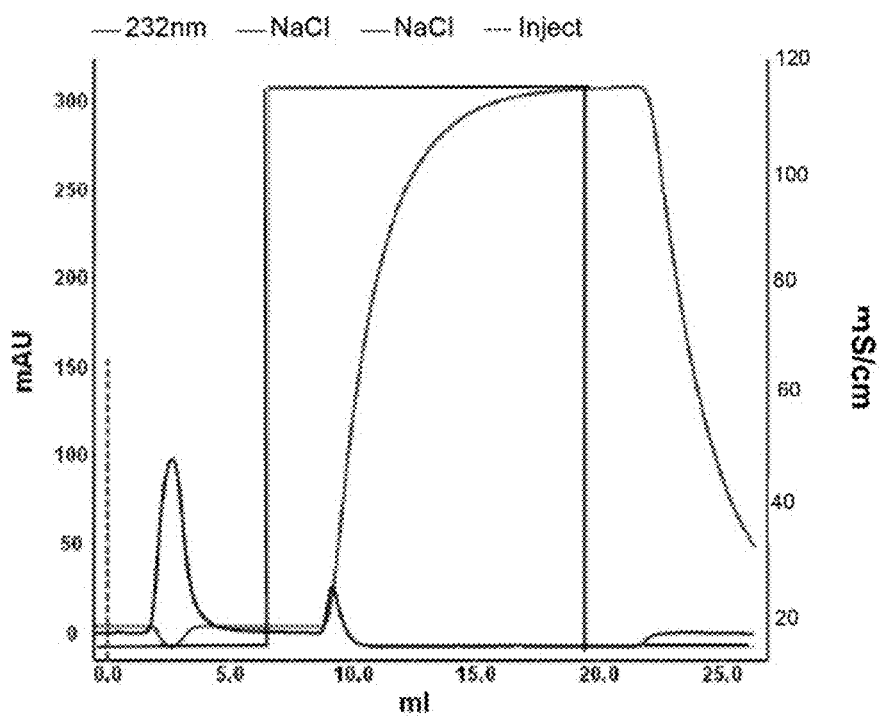
FIG. 18. Bovine heparan sulfate (2.5 mg) loaded onto the BMP2-HBP (2 mg) column. The chromatogram (232 nm) reveals only a small fraction of the GAGs binding to the column.

Interestingly, none of these commercially available GAG species appeared to demonstrate any specific interaction with the peptide column. Heparan sulfate from bovine kidney had very little affinity (FIG. 18), a behaviour that was further confirmed by its inability to positively augment FGF2-mediated cell proliferation (data not shown), as is observed in the presence of HS2. This reduced ability of this GAG sample to bind the column may be as a result of it being sold in a relatively unsulfated form.

Figure 19:
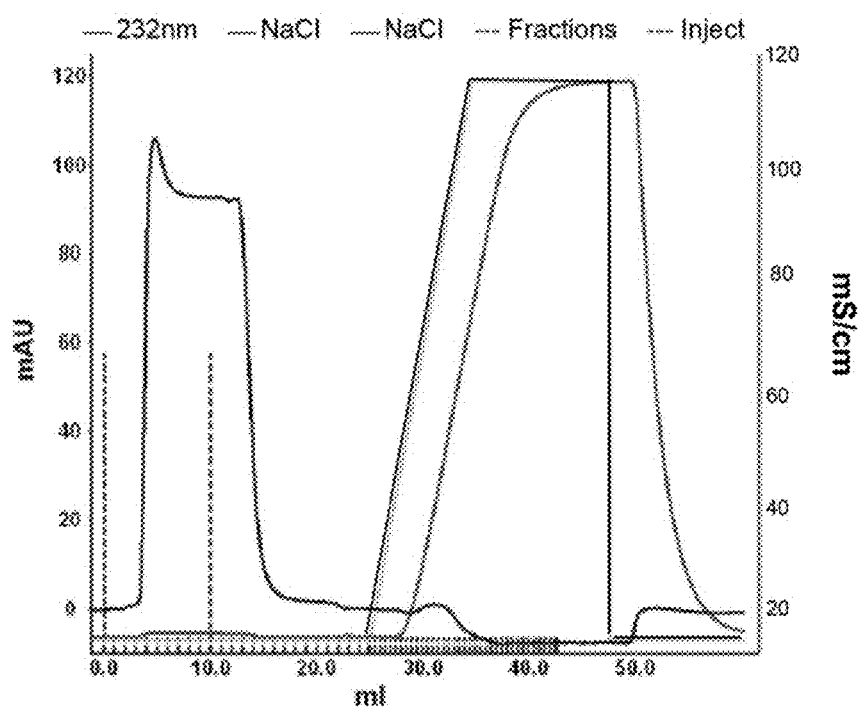
FIG. 19. Heparin-LMW (50 mg) loaded onto the BMP2-HBP (2 mg) column. The chromatogram (232 nm) reveals that almost no GAG bound to the peptide.
Figure 20:
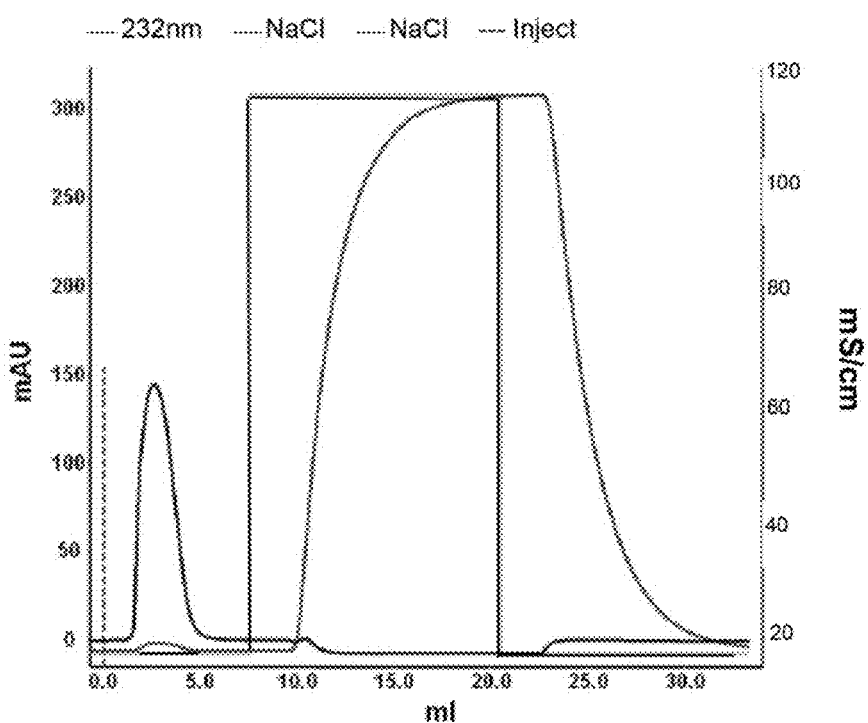
FIG. 20. Heparin-HMW (28 mg) loaded onto the BMP2-HBP (2 mg) column. The chromatogram (232 nm) reveals that almost no GAG bound to the peptide.

None of the tested heparin samples showed even a minor affinity for the column. This is of particular interest as BMP2 itself was historically first isolated using heparin columns. In order to confirm this result, both LMW (FIG. 19) and HMW (FIG. 20) heparin were tested; neither showed any appreciable affinity for the column.

Figure 21:
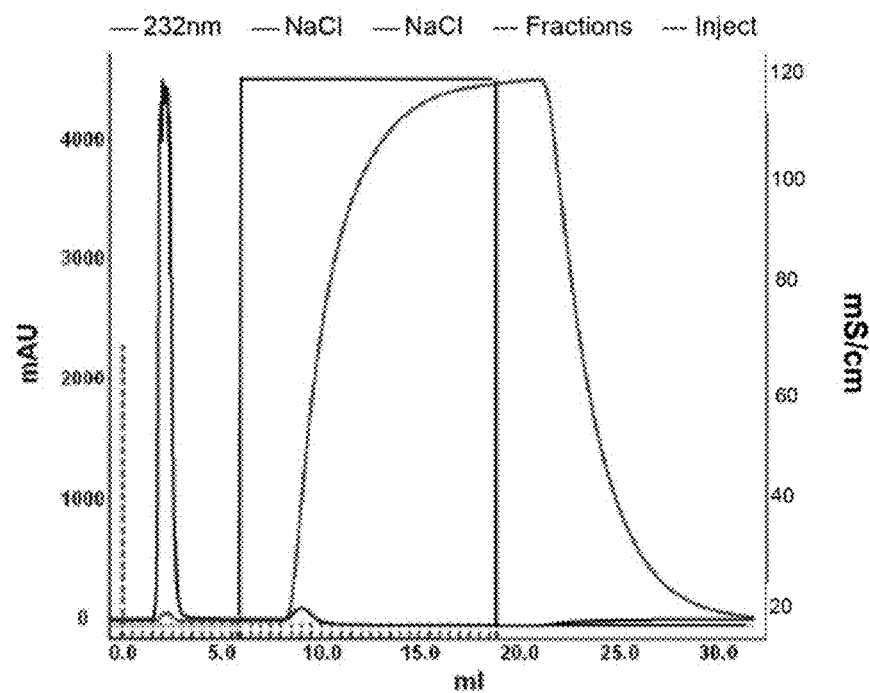
FIG. 21. Heparin-HMW (25 mg) predigested with heparinase I was loaded onto the BMP2-HBP (2 mg) column.

As we surmised that the relatively small BMP2-HBP peptide may have had difficulty maintaining its association with the much larger heparin molecules, we next predigested the heparin-HMW samples using heparinase I. These smaller heparin-HMW fragments were then run over the BMP2-HBP column; this treatment did not, however, appear to improve the ability of any of the heparin samples to bind the peptide column (FIG. 21).

This inability of the peptide column to show any specific interaction with any of the various preparations of heparin was somewhat unexpected, due to BMP2 conventionally being isolated via heparin affinity. It is possible, however, that this may be as a result of the reversing of the "receptor-ligand" order of interaction; in this case the BMP2-HBP represented the fixed "receptor" as opposed to the heparin that represented the "ligand", or that the concentrations of BMP2-HBP or soluble heparin favour a dissociated state that rapidly negates any affinity under flow/salt stress.

Conclusions

The use of a preosteoblast-derived ECM substrate provided us with a useful model for simulating the activity of natively secreted, ECM-associated GAGs in relation to such osteoinduction. Though numerous previous studies have examined the role that this native interaction has in modulating the activity of BMP2, this has usually been conducted at the level of the cytokine, rather than with a view to exploring the sequence specificity of the biomodulating GAGs.

Hence here we sought to exploit the availability of natively secreted GAGs in the MX substrate and their potential for direct, sequence-specific interaction and modulation of BMP2-induced C2C12 myoblast commitment to the osteogenic lineage.

Anion Exchange

The use of this particular standard and well characterised protocol provided us with conclusive evidence for GAG accessibility from the $NH_4OH$-treated MX substrate. Our initial concerns were centred around the harsh chemical treatment used to lyse the cellular components of the ECM, and that this may have also resulted in the stripping of the majority of GAGs from the ECM. However, the significant, high affinity peak observed in the anion exchange chromatogram clearly illustrates the retention of a large quantity of GAGs within the MX substrate. While this particular methodology does not allow for the identification of individual GAG species, it does offer conclusive evidence of their presence in the sample due to their being amongst the most negatively-charged molecules secreted by cells.

BMP2-HBP Column System

Previous research into the functional role of the BMP2 heparin-binding peptide provided us with a useful tool to investigate the potentially specific interaction that BMP2 has with GAGs. This single string of amino acids, located at the N-terminus of each BMP2 monomer, appears to be solely responsible for mediating BMP2's affinity for GAGs.

We thus investigated the use of this region of the BMP2 molecule as a ligand "bait" in attempts to retain those GAG chains that carried relative affinity for the cytokine. The use of the BMP2-HBP in this manner resulted in a significant retention of HS to the peptide column (GAG+).

Column Preparation

Using an N-terminal biotinylated HBP we prepared a BMP2-HBP affinity chromatography column, and were able to successfully retain GAG samples that were candidates for controlling the native BMP2 homodimer. Initial preparations of the column highlighted some interesting problems. Preparations of biotinylated BMP2-HBP that were premixed with tGAGs showed an inability to bind to the column. As later tests showed that the BMP2-HBP easily attached to the streptavidin column when loaded on its own this result indicated that the GAGs interfered with the ability of the peptide's biotinylation site to associate with the streptavidin column. The tGAGs themselves carried no affinity for the streptavidin, indicating that the direct interaction with the BMP2-HBP, possibly via steric hindrance, was responsible for this.

Column Optimisation

Without any direct information that would allow us to estimate the binding capacities of GAG+ sugars in our samples, our peptide column needed to be optimised to ensure that excessive sample loading would not lead to column saturation and consequent sample loss. This initially involved intentionally saturating the column in order to examine the binding capacity of a known quantity of BMP2-HBP. Even with a large quantity of tGAGs the peptide was capable of retaining the majority of GAG+ sugar chains. Under these conditions as little as 1 mg of BMP2-HBP was able to completely retain all GAG+ chains within two cycles. The column thus appeared to "simulate" a true BMP2 growth factor column and provide an extremely efficient way of extracting GAG+ samples.

The optimisation of peptide-based columns for specific GAG isolation is a complex procedure that varies greatly depending on the size and individual chemical characteristics of the protein used. Previous studies, utilising FGF-1 and 2 growth factor columns (Turnbull and Nurcombe, personal communication), also showed a significant need for continual column maintenance and short viable column life-spans. These studies demonstrate the laborious nature of working with peptide columns and the care that must be taken to correctly optimise this manner of system. Unfortunately, while other systems for the analysis of specific protein-GAG interactions exist, these generally lack the capacity to isolate sufficient quantities of GAGs for further analysis, making them inappropriate for our intended course of study.

GAG Domain Analysis

GAG sulfation patterns are, particularly in the case of heparan sulfate (HS), frequently concentrated into domains of high sulfation that are interspaced with regions of little sulfation. This grouping of sulfation sites into domains is what provides region-specific binding of ligands to the GAG chain, allowing a single sugar molecule to potentially bind a variety of different targets, and to stabilise the interaction between these, as is seen in the FGF system. Exceptions to this proposed model for HS-ligand interactions include the interaction between interferon gamma (IFNγ) and heparan sulfate. In this instance the interaction between the GAG and IFNγ leads to an increased potency of the cytokine. IFNγ that remains dissociated from local GAGs is rapidly processed into an inactive form, thereby preventing its signalling in inappropriate areas after diffusion. IFNγ also displays four separate heparin-binding domains, each with a different sequence, a finding not unusual for heparin-binding proteins. However, only two domains found immediately at the C-terminus of the protein have been shown to mediate INFγ's heparin-binding characteristics. Importantly, sequence analysis of the HS sequence with specific affinity for these two IFNγ heparin-binding sites revealed an interesting difference in comparison to the commonly observed model of HS-ligand interaction. In this case, the sequence of HS responsible for the binding of IFNγ was found to be composed of a predominantly N-acetylated region, carrying little sulfation. This region was flanked by two small N-sulfated regions. This differs significantly with the system observed in FGF, where sulfation patterns in NS domains are responsible for mediating the interaction between FGF and HS. In recent years, this type of interaction has been observed in numerous other systems, such as PDGF, IL-8 and endostatin. The discovery of this kind of interaction with HS, as observed in these cytokines, may be able to explain the bioactivity observed in hyaluronan, which carries no sulfation patterns at any point along its chain and yet has the ability to modulate the activity of such factors as NF-KB.

These observed interactions between ligands and GAGs, in particular that of IFNγ, differ significantly to the proposed, and our observed, mode of interaction between HS and BMP2. BMP2's single, N-terminal heparin-binding domain exhibits no secondary structure and appears to interact with HS solely on the basis of charge. While in-depth sequence analysis of HS that binds this peptide sequence was not conducted, its requirement to be eluted under approximately 300 mM NaCl conditions lead us to suspect the presence of a moderate degree of sulfation, thereby placing this interaction within the conventional model of sulfation patterns mediating specific interactions.

GAG+ Chain Specificity

The allocation of sulfation patterns into domains that give HS its ability to stabilise proteomic interactions also results in the possibility that a GAG+ sugar chain of sufficient length and complexity may carry several domains that have no direct affinity for the BMP2-HBP on their own, due to their carrying a different sulfation sequence. Conversely, it is also possible that some full-length sugar chains that were identified as having little affinity for the BMP2-HBP (GAG−) may contain some cryptic domains that do carry such affinity.

In recent years, numerous reports have been published that provide strong evidence for a "sulfation code" within these complex carbohydrate chains. While the details of this "sulfation code" remain difficult to elucidate, and the sequencing of long chains of sulfated carbohydrates is a complex and time consuming process, a number of possible modes of specific interaction between GAGs and ligands have been proposed. One observation in particular has led to the characterisation of numerous GAG-ligand models; the grouping of sulfation into discrete regions, or "domains", along the length of many types of GAGs, such as heparan sulfate. Interestingly no template for this phenomenon has yet been observed, and it appears to be primarily a result of the temporal activity of the sulfotransferase enzymes responsible for this phase of GAG synthesis.

Particularly useful tools in the study of specific GAG sequences are a number of heparin lyases that can be used to examine targeted depolymerisation of complex carbohydrate chains, thereby providing insight into their structure. One particular heparan lyase, heparinase III (heparitinase), cleaves heparin sulfate chains at sites flanking the highly sulfated domains that may occur in heparan sulfate chains. Thus, using this enzyme, it is possible to liberate these potentially active regions from the full length sugar chains and separate them, if they function as single domains, via affinity chromatography, from regions with no specific affinity for the BMP2-HBP.

It is important to note that, in the case of GAG-ligand interactions, affinity by sequence does not necessarily guarantee bioactivity. The mode of activity mediated by GAGs during their association with their various ligands differs greatly depending on the system. In some instances where the sugar chain is responsible for prolonging protein-protein interaction via stabilisation of tertiary protein structures, such as is found between FGF and its receptor, and the interaction between HGF/SF and Met, multiple discrete sulfation regions may be involved in mediating the intended bioactivity of the sugar chain. In such instances the isolation of individual sulfated domains from a full length carbohydrate chain may, in fact, result in an inhibition of sugar bioactivity since though each "domain-fragment" still binds its intended target it is unable to mediate the intended biological effect of a combined full length carbohydrate chain. Interestingly, this particular characteristic of GAG-ligand interactions is precisely what makes this manner of approach useful for modulating BMP2 activity. The proposed model for GAG modulation of BMP2 bioactivity involves immobilization of the cytokine to GAGs in the ECM or on the cell surfaces. In this type of system the application of exogenous GAGs specific to the heparin-binding domain of BMP2 would prevent this interaction, increasing short term BMP2 mediated signalling, similar to the effect observed during the addition of soluble heparin. While there is some indication that this manner of interaction would continue to protect the cytokine from proteolytic degradation, delocalization of BMP2 from its intended region of bioactivity has the potential to negatively impact the cytokines effectiveness in the long term.

Control testing of our full length GAG+ and GAG− chains resulted in similar profiles to those observed during their primary separation. Analysis of GAG+ and GAG− chains post treatment with heparinase III, however, gave surprising results. The digestion of GAG+ chains did not seem to generate separable fragments based on simple affinity for the BMP2-HBP. Furthermore, the digestion of full length GAG− chains yielded no liberation of positive domains from the negative sugar chains. There is some possibility that the enzymatic digestion did not go to completion. However, the resulting chromatogram clearly showed a large increase in the absorbance at 232 nm when compared to the full length GAG chains. As a large proportion of the absorbance of glycosaminoglycans at 232 nm is mediated via absorbance of unsaturated bonds, such as those formed during enzymatic depolymerisation, it strongly indicates that the enzymatic digestion was, in fact, successful.

The implications of this result are somewhat unusual. This data suggests that GAG chains are not only synthesised by cells to specifically interact with BMP2, but that, in the case of MC3T3 cells, these sugar chains carry a number of sequence repeats specific for aspects of BMP2 metabolism. The fact that BMP2 is an extremely potent factor may offer an explanation for this observation. The effects of BMP2 on the osteoinduction of mesenchymal progenitor cells is well documented, as is its ability to induce ectopic bone formation in cells that are even more removed from the osteogenic lineage. Given this potency, aberrant signalling of BMP2 is known to have deleterious consequences both for healing and in development. It is possible that numerous repeats of the BMP2-HBP interaction sequence on preosteoblast GAGs are designed to ensure a maximal binding, and thereby the modulation, of this cytokine's ability to induce altered cell fate. Conversely, the extremely low concentrations of BMP2 produced in vivo may also require this type of sugar chain production in order to ensure the retention of a sufficient local concentration, an observation supported by the extremely high concentrations of BMP2 required in vitro to induce the osteogenic differentiation of C2C12 myoblast cells.

Of particular interest is the fact that this repetition of BMP2-binding domains is produced via a synthesis pathway for which no template or timing mechanism has yet been elucidated. The accuracy and reproducibility of sequence specific domains within a single sugar chain (as opposed to the random clustering of such domains with those against other ligands) strongly suggests that these cells do, in fact, have the ability to direct the generation of specific sugar sequences. The current understanding of HS structure implicates the progressive post-synthesis "editing" of the carbohydrate chain in the generation of sequence-specific regions, with observations pointing towards some manner of enzymatic "template", whereby the local concentrations of particular sulfotransferases as well as other interacting molecules are used to directly control the generation of specific sugar sequences. Our current understanding of this mode of specific synthesis is largely formulated based on numerous studies including those by Lindahl et al. that investigated the high affinity interaction between antithrombin III and heparin, and those by Esko et al. involving Chinese hamster ovary (CHO) cell mutants with altered GAG synthesis pathways. These studies, while varying significantly in their approaches to GAG analysis, all point towards a highly conserved system of specific GAG synthesis, for the directed modulation of cytokine and receptor activity. Importantly, these studies also serve to explain the potential generation of such BMP2 repeats as were observed in our study.

GAG+ Constitution

Full Length GAG+ Size

The bioactivity of individual GAGs chains for FGFs is closely related to carbohydrate chain length. A common approach to assessing GAG bioactivity is to assay ever shorter sulfated domain fragments and so determine the shortest possible sequence required to mediate the activity observed.

Using this approach we first examined full length GAG+ sugar chains, and determined that they were >20 KDa in size, long enough to carry multiple domains with affinity for BMP2. Interestingly, this observation provided support for the earlier observation that GAG+ samples treated with heparinase 3 showed multiple repeats of carbohydrate chain segments with a specific affinity for BMP2, since a variably sulfated sugar chain of this size has the capacity to carry numerous sulfated domains.

GAG+ Sugar Species

With the majority of the five glycosaminoglycan types that constitute the "glycome" able to encode the observed specific interactions with BMP2, it was necessary to elucidate which of these GAG types could be involved in this specific association. Although the prime candidate for this interaction is a heparan sulfate, analogous growth factor interactions have also been identified for chondroitin and dermatan sulfates.

Heparan sulfate can be totally depolymerised into its disaccharide components with nitrous acid. This particular characteristic, shared with heparin and keratan sulfate, is essential for the analysis of specific GAG populations. In the case of our analysis of the carbohydrate constituents of our GAG+ samples, degradation due to nitrous acid was diagnostic of heparan sulfate. This probability is primarily due to its heparan sulfate's higher degree of charge patterning via sulfation in comparison to either heparin or keratan sulfate. Ultimately, this charge patterning is responsible for BMP2's specific interaction with HS.

Our analysis utilising the nitrous acid protocol showed a complete degradation of the GAG+ sample set indicating that the majority of sugars in the GAG+ sample set were in fact 1,3-linked and, thus, were heparan sulfate. This result supports the numerous observations in regards to the specificity of heparan sulfate cytokine interactions, particularly the interaction that BMP2 exhibits with heparin and HS.

GAG Species Analysis

BMP2-HBP Specific GAGs (Alternative Species)

The small remnant peak that was observed after the degradation of GAG+ samples by nitrous acid supports the possibility that other sulfated GAGs carrying some specific affinity for BMP2 may be found in the GAG+ sample set. Given our current understanding of the role of sulfation in mediating the interaction between GAGs and BMP2, chondroitins and dermatans are the most likely alternative sugars to show a specific interaction with BMP2 as these show the highest potential diversity in sulfation patterns.

A methodology frequently employed for GAG analysis includes examining the role of individual sulfation positions on GAG-ligand interactions. This method of analysis gives an indication of the importance of individual sulfation positions in maintaining the interaction between the GAG chain and its specific target. Furthermore, since the different species of GAGs only have the potential to carry sulfation patterns specific to their species, this can aid in narrowing the possible glycosaminoglycan candidates that may show an affinity for a specific ligand.

To this end we examined the affinity for the BMP2-HBP carried by variably sulfated CS chains, C4S and C6S, and standard DS. Interestingly, only C4S carried any significant affinity for the BMP2-HBP. This data indicates that it is likely that the 4-O-sulfation is necessary for CS to interact with the BMP2-HBP. Interestingly, dermatan sulfate showed no affinity for the BMP2-HBP. This observation is of interest since DS is the only CS species that demonstrates diversity in sulfation similar to that of HS. Furthermore, our observations indicate a possibility that the epimerisation of GlcA to IdoA in DS compromises the ability of this sugar type to bind the BMP2-HBP. Both C4S and DS are able to carry 4-O-sulfation, yet only small quantities of DS were retained on the column in comparison to C4S. Alternatively, this lack of affinity may simply be due to this particular batch of DS not carrying sufficient 4-O-sulfation to effectively mediate binding to the BMP2-HBP. Interestingly, these particular observations appear to demonstrate an interaction between BMP2 and CS carrying 4-O-sulfation. While previous studies have investigated the use of CS-BMP2 interactions in drug delivery systems, not much is known about any sequence specific interaction between individual CS species and BMP2. However, since HS chains are composed of 1,4-linked disaccharide units, the observed 4-O-sulfation responsible for CS-BMP2 interactions is not found in HS-BMP2 interactions, pointing to a sequence specific interaction not found in CS. Thus it is likely that the remnant peak observed post-nitrous acid treatment may contain small quantities of 4-O-sulfate carrying C4S or DS.

Further investigation revealed that neither commercial HS nor heparin held any significant affinity for the peptide column. The HS used for this assay was purchased commercially from Sigma-Aldrich and was derived from bovine kidney. Given what is known about the tissue specificity of HS it is possible that this commercially available HS, isolated from bovine kidney sources, carried negligible carbohydrate sequences required to specifically mediate an interaction with BMP2. Similarly neither LMW nor HMW heparin showed any affinity for the peptide column. The heparin used for this analysis was also purchased from Sigma-Aldrich, and was derived from porcine intestinal mucosa.

While heparin's interaction with antithrombin III has been well characterised, and notwithstanding its versatile role in the isolation of susceptible molecules, heparin's interaction with growth factors is not, in general, regarded to be specific due to its uniform sulfation. However, given that heparin is routinely used to isolate BMP2, it is somewhat surprising that neither of the heparin samples interacted with the peptide column to any significant degree.

A further possibility for this lack of interaction between the peptide column and heparin is due to the difference in molecular weights between the two molecules. The small BMP2-HBP attached to the column may have difficulty in maintaining its association with the larger, heavily sulfated heparin chain. The inability of heparinase-cleaved heparin to bind the column, however, appeared to indicate that the steric effects of using full length heparin on the column were not solely responsible for disrupting the potential interaction between the sugars and the BMP2-HBP. There is no immediately apparent reason for this inability for commercial heparin to associate with the BMP2-HBP column, though it may be postulated that further spatial separation of the BMP2-HBP from its associated bead via spacer chains may help to ameliorate this problem.

Summary

In this study we have demonstrated the use of affinity chromatography to isolate a subset of glycosaminoglycans that carry a specific affinity for the BMP2-HBP, and have shown the potential for this procedure to yield reproducible results. During this portion of our investigation into the interaction between matrix based GAGs and BMP2, we have made several observations with regards to both the type of GAGs involved in mediating this association and their structure.

Our results have implicated heparan sulfate for mediating the majority of the affinity BMP2 has for the preosteoblast ECM, an interaction which is increasingly recognised as being responsible for the modulation of BMP2 activity. Furthermore, our investigation into the likely structure of the ECM-resident GAGs isolated on the basis of their affinity for the BMP2 heparin-binding site have yielded a surprising result.

Our data indicates that full length BMP2 GAG+ chains do not consist of individual domains with specific affinity for BMP2 interspersed with regions of little or no affinity for the factor. Instead, our results imply that these GAG+ chains consist of multiple BMP2-binding domain repeats. This result is surprising on several levels. Firstly, the repetition required to fulfil this observation over the full length of a >20 kDa carbohydrate chain points to the presence of some manner of synthetic template. Indeed, while previous studies have been unable to derive a template for the assembly of tissue-specific GAG chains, the very fact that such specificity exists supports the presence of a template-based system. Although no genomic template has been elucidated for this process there exists some possibility of a proteomic, perhaps enzymatic, template.

Secondly, this observation provides some evidence as to the importance of the interaction between BMP2 and GAGs. Multiple repeats of the BMP2 affinity site along the length of the carbohydrate chain may be required to ensure maximal binding of BMP2 to the ECM. This particular association has been shown to significantly lengthen the factor's half life, as well as probably being responsible for maintaining a significant local concentration in order to maintain signalling. Alternatively, some studies have proposed a model whereby BMP2 is spatially inhibited from interacting with its receptors due to the interactions with ECM-based GAGs. In this particular scenario the repetition of BMP2 affinity sequences would ensure a maximal binding of the factor, thus reducing the chance of it interacting with its receptors.

Our cumulative results indicated that this system for the isolation of GAGs from the ECM is viable and likely to yield GAG chains that have a specific affinity for BMP2.

This study supports previous findings in regards to the interaction between GAGs and BMP2. Although the prevention of BMP2 associating with the ECM in vitro through the addition of exogenous GAG+ appears to increase BMP2 signalling and upregulates osteogenic gene expression, observations to the contrary have also reported. In these studies, in vivo examination of BMP2's modulation via the HBP showed a distinct improvement in long term osteogenesis when the association with ECM GAGs was increased. It is possible that this interaction plays a major role in maintaining local concentrations by preventing the factor from diffusing away from its sites of primary activity. In light of these studies and our own observations, we propose that BMP2's activity is both positively and negatively regulated by its association with GAGs. Negative regulation may occur precisely via the model proposed by Katagiri and colleagues, whereby the retention of BMP2 in the ECM, away from its receptors, leads to a downregulation of BMP2 signalling. However, cells that require signalling by this factor may potentially secrete various enzymes to remodel extracellular sugar chains, such as sulfatases and heparinases, in order to "clip away" GAGs retaining BMP2 in the ECM, thereby liberating the factor and allowing it to signal, leading to the BMP2-ECM interaction ultimately becoming one of positive maintenance of the cytokine's activity. Alternatively, negative regulation of BMP2 by cell surface GAGs, may be via the internalisation of GAG chains with their associated BMP2 molecules, as has been observed by Jiao and colleagues.

These previous studies, in conjunction with our own observations, have lead us to conclude that the sequence-specific interplay between BMP2 and heparin sulfate represents an intricate control mechanism that has the capacity to both positively and negatively regulate BMP2 signaling. Physiologically this interaction is responsible for enforcing context dependent responses to this potent cytokine in respect to many facets of embryonic development, precursor commitment and wound healing.

Example 2

Purification of BMP2 Peptide Specific HS

We used a peptide having heparin-binding properties from the mature BMP-2 sequence to identify novel HS that bind to the peptide.

Mature BMP-2 amino acid sequence:

[SEQ ID NO: 5]
QAKHKQRKRLKSSCKRHPLYVDFSDVGWNDWIVAPPGYHAFYCHGECP

FPLADHLNSTNHAIVQTLVNSVNSKIPKACCVPTELSAISMLYLDENE

KVVLKNYQDMVVEGCGCR

Heparin-binding peptide amino acid sequence:

[SEQ ID NO: 1]
QAKHKQRKRLKSSCKRHP

To replicate the natural presentation of the heparin-binding site we biotinylated the peptide on it's C-terminus and kept the proline (P) to improve the flexibility/accessibility of the peptide once bound to the streptavidin column.

Isolation of BMP2 Peptide Specific HS

Materials used included a BMP2-peptide coupled Streptavidin column, HiPrep Desalting Column (GE Healthcare), 20 mM PBS+150 mM NaCl (Low Salt Buffer), 20 mM PBS+1.5 M NaCl (High Salt Buffer), HPLC grade Water (Sigma), Biologic-Duoflow Chromatography system (Bio-Rad) and a Freeze Drier.

The column was equilibrated with Low Salt buffer and 1 mg Sigma HS (H9902) was dissolved in low salt buffer and passed through the BMP2-Streptavidin column. Unbound media components were removed from the column by washing low salt buffer (20 mM PBS, pH 7.2, 150 mM NaCl) until the absorbance of the effluent at 232 nm almost return to zero. HS bound to the matrix was eluted with high salt buffer (20 mM PBS, pH 7.2, 1.5 M NaCl). Peak fractions were pooled and freeze dried for 48 hrs.

HS 1 mg was applied to the column and washed with 20 mM PBS buffer containing a low (150 mM) NaCl concentration. After washing with low salt buffer, the bound HS were eluted with 20 mM PBS buffer containing a high (1.5 M) NaCl concentration. Peaks representing retained fractions (monitored at 232 nm) were collected and subjected to further desalting.

After freeze drying 6 mg of positive HS (GAG+) and 1.8 mg of negative HS (GAG−) were obtained.

Example 3

Evaluation of BMP-2 Specific Heparan Sulfates

C2C12 are mouse mesenchymal stem cells normally exhibiting myogenic differentiation but capable of being directed in the osteogenic lineage with supplementation of BMP-2 at passage 3. C2C12 cells at passage 3 were maintained in DMEM with 1000 g/L glucose (low glucose), 10% of FCS, 1% of P/S and without L-glutamine (maintenance media).

DMEM with 1000 g/L glucose (low glucose), 5% of FCS, 1% of P/S and without L-glutamine was used as differentiation media.

Effect of BMP-2 on Osteogenesis

We evaluated the effects of exogenous BMP-2 on osteogenesis by measuring the levels of expression of osteogenic markers (osteocalcin, osterix, Runx2).

Through assaying the effect of addition of different amounts (100 ng/ml and 300 ng/ml) of BMP-2 to the cells we observed a significant decrease at day 5 in the expression of osterix, osteocalcin and Runx2 in cells having 100 ng/ml BMP-2 compared to addition of 300 ng/ml BMP-2 (FIGS.

27-29). Thus we chose this time point for future tests, as any changes should be readily observable.

Materials and Methods

C2C12 cells at passage 3 were used. Cells were kept in liquid Nitrogen at Passage 3 with $1 \times 10^6$ cells/vial. Once cells were taken from liquid Nitrogen, we added 500 µl of culture media, pipetted up and down to refreeze the cells and immediately added 15 ml of culture media.

Culture media was DMEM with 1000 g/L glucose (low glucose), 10% of FCS, 1% of P/S and without L-glutamine. Treatment media was DMEM with 1000 g/L glucose (low glucose), 5% of FCS, 1% of P/S and without L-glutamine.

C2C12 cells were allowed to grow to 75% confluence before harvesting (normally 2 to 3 days) in culture media.

Cells were counted as follows. Media was first aspirated/discarded; 15 ml of PBS added, discard the PBS and add 3 ml of trypsin, incubate at 37° C. for 5 min to lift the cells from the flask. 9 ml of culture media added to neutralize the trypsin. GUAVA used to determine the amount of cells for subsequent cell seeding onto the experiment plates. For example, for 3 sets of 12-well plates 30,000 cells×36 wells× 3.7 cm$^2$=4,000,000 cells. Dilute the cells from the stock and add the desired amount of culture media for cell seeding (each well requiring 500 µl of media with 30,000 cells).

To prepare BMP2 stock 10 µg rhBMP2 (Bone Morphogenetic Protein 2) was resuspended in 100 µl of 4 mM HCl/0.1% BSA.

The following RNA extraction protocol was used. 350 µl of RA1 buffer was used for cell lysis. Cells were frozen with RA1 at −80° C. for one day after which cells were thawed and the lysate filtered for 1 min at 11,000 g. The filtrate was mixed with 350 µl 70% ethanol in 1.5 ml tubes and centrifuged for 30 s at 11,000 g. 350 µl of MDB buffer was added and the mixture centrifuged for 1 min at 11,000 g. 95 µl of Dnase reaction mixture added and mixture left at room temperature for at least 15 min. Then wash with 200 µl of RA2 buffer (to deactivate the Dnase), and centrifuge for 30 s at 11,000 g. Wash with 600 µl of RA3 buffer, centrifuge for 30 second at 11,000 g. Wash with 250 µl of RA3 buffer, centrifuge for 2 min at 11,000 g. Elute the RNA with 60 µl of Rnase-free H$_2$O, centrifuge for 1 min at 11,000 g. Measure the concentration using Nanodrop (unit in ng/µl).

RT (reverse-transcription) experiments were performed as follows. The following were mixed in a PCR tube: Random Primer (0.1 µl), DNTP (1 µl), RNA (250/500 ng), Rnase-Free H$_2$O (topped up to a final volume of 13 µl). Incubate at 65° C. for 5 min. Incubate on ice for at least 1 min. Collect the contents and centrifuge briefly before adding: $1^{st}$ Strand Buffer (4 µl), DTT (1 µl), RnaseOUT (1 µl), SSIII Reverse (1 µl). Top up to final volume of 20 µl. Mix by pipetting up and down. Incubate at room temperature for 5 min. Incubate at 50° C. for 60 mins. Inactivate the reaction at 70° C. for 15 min.

Reverse-transcription experiments were performed twice on separate days and the PCR products pooled together and diluted to a final concentration of 2.5 ng/µl for subsequent Real-Time PCR.

The Real-Time PCR was performed using a TaqMan® Fast Universal PCR master Mix (2×) (Applied Biosystem). PCR master Mix (10 µl), ABI probe (1 µl), cDNA (1 µl), ddH$_2$O (8 µl). GAPDH and Beta actin were used as control genes against the experimental targets OSX (osterix), OCN (Osteocalcin) and Runx2.

Effect of BMP-2 Specific HS GAG+ on Osteogenesis

We evaluated the effects of the BMP-2 specific HS (GAG+) isolated in Example 2 on osteogenesis by measuring the levels of expression of osteogenic markers (osterix, Runx2, alkaline phosphatase and BspII) by quantitative polymerase chain reaction (qPCR). A time course was prepared to compare the expression of the markers over a course of 10 days to compare the control to a low and a high dose of BMP-2, the high dose being the optimal conditions to induce differentiation of the cells.

Materials and Methods

Cells were seeded at 30,000 cell/cm$^2$ in maintenance media and left to attach overnight. The following day we switched to differentiation media with:

No additives
100 ng/ml BMP-2 (positive control)
100 ng/ml BMP-2+30 µg/ml −GAG (Neg GAGs)
100 ng/ml BMP-2+30 µg/ml +GAG (Pos GAGs)
100 ng/ml BMP-2+30 µg/ml Heparin (Sigma # H3149)
100 ng/ml BMP-2+30 µg/ml Total Heparan Sulfate (Sigma # H9902—HS prior to fractionation)

The carbohydrates and BMP-2 were mixed together in the smallest volume possible and incubated at room temperature for 30 minutes before their addition to the media and on the cells.

After 5 days, RNA was extracted using the Macherey-Nagel kits and Reverse-Transcription was performed.

As we show in FIGS. 30-33, the Heparan sulfate from porcine mucosa (Total HS) can increase the activity of BMP-2 (shown through GAG+ induced increases in the expression of Alkaline Phosphatase, osterix, BspII and Runx2) and this activity is contained within the fraction that binds BMP2 (Pos GAGs). This means that we can isolate the BMP enhancing fraction of a commercial HS by passing them on the BMP-HBD peptide column.

Example 4

MC3T3-E1 (s14) preosteoblast cells (a mouse embryo calvaria fibroblast cell line established from the calvaria of an embryo) were expanded in αMEM media supplemented with 10% FCS, 2 mM L-glutamine, 1 mM sodium pyruvate and Penicillin/Streptomycin every 72 hours until sufficient cells were generated for plating. The cells were differentiated by plating at $5 \times 10^4$ cells/cm$^2$ in αMEM media supplemented with 10% FCS, 2 mM L-glutamine, 25 µg/ml ascorbic acid, 10 mM β-glycerol phosphate and Penicillin/Streptomycin. The media was changed every 72 hours for 8 days at which point the cells and media were harvested. The media was retained and clarified by high speed centrifugation and filtration through a 0.4 µm filter. The cell layer was disrupted using a cell scraper and an extraction buffer containing PBS (150 mM NaCl w/o Ca$^{2+}$ and Mg$^{2+}$), 1% CHAPS, 8 M Urea and 0.02% NaN$_3$.

At all stages (unless otherwise stated), samples were clarified before loading onto column systems. This process included high speed centrifugation at 5000 g for 30 min, and filtration through a 0.4 µm syringe filter. The samples were always clarified directly prior to loading through the column system to prevent precipitates forming in stagnant solutions.

Anion exchange chromatography was used to isolate proteoglycosaminoglycan (PGAG) fractions from both the media and cell layer samples. In each case, the media or cell layer samples were run through a Pharmacia XK 26 (56-1053-34) column packed with Capto Q Anion Exchange Beads (Biorad) at a flow rate of 5 ml/min on a Biologic DuoFlow system (Biorad) using a QuadTec UV-Vis detector. The samples were loaded in a low salt buffer containing PBS (150 mM NaCl w/o Ca$^{2+}$ and Mg$^{2+}$), 100 mM NaCl, 0.02% NaN$_3$ at pH 7.3. The samples were eluted in a high salt buffer containing PBS (150 mM NaCl w/o Ca$^{2+}$ and Mg$^{2+}$), 850 mM NaCl and 0.02% NaN$_3$ at pH 7.3. The relevant fractions were collected and pooled into a single PGAG sample and lyophilized in preparation for desalting.

The PGAG sample was desalted through four sequentially joined Pharmacia HiPrep™ 26/10 (17-5087-01) columns at a flow rate of 10 ml/min on a Biologic DuoFlow system (Biorad) using a QuadTec UV-Vis detector. The relevant fractions were collected and pooled into a single sample set and lyophilized in preparation for further treatment.

In the fourth step, the PGAG sample set obtained from the desalting procedure was subjected to a pronase and neuraminidase treatment, in order to digest away core proteins and to subsequently liberate GAG chains. In this respect, lyophilized PGAG samples were resuspended in a minimum volume of 25 mM sodium acetate (pH 5.0) and clarified by filtration through a 0.4 µm syringe filter. The total sample volume was dispensed into 10 ml glass tubes in 500 µl aliquots. To this aliquot was added 500 µl of 1 mg/ml neuraminidase before the mixture was incubated for 4 hours at 37° C. Following incubation, 5 ml of 100 mM Tris-acetate (pH 8.0) was added to each sample. An additional 1.2 ml of 10 mg/ml pronase, reconstituted in 500 mM Tris-acetate and 50 mM calcium acetate (pH 8.0), was added to each sample before the mixture was incubated for 24 hrs at 36° C. Following this treatment, all volumes were combined and prepared for anion exchange chromatography by centrifugation and filtration.

In a fifth step, the GAG sample isolated following protein cleavage was eluted through a Pharmacia XK 26 (56-1053-34) column packed with Capto Q Anion Exchange Beads (Biorad) at a flow rate of 5 ml/min on a Biologic DuoFlow system (Biorad) using a QuadTec UV-Vis detector. In this respect, the sample was loaded in a low salt buffer containing PBS (150 mM NaCl w/o Ca$^{2+}$ and Mg$^{2+}$) and 0.02% NaN$_3$ at pH 7.3. The sample was eluted in a high salt buffer containing PBS (150 mM NaCl w/o Ca$^{2+}$ and Mg$^{2+}$), 850 mM NaCl and 0.02% NaN$_3$ at pH 7.3. The relevant fractions were pooled, lyophilized and desalted as per the aforementioned protocol for desalting the PGAG sample.

N-terminal biotinylated peptide (1 mg), corresponding to the heparin-binding domain of BMP-2, and comprising an amino acid sequence represented by QAKHKQRKRLKSS-CKRH [SEQ ID NO:6], was mixed with low salt buffer containing PBS (150 mM NaCl w/o Ca$^{2+}$ and Mg$^{2+}$). The mixture was eluted through a column packed with a streptavidin-coated resin matrix. The column was then exposed to a high salt buffer containing PBS (150 mM NaCl w/o Ca$^{2+}$ and Mg$^{2+}$), 850 mM NaCl and 0.02% NaN$_3$ at pH 7.3, to ascertain whether, under those conditions the peptide had bound securely to the matrix. No substantial loss of peptide from the column was observed. The column was subsequently washed with the low salt buffer in preparation for sample loading.

The GAG mixture (2 mg), isolated using the procedure outlined in Example 1, was suspended in low salt sodium phosphate buffer (1 mL), and loaded onto the peptide column of Example 2. The sample was eluted with a low salt buffer containing PBS (150 mM NaCl w/o Ca$^{2+}$ and Mg$^{2+}$). A peak corresponding to GAGs with negligible BMP-2 affinity was observed in the UV-Vis detector trace. The column fractions responsible for giving rise to this peak were combined. These fractions are known as 'GAG−'—the minus sign denoting the lack of affinity with the column. When it became evident from the UV-Vis detector that the trace had flattened to the baseline, and that no further oligosaccharide was eluting, the eluting solvent was changed to a high salt buffer containing PBS (150 mM NaCl w/o Ca$^{2+}$ and Mg$^{2+}$), 850 mM NaCl and 0.02% NaN$_3$ at pH 7.3. Following this change in the eluting solvent, a peak corresponding to BMP-2 specific GAGs was observed in the UV-Vis detector trace. The column fractions responsible for giving rise to this peak were combined. These fractions are known as 'GAG+'—the plus sign denoting the presence of affinity with the column. In the case of GAG compounds sourced from preosteoblast cells, the GAG+ fraction represented 10% of the overall GAG mixture.

Example 5

The addition of BMP2 has a clearly defined capacity to induce osteogenic differentiation in C2C12 myoblasts. Similarly, the pre-incubation of BMP2 with heparin has been shown to both extend the cytokines half life and its immediate potency in vitro. Here we examined the capacity of GAG+ and GAG− fractions to augment the osteoinduction of C2C12 cells in vitro by BMP2.

The GAG+ sample from Example 4 (0, 10, 100, 1000 ng/mL) was added to C2C12 myoblasts in vitro in the presence of BMP-2 (0, 50, 100 ng/mL). Measurement of the relative expression of the osteocalcin gene indicated that the GAG+ sample was able to potentiate BMP-2 to effect osteocalcin gene expression at levels of BMP-2 far below those currently used in therapy (300 ng/mL). The results of this assay (including calculated p-values and errors) are represented graphically in FIG. 34 in which the experimental conditions for each 'culture condition' are as follows:

1. Control cells, no BMP-2 added, no GAG added
2. BMP-2 at 50 ng/mL
3. BMP-2 at 50 ng/mL, GAG+ at 10 ng/mL
4. BMP-2 at 50 ng/mL, GAG+ at 100 ng/mL
5. BMP-2 at 50 ng/mL, GAG+ at 1000 ng/mL
6. BMP-2 at 100 ng/mL
7. BMP-2 at 100 ng/mL, GAG+ at 10 ng/mL
8. BMP-2 at 100 ng/mL, GAG+ at 100 ng/mL
9. BMP-2 at 100 ng/mL, GAG+ at 1000 ng/mL Interestingly, while 1000 ng/ml of GAG+ is able to significantly augment BMP2 mediated osteocalcin expression, the addition of concentrations of GAG+ below 1000 ng/ml appear to progressively inhibit this expression. Furthermore, the addition of sufficient GAG+ also managed to drive the induction of osteocalcin by 50 ng/ml of BMP2 above that of 100 ng/ml of BMP2 on its own, indicating the potency of this interaction.

This cell culture based analysis demonstrated that the addition of GAG+ to C2C12 osteogenic cultures together with BMP2 resulted in a significant upregulation of osteocalcin expression indicating an increase in BMP2 signalling efficacy. This result supports the specific association of GAG+ chains with BMP2, thereby blocking the BMP2-HBP and preventing its association with matrix-based PGAGs. The resulting upregulation of osteogenic gene expression is comparable to that observed in previous studies utilising heparin to achieve a similar effect. Interestingly, the addition of concentrations of GAG+ that fall below 1000 ng/ml appear to have an initially antagonistic effect on BMP2 signalling.

One possible hypothesis to explain this observation revolves around the capacity for a given number of GAG+ molecules to bind a certain number of BMP2 molecules. Under conditions where no exogenous GAG+ is added to the culture system the majority of BMP2 molecules will be able to associate with the ECM, thereby being localised away from their cognate receptors and being unable to immediately initiate signalling. Subsequent dissociation of BMP2 from the ECM, both spontaneously and by targeted enzymatic alteration of their associated GAG chains, has the capacity to induce long term BMP2 signalling. The addition of a large number of GAG+ molecules to this system, as is the case in samples supplemented with 1000 ng/ml of GAG+, permits the majority of BMP2 molecules to remain in solution where they are free to mediate receptor dimerisation and induce downstream signalling. Both these processes of cytokine/receptor interaction likely require particular concentration thresholds in order maintain an efficient level of signalling. Under culture conditions containing 50 ng/ml of BMP2, the addition of low concentrations of GAG+ allows for a portion of the available cytokine to remain soluble while the remaining portion associates with the ECM. Under these conditions only a small quantity of BMP2 remains soluble but, due to its low concentration, becomes highly diffuse in the media leading to negligible signalling. Similarly, due to a portion of the BMP2 remaining solubilised, a reduced quantity of BMP2 can be found in the ECM, resulting in a decrease in signalling from BMP2 liberated from the ECM by direct cellular activity. However, under culture conditions containing 100 ng/ml of BMP2 the combined effects of soluble and ECM based BMP2 are, with the addition of 100 ng/ml of GAG+, sufficient to induce BMP2 signalling similar to control levels. Without further study, however, the dynamics involved in BMP2/GAG+ signalling remain unclear. Future studies utilising surface plasmon resonance may help elucidate the efficiency of BMP2/GAG+ interactions and may aid in clarifying these observations.

Example 6

The enzyme heparanase 3 was used to cleave GAG+ and GAG− sugar chains from Example 4 according to the following method. GAG+ and GAG− were each treated separately at a concentration of 4 mg/mL, with heparanase 3 (250 mU enzyme per 100 µg oligosaccharide) for 16 hours at 37° C. Subsequently, the mixture was heated for 5 minutes at 70° C. to inactivate the heparanase 3. The digested GAG+ and GAG− mixtures were each subjected to the peptide column separately. The UV-Vis detector trace of each chromatographic run indicated that the digested material showed the same affinity for the column as the undigested material.

Example 7

Coupling of Biotinylated Peptide to Streptavidin Column
Method: BMP2 HB—peptide was dissolved in 20 mM phosphate buffer, 150 mM NaCl (Low Salt Buffer), at a concentration of 1 mg/ml. The peptide solution was subjected to affinity chromatography on a streptavidin column (1 ml) equilibrated in low salt buffer using a low-pressure liquid chromatography (Biologic-Duoflow chromatography system from Bio-Rad). The medium was loaded at a flow rate of 0.2 ml/min and the column washed with the same buffer until the baseline reached zero. To check that the peptide actually attached to the column, the column was eluted with a step gradient of 1.5 M NaCl (high salt buffer) and re-equilibrated with low salt buffer.

The BMP2 heparin binding site (5 mg) sequence (QAKHKQRKRLKSSCKRHP-NHET biotin (SEQ ID NO: 1)) was synthesized and coupled to the 1 ml streptavidin column (GE Healthcare). The chromatogram (FIG. 36) shows all peptides bounds tightly to the streptavidin beads.

Purification of BMP2-Specific Heparan Sulfate
Method: Celsus HS was dissolved in 20 mM phosphate buffer, 150 mM NaCl (Low Salt Buffer), at a concentration of 1 mg/ml. The peptide solution was subjected to affinity chromatography on a streptavidin column (1 ml) equilibrated in low salt buffer using a low-pressure liquid chromatography (Biologic-Duoflow chromatography system from Bio-Rad). The medium was loaded at a flow rate of 0.2 ml/min and the column washed with the same buffer until the baseline reached zero. The bound BMP2 specific HS was eluted with a step gradient of 1.5 M NaCl (high salt buffer), the peak factions were collected, and the column re-equilibrated with low salt buffer. The elution peak (BMP2+ve) and flow through peak (BMP2−ve) HS were collected separately, freeze-dried and stored at −20° C.

The chromatogram (FIG. 37) shows a small portion (~15-20%) of the HS specifically bound to the column and that it eluted in the high salt buffer.

Desalting of BMP2 Peptide Column Bound HS
Method: BMP2 specific HS was dissolved in 10 ml distilled water. The samples were subjected to desalting chromatography on a Hi-prep desalting column (10 ml) equilibrated in distilled water using a low-pressure liquid chromatography (Biologic-Duoflow chromatography system from Bio-Rad). The HS was loaded at a flow rate of 10 ml/min and the column washed with distilled water. The pure HS fractions were collected, freeze-dried and stored at −20° C.

The chromatogram (FIG. 38) shows a clear separation of pure BMP2 specific HS (absorbance peak) and the Salt buffer (conductance peak).

Desalting of BMP2 Peptide Column Unbound HS
Method: The non-specific HS was dissolved in 10 ml distilled water. The samples were subjected to desalting chromatography on a Hi-prep desalting column (10 ml) equilibrated in distilled water using a low-pressure liquid chromatography (Biologic-Duoflow chromatography system from Bio-Rad). The HS was loaded at a flow rate of 10 ml/min and the column washed with distilled water. The pure HS fractions were collected, freeze-dried and stored at −20° C.

The chromatogram (FIG. 39) shows a clear separation of the unbound HS (absorbance peak) and the Salt buffer (conductance peak).

SAX-HPLC Disaccharide Analysis-BMP2 Positive HS
Method: Samples (100 µg) were dissolved in 100 mM sodium acetate/0.2 M calcium acetate, pH 7.0. Heparinase, heparitinase I and II were all used at a concentration of 10 mU/ml in the same buffer. Each sample was sequentially digested for a recovery of disaccharides for SAX-HPLC analysis; for this the samples were digested at 37° C. as follows: heparinase for 2 h, heparitinase I for 1 h, heparitinase II for 18 h, and finally an aliquot of each lyases for 6 h. Samples were run on a BioGel P-2 column (1×120 cm) equilibrated with 0.25 M $NH_4HCO_3$. The disaccharide peak was lyophilized and then dissolved in acidified water (pH 3.5 with HCl). This was passed over a ProPac PA-1 SAX-HPLC column (Dionex, USA), attached to a high pressure liquid chromatography system and the HS disaccharides eluted with a linear gradient 0 to 1.0 M NaCl, pH 3.5, over 60 min at a flow-rate of 1 ml/min. The peaks identified using HS disaccharides standards (Seikagaku, Tokyo, Japan and Iduron) monitored at $A_{232}$ nm.

The HS retained by the BMP2 peptide affinity column was subjected to an enzymatic disaccharide analysis by exposing it to a combination of heparin lyases (heparinase, heparitinase I and II) to completion and then subjecting the resulting disaccharide fragments to strong anion exchange HPLC (SAX-HPLC). The peaks on the chromatogram (FIG. 40) allow us to estimate the relative proportions of each of the component disaccharides within the binding HS population. The analysis shows that greater proportion of disaccharides in the BMP2-binding peptide HS population have an N-sulfated glucosamine.

SAX-HPLC Disaccharide Analysis—BMP2 Negative HS

The HS that did not the BMP2 peptide affinity column was subjected to an enzymatic disaccharide analysis by exposing it to a combination of heparin lyases (heparinase, heparitinase I and II) to completion and then subjecting the resulting disaccharide fragments to strong anion exchange HPLC (SAX-HPLC). The peaks on the chromatogram (FIG. 41) allow us to estimate the relative proportions of each of the component disaccharides within the HS population. The analysis shows that greater proportion of disaccharides in the flow through HS population have an N-sulfated glucosamine.

SAX-HPLC Disaccharide Profile of Celsus Total HS

The Total HS bought from Celsus as the starting material was also subjected to a enzymatic disaccharide analysis by exposing it to a combination of heparin lyases (heparinase, heparitinase I and II) to completion and then subjecting the resulting disaccharide fragments to strong anion exchange HPLC (SAX-HPLC). The peaks on the chromatogram (FIG. 42) allow us to estimate the relative proportions of each of the component disaccharides within the HS population.

ESPR—Analysis of BMP2 Positive and BMP2 Negative HS

Method: BMP2+ve and −ve HS (10 mg/ml) was dissolved in 1 ml 0.1 M MES, pH 5.5 and 300 µl 0.1 MES, pH 5.5, containing 2 mg/ml biotin-LC-hydrazide (Pierce), EDC (7 mg) was added to the mixture and incubated at room temperature for 2 h before addition of another 7 mg of EDC. After a further 2 h incubation, unincorporated biotin was removed with a desalting column (Amersham Pharmacia). The BMP2+ve and −ve HS were tested for their capacity to bind soluble BMP2. Real time binding analysis was carried out using SPR, wherein biotin thiol-coated gold sensor chips were used as a platform for immobilized streptavidin. Using a biotin-streptavidin-biotin bridge, biotinylated HS could be immobilized on the sensor chip. The growth factor (200 nM) was then added to the solution bathing the immobilized HS and incubated for 20 min. Real time binding was monitored by measuring the change in the minimum reflectance angle ($\theta$) over time.

FIG. 44 shows Surface Plasmon Resonance (SPR) analysis of protein-sugar interactions. As shown by the curves, which reflect the avidity of the "on-rate" (Ka), BMP2 does not bind as avidly to the "flow-through" HS, as evidenced by the smaller angle shift, as to the BMP2-binding HS.

BMP2 Binding Capacity of BMP2+Ve and BMP2 −Ve Celsus HS Preparations Coated on an Iduron Heparin/GAG Binding Plate Method: BMP2 was dissolved in Blocking Solution (0.2% gelatin in SAB) at a concentration of 3 µg/ml and a dilution series from 0-3 µg/ml in Blocking Solution established. Dispensing of 200 µl of each dilution of BMP2 into triplicate wells of Heparin/GAG Binding Plates pre-coated with heparin; incubated for 2 hrs at 37° C., washed carefully three times with SAB and 200 µl of 250 ng/ml biotinylated anti-BMP2 added in Blocking Solution. Incubation for one hour at 37° C., wash carefully three times with SAB, 200 µl of 220 ng/ml ExtrAvidin-AP added in Blocking Solution, Incubation for 30 mins at 37° C., careful washing three times with SAB and tap to remove residual liquid, 200 µl of Development Reagent (SigmaFAST p-Nitrophenyl phosphate) added. Incubation at room temperature for 40 minutes with reading at 405 nm within one hour.

The specially-prepared plate surface (Iduron) adsorbs GAGs without modification whilst retaining their protein binding characteristics. Binding occurs at room temperature from physiological buffers. The results (FIG. 45) demonstrate the greater affinity of the BMP2-selected HS preparations for BMP2 over the flow-through or native preparations. BMP2 acted as the control.

ALP Activity of BMP2 Positive and Negative HS on C2C12 Cells

Methods: ALP Assay. C2C12 cells were plated at 20,000 cells/cm$^2$ in a 24-well plate in DMEM (Sigma-Aldrich Inc., St. Louis, Mo.) containing 10% FCS (Lonza Group Ltd., Switzerland) and antibiotics (1% Penicillin and 1% Streptomycin) (Sigma-Aldrich Inc., St. Louis, Mo.) at 37° C./5% $CO_2$. After 24 hours, the culture media was switched to 5% FCS low serum media containing different combinations of 100 ng/mL BMP2 (R&D Systems, Minneapolis, Minn.), 3 mg/mL Celsus HS and varying concentrations of BMP2-specific (+ve HS) and non-specific (−ve HS) Celsus HS preparations. Cell lysis was carried out after 3 days using RIPA buffer containing 1% Triton X-100, 150 mM NaCl, 10 mM Tris pH 7.4, 2 mM EDTA, 0.5% Igepal (NP40), 0.1% Sodium dodecyl sulphate (SDS) and 1% Protease Inhibitor Cocktail Set III (Calbiochem, Germany). The protein content of the cell lysate was determined by using BCA protein assay kit (Pierce Chemical Co., Rockford, Ill.). ALP activity in the cell lysates was then determined by incubating the cell lysates with p-nitrophenylphosphate substrate (Invitrogen, Carlsbad, Calif.). The reading was normalized to total protein amount and presented as relative amount to the group containing BMP2 treatment alone.

FIG. 46 shows BMP-2 specific HS (+ve HS) enhanced alkaline phosphatase (ALP) activity induced by BMP-2 at a greater degree compared to non-specific HS (−ve HS). BMP-2 at 100 ng/mL was introduced alone or in combination with 30 µg/mL Celsus HS or varying concentration of specific and non-specific HS. Specific and non-specific HS was introduced alone at 30 µg/mL.

ALP Staining

Method: ALP Staining. C2C12 cells were cultured as described above. After 3 days of treatment, the cell layer was washed in PBS and stained using Leukocyte Alkaline Phosphatase Kit (Sigma-Aldrich Inc., St. Louis, Mo.) according to manufacturer's specification. Briefly, the cell layer was fixed in citrate buffered 60% acetone and stained in alkaline-dye mixture containing Naphthol AS-MX Phosphatase Alkaline and diazonium salt. Nuclear staining was performed using Mayer's Hematoxylin solution.

BMP-2 specific HS (+ve HS) enhanced alkaline phosphatase (ALP) activity induced by BMP-2 at a greater degree compared to non-specific HS (−ve) when evaluated histochemically (FIG. 47). BMP-2 at 100 ng/mL was introduced in combination with 0, 0.3, 3 and 30 µg/mL of GAG.

BMP2 Stability

Method: Smad 1/5/8 Phosphorylation. C2C12 cells were plated at 20,000 cells/cm$^2$ in a 24-well plate in DMEM (Sigma-Aldrich Inc., St. Louis, Mo.) containing 10% FCS (Lonza Group Ltd., Switzerland) and antibiotics (1% Penicillin and 1% Streptomycin) (Sigma-Aldrich Inc., St. Louis, Mo.) at 37° C./5% CO2. After 24 hours, the culture media was switched to 5% FCS low serum media. Treatment conditions containing 100 ng/mL BMP2 (R&D Systems, Minneapolis, Minn.) in the presence/absence of 3 mg/mL of heparin (Sigma-Aldrich Inc., St. Louis, Mo.) or BMP2-specific (+ve HS) Celsus HS were added 24 hours after the cells have been equilibrated in low serum media. Cell lysate was harvested in 1× Laemmli buffer at 0, 24, 48 and 72 hour time points. The lysate was separated in NuPAGE Novex 4-12% Bis-Tris Gel (Invitrogen, Carlsbad, Calif.) and analyzed with western blot using antibodies against Phospho-Smad 1/5/8 (Cell Signaling, Danvers, Mass.) and Smad 1/5/8 (Santa Cruz Biotechnology Inc., Santa Cruz, Calif.).

The ability of the BMP2-binding HS, i.e. HS3, to prolong the effects of BMP2 on cells (presumably in part by protecting the protein against proteolytic degradation) was compared to the effects of commercial heparin. C2C12 cells were exposed to nothing, BMP2 alone, BMP2+Heparin or BMP2+HS3 for 72 hours and the levels of phosphorylation of the BMP2-specific intracellular signaling molecule Smad1/5/8 monitored by immunoblotting (FIG. 54). The results demonstrate that the HS3 can prolong BMP2 signalling to levels that equal or exceed those of heparin.

Example 8

This experiment was designed to investigate whether HS3, when combined with Smith & Nephew's bone void filler JAX™ gel+Tri-calcium phosphate (TCP) stars can speed up long bone repair.

A non union critical defect is created in the ulna of adult rabbits, the stars placed in the defect, the wound closed and repair monitored after 4 and 8 weeks with a combination of histology and imaging.

Biomaterials

JAX™ is a β-tricalcium phosphate (TCP) synthetic bone substitute manufactured by Smith and Nephew Orthopaedics Ltd, USA. JAX™ consists of six-armed granules, which interlock to provide 55% intergranular porosity in a defect site, allowing cell and vascular infiltration. The clinical indication is for non-load bearing bony defects of 4-5 cm. JAX™ also includes a hydrogel component.

In Vitro Study

The release of heparin at either high or low concentrations (as a substitute for HS) from Jax gel/TCP mixtures in vitro was assessed by first labeling it with Alexa Fluor 488 dye and then monitoring its release into PBS in culture plates. Release in both cases was rapid and bursting.

Fluorescent Labeling of Heparin.

For non-biological in vitro assays, heparin, a hypersulfated member of the HS glycosaminoglycan family, was conjugated with Alexa Fluor 488 (A488, Molecular Probes, UK) using a method published previously by our group (E. V. Luong, L. Grondahl, V. Nurcombe, S. Cool. In vitro biocompatibility and bioactivity of microencapsulated heparan sulfate Biomaterials 2007; 28:2127 2136). Briefly, 3 mg of heparin (H-3149) was solubilized in 300 µL of 0.1 M solution of 4-morpholinoethanesulfonic acid (MES, M3671) buffer (pH 4.5) and combined with 50 µL of a 10% 1-ethyl-3-(3-dimethylaminopropryl) carbodiimide hydrochloride (EDC, Fluka 03449) solution in 0.1 M MES buffer. Subsequently, a 1% A488 solution (50 µl) in 0.1 M MES buffer was added to the heparin/EDC solution. The mixture was protected from light and incubated overnight at room temperature. The fluorescently conjugated heparin was eluted on an Amersham PD10 desalting column. The labeling efficiency was approximately 1.3 mol A488/mol heparin.

Release Profile.

Three JAX™ granules were loaded with either 17 or 170 µg of A488-heparin (50 µL in 100 µL hydrogel), protected from light, and placed in 1 mL of PBS at 37° C. for 48 h. At 1, 2, 3, 4, 5, 6, 24 and 48 h, 100 µL of conditioned phosphate buffered saline (PBS) was collected for sampling and replaced with fresh PBS. The concentration of released A488-heparin was quantified by fluorometry and cumulative release of A488-heparin was reported as a percentage of loading concentration (FIG. 56).

In Vivo Study

Experimental Design.

(See FIG. 55) Twenty male New Zealand White rabbits (weighing 2-2.5 kg) received bilateral ulna defects. Each defect was randomly assigned to one of three experimental groups. Every defect received 18 JAX™ granules and 150 µL of hydrogel containing one of the following treatments: 30 µg HS, 100 µg HS or an equal volume of PBS (50 µL). After 4 and 8 weeks of implantation, the rabbits were sacrificed and ulnas were harvested. Four ulnas per treatment were assessed non-destructively using 2D X-rays and micro-computed tomography (micro-CT) for mineral formation at both time-points. Subsequently, these ulnas were processed for histology and immunohistochemistry. At week 8, an additional three samples per treatment were included for evaluation by torsional testing. Some defects were left empty to serve as internal controls to ensure that the model was truly non-union.

X-Ray Monitoring of New Bone Formation in Defect Sites

HS3 was applied in Jax gel at two different concentrations (30 and 100 ug—called HS30 and HS100) and assessed for new bone formation compared to no treatment over 0, 4 and 8 weeks. The HS-treated animals show clear indication of new bone formation over the controls.

Radiographic Analyses.

JAX™ granules are radio-opaque and therefore difficult to distinguish from new bone in the defect site on 2D x-rays. However, at the early time points, voids between the granules and immediately adjacent to the radius are clearly visible and the progression of bone formation in these spaces can be monitored (S. A. Clarke, N. L. Hoskins, G. R. Jordan, D. R. Marsh. Healing of an ulnar defect using a proprietary TCP bone graft substitute, JAX™, in association with autologous osteogenic cells and growth factors. Bone 2007; 40: 939-947). An Imaging Radiographic System (MUX-100, Shimadzu) was used to capture 2D images of the ulna defects immediately after the surgery and at weeks 4 and 8. Digital micrographs are then taken of the X-rays. X-rays were taken under general anesthesia. X-ray micrographs are shown in FIGS. 51, 52 and 57.

Micro CT Monitoring of New Bone Formation in Defect Sites

HS3 given at doses of 30 and 100 ug (HS30 and HS100) at the time of surgery was compared to PBS star alone controls using micro CT (computerized tomography) imaging (FIGS. 51, 52 and 58).

Micro-CT Analyses.

At weeks 4 and 8, harvested ulnas were scanned with a micro CT scanner (Skyscan 1076; Skyscan, Belgium). Scanning was performed with a resolution of 35 µm and a scanning width of 68 mm. The scanner was set at a voltage of 104 kV and a current of 98 µA. Cone-Beam CT-reconstruction A Sasov software (Skyscan) was used to convert the isotropic slice data obtained into 2D images. For this reconstruction, the lower and upper threshold values for bone were assumed to be −315 and 543 Hounsfield units. The data was then analyzed and remodeled using the associated CTAn software (Skyscan) for quantification and Mimics 11.1 software (Materialise, Belgium) to render 3D images. A cylindrical region of interest (ROI, cocentrically positioned over the defect site) and the total number of slices (corresponding to the length of the defect) was kept constant for all the samples. The total volume of newly formed bone within the ROI was measured by assigning predetermined thresholds for total bone content, cortical bone (JAX™ and radii) and trabecular bone (or newly formed bone). The data was reported as bone volume/total volume (%).

HS3 (at both 30 µg and 100 µg doses) significantly increased the BV/TV (%) as compared to controls. There was no significant difference between HS30- and HS100-treated ulnas (FIG. 59).

Histology

After the designated experimental periods, bone was harvested, fixed, decalcified, sectioned and mounted for staining with various dyes.

FIGS. 60 and 61 show H&E staining (vide infra) for the 3 treatment groups over weeks 4 and 8. HS3-treatment clearly shows more tissue infiltrating the defect than in controls.

Higher magnification H&E-stained micrographs (FIG. 61) revealed new bone being deposited immediately adjacent to the Jax stars (the clearer islands), with greater amounts of bone, bone marrow and cartilaginous tissue apparent in the HS treated animals. By week 8, in the HS-treated ulnas, new bone has remodeled and matured.

Histological Analyses.

The extracted ulnas were fixed in 10% neutral buffered formalin for 1 week under vacuum, and decalcified in 15% EDTA, pH 7.2, for 4 weeks at room temperature. Then, the ulnas were processed using a vacuum infiltration processor (Sakura Finetek, Japan) with a 14 h program. After dehydration and clearing, the bones were embedded in Paraplast paraffin wax (Thermo Scientific) and the paraffin blocks sectioned longitudinally at 5 µM using a rotary microtome (Leica Microsystems, Germany). Paraffin sections were placed on positively charge microscope slides, dried, stained with Hematoxylin/Eosin and Modified Tetrachrome and finally examined under an Olympus Stereo (SZX12) and upright fluorescence microscope (BX51).

FIGS. 62 and 63 show Ralis Tetrachrome (Z. A. Ralis, G. Watkins. Modified tetrachrome method for osteoid and defectively mineralized bone in paraffin sections. Biotech and Histochem 1992; 67: 339-345) staining (vide infra) for the 3 treatment groups over weeks 4 and 8. HS-treated defects clearly show more tissue infiltrating the defect than in controls.

Higher magnification Ralis Tetrachrome-stained micrographs (FIG. 63) revealed new bone being deposited immediately adjacent to the Jax stars (the clearer islands), with greater amounts of woven bone, bone marrow and capillaries apparent in the HS3 treated animals. By week 8, in the HS-treated ulnas, new bone has remodeled and matured.

Immunostaining

After the designated experimental periods, bone was harvested, fixed, decalcified, sectioned and mounted for staining with various dyes. FIG. 64 shows immunostaining for the late osteogenic marker osteocalcin (vide infra) for the 3 treatment groups over weeks 4 and 8. H53-treated specimens clearly show more positive (brown) staining filling up the defect than in controls.

Higher magnification (FIG. 65) of the osteocalcin staining revealed new bone being deposited immediately adjacent to the Jax stars (the clearer islands), with greater amounts of remodelling cavities that consist of bone marrow, capillaries and osteoblast-lined borders.

Immunohistochemistry Analysis.

Deparaffinised sections were washed with PBS, incubated with Protease XXIV (BioGenex, San Ramon, USA) for 10 min for antigen retrieval, followed by incubation with 0.3% hydrogen peroxide in water for 20 min at room temperature. After washing, sections were blocked with 5% normal goat serum in PBS for 30 min. Tissue sections were incubated with appropriate concentrations of primary antibodies: osteocalcin (ab13420, 1:150, Abcam, UK) or the same concentration of mouse IgG (MG100, Caltage Lab, USA; as negative controls) in blocking buffer overnight at 4° C. Sections were washed three times with PBS, and then incubated with rat absorbed biotin-labeled anti-mouse IgG (Vector Lab Inc, USA) for 1 h. Sections were washed with PBS and incubated with avidin-biotinperoxidase complex (ABC) solution (Immunopure ABC preoxidase staining kit, Vector Lab. Inc) for 1 h. Peroxidase activity was detected using 3,3-diaminobenzidiine-tetrahydrochloride (DAB; DAKO, USA). Sections were washed, mounted and examined under bright field microscopy using an Olympus SZX12 stereomicroscope.

Torsional Testing

After the designated experimental periods, bones were tested for their mechanical strength. FIG. 66 shows the torsional testing set-ups.

Torsional Testing.

After sacrifice at 8 weeks post-surgery, the rabbit ulnas were retrieved, wrapped in PBS-soaked gauze to maintain moisture, and frozen at −20° C. until torsional testing. Upon thawing, the ulna ends were potted in polymethylmethacrylate (Meliodent Rapid Repair, Heraeus Kulzer), contained within customized plastic blocks and allowed to solidify, to enable stable fixation. Ulnas were subsequently mounted in a MTS 858 Mini Bionix II testing system (MTS, Eden Prairie, Minn.). Polymer blocks and gauze were gently removed prior to testing. Each specimen was then tested to failure in torsion and the resulting torque-angular displacement curves were recorded. The rotation rate used was 1 degree per second until 35 degrees was reached and data were collected at 100 Hz. The stiffness, maximum torque, and angle at failure were recorded for each specimen, with the stiffness being measured as the slope of the linear portion of the torque-angular displacement curve (M. Bostrom, J. M. Lane, E. Tomin, M. Browne, W. Berberian, T. Turek, J. Smith, J. Wozney, T. Schildhauer. Use of bone morphogenetic protein-2 in the rabbit ulnar non-union model. Clin Orthop Relat Res 1996; 327: 272-282).

Statistical Analyses.

Quantitative data was obtained in triplicates and reported as means±standard deviation. Statistical analyses were performed using the Student's t-test (GraphPad software), and a p-value of less than 0.05 was considered significant.

Quantification of Stiffness and Maximum Torque Assessed from Control and HS-Treated Ulnae.

Stiffness was markedly improved for the HS-treated bones. As the stars occupy the largest proportion of the defect, which became a physical barrier for new bone infiltration, it resulted in improvements that were only marked (as opposed to significant)—see FIG. 67.

Example 9

Evaluating Bone Regeneration in a Critical Sized Defect Induced by HS3-Loaded Collagen Sponges The same overall approach to that of Example 8 was used in a second study, except that the Jax TCP stars were replaced with FDA-approved collagen sponges.

Biomaterials.

Collagen sponges were purchased from Integra Life Sciences (HELISTAT, Integra Life Sciences Corp, USA) and measured 7×21×5 mm. These sponges were processed from bovine deep flexor tendon, are bioabsorbable and non-pyrogenic.

The morphology of the sponges was evaluated using Scanning Electron Microscopy (SEM). Briefly, collagen sponges were sputtered-coated with gold and then examined using SEM (Jeol JSM 5310 LV) at an accelerating voltage of 10 kV.

Biomolecules.

Heparan sulfates (HS) tested in this study were bone-morphogenetic protein (BMP) specific HS, also known as HS3.

In Vivo Study

The study used HS3 loaded at 30 μg per sponge (HS30) and BMP-2 loaded at 10 μg per sponge (BMP2-10). Bilateral ulna defects were created and treated with HS30, BMP2-10, or HS30+BMP2-10, or PBS controls.

HS3 (30 μg) was applied in collagen sponges either alone or in combination with BMP2 (10 μg) and assessed for new bone formation compared to no treatment over 0, 4 and 8 weeks. These were assessed against the negative collagen sponge control, and the positive BMP2 control.

Experimental Design.

Twenty male New Zealand White rabbits (weighing 2-2.5 kg) received bilateral ulna defects. Each defect was randomly assigned to one of three experimental groups. Every defect received 1 collagen sponge soaked with one of the following treatments (total 300 μL, in PBS): 30 μg HS, 10 μg BMP-2 (sometimes called BMP10), 30 μg HS+10 μg BMP-2 or an equal volume of PBS. After 4 and 8 weeks of implantation, the rabbits were sacrificed and ulnas were harvested. Four ulnas per treatment were assessed non-destructively using 2D X-rays and micro-computed tomography (micro-CT) for mineral formation at both time-points. Subsequently, these ulnas were processed for histology and immunohistochemistry. At week 8, an additional three samples per treatment were included for evaluation by torsional testing. Some defects were left empty to serve as internal controls to ensure that the model was truly non-union.

Surgical Procedures.

The research protocol for performing bilateral ulna osteotomies in rabbits was approved by the Institutional Animal Care and Use Committee, following all appropriate guidelines. All surgical procedures were carried out under general anesthesia and aseptic conditions. Anesthesia consisted of a combination of ketamine (75 mg/kg) and xylazine (10 mg/kg) injections as well as isoflurane via an induction chamber and facemask for maintenance. A 6 cm skin incision was made and the overlying muscle layers were parted until the length of the ulna was exposed. A 1.5 cm longitudinal defect in the central diaphysis was created using an Acculan.

Radiographic Analyses.

An Imaging Radiographic System (MUX-100, Shimadzu, Japan) was used to capture 2D images of the ulna defects immediately after the surgery and at weeks 4 and 8. Digital micrographs (FIG. 68-69) are then taken of the X-rays. X-rays were taken under general anesthesia. The collagen sponges were not radio-opaque; hence it was easy to identify new bone in the defect site on the 2D X-rays.

X-ray monitoring after 4 weeks reveals significant new bone filling the defect sites in all the treatment cases as compared to the negative controls (FIG. 69).

X-ray monitoring after 8 weeks reveals the achievement of bone union for all treatments, but not in the negative control (FIG. 70). Interestingly, delivery of the HS3 alone resulted in bone union just as good as that seen for the BMP2; the HS3 in combination with the BMP2 did not accelerate this effect because it was already maximal. Micro-CT analyses. At weeks 4 and 8, harvested ulnas were scanned with a μCT scanner (Skyscan 1076; Skyscan, Belgium). Scanning was performed with a resolution of 35 μm and a scanning width of 68 mm. The scanner was set at a voltage of 104 kV and a current of 98 μA. Cone-Beam CT-reconstruction A Sasov software (Skyscan) was used to convert the isotropic slice data obtained into 2D images. For this reconstruction, the lower and upper threshold values for bone were assumed to be −315 and 543 Hounsfield units. The data was then analyzed and remodeled using the associated CTAn software (Skyscan) for quantification and Mimics 11.1 software (Materialise, Belgium) to render 3D images. A cylindrical region of interest (ROI, cocentrically positioned over the defect site) and the total number of slices (corresponding to the length of the defect) was kept constant for all the samples. The total volume of newly formed bone within the ROI was measured by assigning predetermined thresholds for total bone content, cortical bone (radii) and trabecular bone (or newly formed bone). The data was reported as bone volume/total volume (%)—see FIG. 71.

Micro-CT Quantification of the percentage bone volume of total volume (BV/TV) for the treatment groups after weeks 4 and 8 confirmed the effects of the HS3 alone were more than comparable with FDA-approved BMP2 (FIG. 71).

Torsional Testing.

After sacrifice at 8 weeks post-surgery, the rabbit ulnas were retrieved, wrapped in PBS-soaked gauze to maintain moisture, and frozen at −20° C. until torsional testing. Upon thawing, the ulna ends were potted in polymethylmethacrylate (Meliodent Rapid Repair, Heraeus Kulzer), contained within customized plastic blocks and allowed to solidify, to enable stable fixation. Ulnas were subsequently mounted in a MTS 858 Mini Bionix II testing system (MTS, Eden Prairie, Minn.). Polymer blocks and gauze were gently removed prior to testing. Each specimen was then tested to failure in torsion and the resulting torque-angular displacement curves were recorded. The rotation rate used was 1 degree per second until 35 degrees was reached and data were collected at 100 Hz. The stiffness, maximum torque, and angle at failure were recorded for each specimen, with the stiffness being measured as the slope of the linear portion of the torque-angular displacement curve (M. Bostrom, J. M. Lane, E. Tomin, M. Browne, W. Berberian, T. Turek, J. Smith, J. Wozney, T. Schildhauer. Use of bone morphogenetic protein-2 in the rabbit ulnar non-union model. Clin Orthop Relat Res 1996; 327: 272-282). Statistical Analyses. Quantitative data was obtained in triplicates and reported as means±standard deviation. Statistical analyses were performed using the Student's t-test (GraphPad software), and a p-value of less than 0.05 was considered significant.

Quantification of Stiffness and Maximum Torque Assessed from Control, BMP2 and HS-Treated Ulnae.

Both stiffness and maximum torque was significantly improved for the treatment groups. Remarkably, the HS3-alone treatment resulted in mechanical properties that were similar to BMP2 treatment and intact bone at week 8 (FIG. 72).

The invention claimed is:

1. A method of treatment of injury or disease, the method comprising administering, to an individual in need thereof, a therapeutically effective amount of an isolated or substantially purified heparan sulphate composition comprising a heparan sulphate component, wherein the heparan sulphate component is at least 97% HS/BMP2 which is capable of specific binding to SEQ ID NO:1 or 6, and to BMP2, and which is obtained by a method comprising:

(i) providing a solid support having polypeptide molecules adhered to the support, wherein the polypeptide consists of the amino acid sequence QAKHKQRKRLKSSCKRHP [SEQ ID NO:1] or QAKHKQRKRLKSSCKRH [SEQ ID NO:6];

(ii) contacting the polypeptide molecules with a heparan sulphate fraction obtained from mammalian tissue or extracellular matrix such that polypeptide-heparan sulphate complexes are allowed to form;

(iii) partitioning polypeptide-heparan sulphate complexes from the remainder of the mixture;

(iv) dissociating the heparan sulphate from the polypeptide-heparan sulphate complexes by disrupting the polypeptide-heparan sulphate complexes; and (v) collecting the dissociated heparan sulphate; wherein the method comprises the repair and/or regeneration of bone.

2. The method of claim 1 wherein the method is for the treatment of bone defect or bone fracture.

3. The method of claim 2 wherein the method is a treatment of a fracture of a long bone, short bone, flat bone, irregular bone or sesamoid bone.

4. The method of claim 2 wherein the method is a treatment of a fracture or defect of a skeletal bone, bone of the cranio-facial region, bone of the axial skeleton, appendicular bone or bone of the pelvic skeleton.

5. The method of claim 4 wherein the method is a treatment of a fracture or defect of a bone of the head, neck, face, jaw, nose or cheek.

6. The method of claim 1 wherein the method is for the repair or regeneration of bone during dental or facial or cranial surgery, or a spinal disc fusion treatment.

7. The method of claim 2 wherein the bone defect or bone fracture is a critical or non-union bone defect regeneration, compression fracture, compacted fracture, spiral fracture, complete and incomplete fractures, transverse, linear and oblique fractures or comminuted fractures.

8. The method of claim 1 wherein the method is for the treatment of osteoporosis or osteoarthritis.

9. The method of claim 1, wherein the method involves administering the HS/BMP2 directly to the site of injury or disease in order to stimulate the growth, proliferation and/or differentiation of new tissue to effect a repair of the injury or to cure or alleviate the disease condition.

10. The method of claim 2, wherein the method involves injecting HS/BMP2 to the tissue surrounding the fracture.

11. The method of claim 1 wherein the method involves surgically implanting a biocompatible implant or prosthesis comprising HS/BMP2.

12. The method of claim 1, wherein the method further comprises administering mesenchymal stem cells to the patient.

13. The method of claim 1, wherein the method further comprises administering BMP2 to the patient.

14. The method according to claim 1 wherein the HS/BMP2 binds to SEQ ID NO:1 with a KD of less than 1 µM.

* * * * *

SEQUENCE LISTING

<160> NUMBER OF SEQ ID NOS: 6

<210> SEQ ID NO 1
<211> LENGTH: 18
<212> TYPE: PRT
<213> ORGANISM: Homo sapiens

<400> SEQUENCE: 1

```
Gln Ala Lys His Lys Gln Arg Lys Arg Leu Lys Ser Ser Cys Lys Arg
1               5                   10                  15

His Pro
```

<210> SEQ ID NO 2
<211> LENGTH: 396
<212> TYPE: PRT
<213> ORGANISM: Homo sapiens

<400> SEQUENCE: 2

```
Met Val Ala Gly Thr Arg Cys Leu Leu Ala Leu Leu Leu Pro Gln Val
1               5                   10                  15

Leu Leu Gly Gly Ala Ala Gly Leu Val Pro Glu Leu Gly Arg Arg Lys
            20                  25                  30

Phe Ala Ala Ser Ser Gly Arg Pro Ser Ser Gln Pro Ser Asp Glu
        35                  40                  45

Val Leu Ser Glu Phe Glu Leu Arg Leu Leu Ser Met Phe Gly Leu Lys
50                  55                  60

Gln Arg Pro Thr Pro Ser Arg Asp Ala Val Val Pro Pro Tyr Met Leu
65                  70                  75                  80

Asp Leu Tyr Arg Arg His Ser Gly Gln Pro Gly Ser Pro Ala Pro Asp
                85                  90                  95

His Arg Leu Glu Arg Ala Ala Ser Arg Ala Asn Thr Val Arg Ser Phe
            100                 105                 110

His His Glu Glu Ser Leu Glu Glu Leu Pro Glu Thr Ser Gly Lys Thr
        115                 120                 125

Thr Arg Arg Phe Phe Phe Asn Leu Ser Ser Ile Pro Thr Glu Glu Phe
130                 135                 140

Ile Thr Ser Ala Glu Leu Gln Val Phe Arg Glu Gln Met Gln Asp Ala
145                 150                 155                 160

Leu Gly Asn Asn Ser Ser Phe His His Arg Ile Asn Ile Tyr Glu Ile
                165                 170                 175

Ile Lys Pro Ala Thr Ala Asn Ser Lys Phe Pro Val Thr Arg Leu Leu
            180                 185                 190

Asp Thr Arg Leu Val Asn Gln Asn Ala Ser Arg Trp Glu Ser Phe Asp
        195                 200                 205

Val Thr Pro Ala Val Met Arg Trp Thr Ala Gln Gly His Ala Asn His
210                 215                 220

Gly Phe Val Val Glu Val Ala His Leu Glu Glu Lys Gln Gly Val Ser
225                 230                 235                 240

Lys Arg His Val Arg Ile Ser Arg Ser Leu His Gln Asp Glu His Ser
                245                 250                 255

Trp Ser Gln Ile Arg Pro Leu Leu Val Thr Phe Gly His Asp Gly Lys
            260                 265                 270

Gly His Pro Leu His Lys Arg Glu Lys Arg Gln Ala Lys His Lys Gln
        275                 280                 285

Arg Lys Arg Leu Lys Ser Ser Cys Lys Arg His Pro Leu Tyr Val Asp
290                 295                 300
```

```
Phe Ser Asp Val Gly Trp Asn Asp Trp Ile Val Ala Pro Pro Gly Tyr
305                 310                 315                 320

His Ala Phe Tyr Cys His Gly Glu Cys Pro Phe Pro Leu Ala Asp His
                325                 330                 335

Leu Asn Ser Thr Asn His Ala Ile Val Gln Thr Leu Val Asn Ser Val
            340                 345                 350

Asn Ser Lys Ile Pro Lys Ala Cys Cys Val Pro Thr Glu Leu Ser Ala
        355                 360                 365

Ile Ser Met Leu Tyr Leu Asp Glu Asn Glu Lys Val Val Leu Lys Asn
    370                 375                 380

Tyr Gln Asp Met Val Val Glu Gly Cys Gly Cys Arg
385                 390                 395

<210> SEQ ID NO 3
<211> LENGTH: 6
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: Xaa is a hydropathic residue (eg Ala, Gly, Tyr,
      Ser)
<220> FEATURE:
<221> NAME/KEY: VARIANT
<222> LOCATION: (2)..(3)
<223> OTHER INFORMATION: Xaa is a basic residue (eg Lys, Arg, His)
<220> FEATURE:
<221> NAME/KEY: VARIANT
<222> LOCATION: (4)..(4)
<223> OTHER INFORMATION: Xaa is a hydropathic residue (eg Ala, Gly, Tyr,
      Ser)
<220> FEATURE:
<221> NAME/KEY: VARIANT
<222> LOCATION: (5)..(5)
<223> OTHER INFORMATION: Xaa is a basic residue (eg Lys, Arg, His)
<220> FEATURE:
<221> NAME/KEY: VARIANT
<222> LOCATION: (6)..(6)
<223> OTHER INFORMATION: Xaa is a hydropathic residue (eg Ala, Gly, Tyr,
      Ser)

<400> SEQUENCE: 3

Xaa Xaa Xaa Xaa Xaa Xaa
1               5

<210> SEQ ID NO 4
<211> LENGTH: 8
<212> TYPE: PRT
<213> ORGANISM: Artificial Sequence
<220> FEATURE:
<223> OTHER INFORMATION: Consensus sequence
<220> FEATURE:
<221> NAME/KEY: VARIANT
<222> LOCATION: (1)..(1)
<223> OTHER INFORMATION: Xaa is a hydropathic residue (eg Ala, Gly, Tyr,
      Ser)
<220> FEATURE:
<221> NAME/KEY: VARIANT
<222> LOCATION: (2)..(2)
<223> OTHER INFORMATION: Xaa is a basic residue (eg Lys, Arg, His)
<220> FEATURE:
<221> NAME/KEY: misc_feature
<222> LOCATION: (3)..(3)
<223> OTHER INFORMATION: Xaa can be any naturally occurring amino acid
<220> FEATURE:
<221> NAME/KEY: VARIANT
<222> LOCATION: (4)..(4)
<223> OTHER INFORMATION: Xaa is a basic residue (eg Lys, Arg, His)
```

```
<220> FEATURE:
<221> NAME/KEY: VARIANT
<222> LOCATION: (5)..(6)
<223> OTHER INFORMATION: Xaa is a hydropathic residue (eg Ala, Gly, Tyr,
      Ser)
<220> FEATURE:
<221> NAME/KEY: VARIANT
<222> LOCATION: (7)..(7)
<223> OTHER INFORMATION: Xaa is a basic residue (eg Lys, Arg, His)
<220> FEATURE:
<221> NAME/KEY: VARIANT
<222> LOCATION: (8)..(8)
<223> OTHER INFORMATION: Xaa is a hydropathic residue (eg Ala, Gly, Tyr,
      Ser)

<400> SEQUENCE: 4

Xaa Xaa Xaa Xaa Xaa Xaa Xaa Xaa
1               5

<210> SEQ ID NO 5
<211> LENGTH: 114
<212> TYPE: PRT
<213> ORGANISM: Homo sapiens

<400> SEQUENCE: 5

Gln Ala Lys His Lys Gln Arg Lys Arg Leu Lys Ser Ser Cys Lys Arg
1               5                   10                  15

His Pro Leu Tyr Val Asp Phe Ser Asp Val Gly Trp Asn Asp Trp Ile
            20                  25                  30

Val Ala Pro Pro Gly Tyr His Ala Phe Tyr Cys His Gly Glu Cys Pro
        35                  40                  45

Phe Pro Leu Ala Asp His Leu Asn Ser Thr Asn His Ala Ile Val Gln
    50                  55                  60

Thr Leu Val Asn Ser Val Asn Ser Lys Ile Pro Lys Ala Cys Cys Val
65                  70                  75                  80

Pro Thr Glu Leu Ser Ala Ile Ser Met Leu Tyr Leu Asp Glu Asn Glu
                85                  90                  95

Lys Val Val Leu Lys Asn Tyr Gln Asp Met Val Val Glu Gly Cys Gly
            100                 105                 110

Cys Arg

<210> SEQ ID NO 6
<211> LENGTH: 17
<212> TYPE: PRT
<213> ORGANISM: Homo sapiens

<400> SEQUENCE: 6

Gln Ala Lys His Lys Gln Arg Lys Arg Leu Lys Ser Ser Cys Lys Arg
1               5                   10                  15

His
```